(12) United States Patent
Sitt et al.

(10) Patent No.: US 10,799,134 B2
(45) Date of Patent: Oct. 13, 2020

(54) METHODS TO MONITOR CONSCIOUSNESS

(71) Applicant: COMMISSARIAT A L'ENERGIE ATOMIQUE ET AUX ENERGIES ALTERNATIVES, Paris (FR)

(72) Inventors: Jacobo Diego Sitt, Ivry sur Seine (FR); Jean-Remi King, Orleans (FR); Laurent Cohen, Saint Mande (FR); Lionel Naccache, Paris (FR); Stanislas Dehaene, Palaiseau (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 491 days.

(21) Appl. No.: 14/783,942

(22) PCT Filed: Apr. 2, 2014

(86) PCT No.: PCT/IB2014/060385
§ 371 (c)(1),
(2) Date: Oct. 12, 2015

(87) PCT Pub. No.: WO2014/167460
PCT Pub. Date: Oct. 16, 2014

(65) Prior Publication Data
US 2016/0045128 A1 Feb. 18, 2016

(30) Foreign Application Priority Data
Apr. 12, 2013 (EP) ..................................... 13305485

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0042* (2013.01); *A61B 5/0075* (2013.01);
(Continued)

(58) Field of Classification Search
CPC . A61B 5/7246; A61B 5/7253; A61B 5/04845; A61B 5/7282; A61B 5/4821;
(Continued)

(56) References Cited

U.S. PATENT DOCUMENTS

2002/0173729 A1* 11/2002 Viertio-Oja .......... A61B 5/0476
600/544
2006/0135880 A1   6/2006 Mika
(Continued)

FOREIGN PATENT DOCUMENTS

DE    10 2011 115116 A     11/2012
DE    102011115116 A1 *    11/2012  ........... A61B 5/4821
(Continued)

OTHER PUBLICATIONS

Srinivasa 2009 Co-occurrence and Correlation; http://algorithmic-worldview.blogspot.com/2009/01/co-occurrence-and-correlation.html; Pub.Date Jan. 19, 2009, 2 pages.*
(Continued)

*Primary Examiner* — Jeffrey G Hoekstra
*Assistant Examiner* — Patrick M Mehl
(74) *Attorney, Agent, or Firm* — Alston & Bird LLP

(57) ABSTRACT

Provided are methods to measure and or monitor consciousness in a subject, including analyzing brain activity with weighted symbolic mutual information (wSMI) and/or Kolgomorov symbolic complexity (KSC). In addition, methods and apparatus to administer a stimulus and/or a medicament to a subject according to their consciousness level which has been determined using the method described herein are also provided.

8 Claims, 25 Drawing Sheets

(51) Int. Cl.
    A61B 5/0484    (2006.01)
    A61B 5/0478    (2006.01)
(52) U.S. Cl.
    CPC ........ *A61B 5/04008* (2013.01); *A61B 5/0478*
            (2013.01); *A61B 5/04845* (2013.01); *A61B*
            *5/4821* (2013.01); *A61B 5/4839* (2013.01);
                *A61B 5/7246* (2013.01); *A61B 5/7253*
                    (2013.01); *A61B 5/7282* (2013.01)
(58) Field of Classification Search
    CPC ... A61B 5/04017; A61B 5/0478; A61B 5/725;
                    A61B 5/4824; G06F 2203/011
    See application file for complete search history.

(56)                References Cited

U.S. PATENT DOCUMENTS

2007/0167694 A1*  7/2007  Causevic ............ A61B 5/0402
                                                    600/301
2011/0119212 A1*  5/2011  De Bruin ................ A61B 5/00
                                                    706/12
2014/0081094 A1   3/2014  Jordan et al.

FOREIGN PATENT DOCUMENTS

EP            2 535 000 A1    12/2012
WO       WO 2012/150015 A1    11/2012

OTHER PUBLICATIONS

Megchelenbrink 2010 Master Thesis in Information Science, Radboud University Nijmegen, 74 pages, Pub.Date Jul. 2010.*
Musizza et al. 2010 Sensors 10:10896-10935.*
Curran et al. 2002 Brain and Cognition 51:326-336.*
Rosanova et al. 2012 Brain 135:1308-1320 (Year: 2012).*
King et al. 2013 Current Biology 23:1914-1919 (Year: 2013).*
International Search Report and Written Opinion for Application No. PCT/IB2014/060385 dated Jun. 27, 2014.
Balakrishnan, G. et al., *Creating Symbolic Representations of Electroencephalographic Signals: An Investigation of Alternate Methodologies on Intracranial Data*, $32^{nd}$ Annual International Conference of the IEEE EMBS, Buenos Aires, Argentia (Aug. 31-Sep. 4, 2010, pp. 4683-4686.
King, J. R. et al., *Single-Trial Decoding of Auditory Novelty Responses Facilitates the Detection of Residual Consciousness*, NeuroImage 83 (2013) 726-738.
Tupaika, N. et al., *Assessment of the Depth of Anesthesia Based on Symbolic Dynamics of the EEG*, , $32^{nd}$ Annual International Conference of the IEEE EMBS, Buenos Aires, Argentia (Aug. 31-Sep. 4, 2010, pp. 5971-5974.
Adams, J. H. et al., *Neuropathology of the Vegetative State After an Acute Brain Insult*, (2000) 1327-1338.
Adams, H. et al., *Diffuse Brain Damage of Immediate Impact Type. Its Relationship to "Primary Brain-Steam Damage" in Head Injury*. Brain 100 (1977) 489-502.
Alkire, M. T. et al., Consciousness and Anesthesia 322 (2008) 876-880.
Ammermann, H. et al., *MRI Brain Lesion Patterns in Patients in Anoxia-Induced Vegetative State*, Journal of the Neurological Sciences 260 (2007) 65-70.
Avidan, M. S. et al., *Prevention of Intraoperative Awareness in a High-Risk Surgical Population*, The New England Journal of Medicine, 365(7) (2011) 591-600.
Baars, B. J., *A Cognitive Theory of Consciousness*, M.U.P. Cambridge, ed.
Bandt, C. et al., *Permutation Entropy: A Natural Complexity Measure for Time Series*, Physical Review Letters 88 (2002) 174102.
Bekinschtein, T. et al., *Neural Signature of the Conscious Processing of Auditory Regularities*, Proceedings of the National Academy of Sciences of the United States of America, 106 (2009) 1672-7.

Bekinsten, T. et al., *Neural Signature of the Conscious Processing of Auditory Regularities*, Proceedings of the National Academy of Sciences USA 106 (2009) 1672-1677.
Benedetto, D. et al., *Language Trees and Zipping*, Physical Review Letters, 88(4) (2002) 048702.
Boly, M. et al., *Preserved Feedforward but Impaired Topdown Processes in the Vegetative State*, Science (new York, NY) 332 (2011) 858-62.
Boly, M. et al., *Auditory Processing in Severely Brain Injured Patients: Differerences Between the Minimally Conscious State and the Persistent Vegetative State*, Archives of Neurology 61 (2004) 233-8.
Boly, M. et al., *Functional Connectivity in the Default Network During Resting State is Preserved in a Vegetative but not in a Brain Dead Patient*, Human Brain Mapping 30 (2009) 2393-400.
Bruno, M.-A., et al., *Visual Fixation in the Vegetative State: An Observational Case Series PET Study*, BMC Neurology 10 (2010) 35.
Bruno, M. A. et al., *Multimodal Neuroimaging in Patients with Disorders of Consciousness Showing "Functional Hemispherectomy"*, Progress in Brain Research 193 (2011) 323-33.
Buckner, R. L. et al., *The Brain's Default Network: Anatomy, Function, and Relevance to Disease*, Annals of the New York Academy of Sciences 1124 (2008) 1-38.
Cao, Y. et al., *Detecting Dynamical Changes in Time Series Using the Permutation Entropy*, Physical Review E70 (2004) 046217.
Cauda, F. et al., *Disrupted Intrinsic Functional Connectivity in the Vegetative State*, Journal of Neurology, Neurosurgery, and Psychiatry 80 (2009) 429-31.
Chaitin, G., *The Berry Paradox*, Complex Systems and Bianary Networks (1995).
Chaitin, G., *Information-Theoretic Computation Complexity*, IEEE Transactions on Information Theory 20 (1974) 10-15.
Childs, N. L. et al., *Accuracy of Diagnosis of Persistent Vegetative State*, Neurology 43 (1993) 1465-7.
Crone, J. S. et al., *Deactivation of the Default Mode Network as a Marker of Impaired Consciousness: an fMRI Study*, PloS one 6 (2011) e26373.
Cruse, D. et al., *Bedside Detection of Awareness of Vegetative State: A Cohort Study*, Lancet 378 (2011) 2088-94.
Dehaene, S. et al., *Experimental and Theoretical Approaches to Conscious Processing*, Neuron 70, (2011) 200-227.
Del Cul, A. et al., *Brain Dynamics Underlying the Nonlinear Threshold for Access to Consciousness*, PLoS Biology 5 (2007) e260.
Dehaene, S. et al.,l *Conscious, Preconscious, and Subliminal Processing: A Testable Taxonomy*, Trends in Cognitive Sciences 10 (2006) 204-211.
Edelman, G. M., *The Remebered Present: A Biological Theory of Consciousness* (Basic Books) (1989).
Faugeras F. et al., *Probing Consciousness With Event-Related Potentials in the Vegetative State*, Neurology 77 (2011) 264-8.
Faugeras, F. et al., *Event Related Potentials Elicited by Violations of Auditory Regularities in Patients With Impaired Consciousness*, Neuropsychologia 50 (2012) 403-18.
Fellinger, R. et al., *Cognitive Processes in Disorders of Consciousness as Revealed by EEG Time-Frequency Analyses*, Clinical Neurophysiology 122 (2011) 2177-84.
Fernandez-Espejo, D. et al., *Diffusion Weighted Imaging Distinguishes the Vegetative State From the Minimally Conscious State*, NeuroImage 54 (2011) 103-12.
Ferrarelli, F. et al., *Breakdown in Cortical Effective Connectivity During Midazolam-Induced Loss of Consciousness*, Proceedings of the National Academy of Sciences of the United States of America 107 (2010) 2681-6.
Finelli, L. A. et al. *Functional Topography of the Human nonREM Sleep Electroencephalogram*, European Journal of Neuroscience 13 (2001) 2282-2290.
Fingelkurts, A. A. et al., *EGG Oscillatory States as Neuro-Phenomenology of Consciousness as Revealed From Patients in Vegetative and Minimally Conscious States*, Consciousness and Cognition 21 (2012) 146-69.

(56) References Cited

OTHER PUBLICATIONS

Fingelkurts, A. A. et al., *DMN Operational Synchrony Relates to Self-Consciousness: Evidence from Patients in Vegetative and Minimally Conscious States*, The Open Neuroimaging Journal 6 (2012) 55-68.

Fingelkurts, A. A. et al., *Toward Operational Architectonics of Consciousness: Basic Evidence From Patients with Severe Cerebral Injuries*, Cognitive Processing 13 (2011) 111-1312.

Fisch, L. et al., *Neural "Ignition": Enhanced Activation Linked to Perceptual Awareness in Human Ventral Stream Visual Cortex*, Neuron 64 (2009) 562-74.

Fischer, C. et al., *Predictive Value of Sensory and Cognitive Evoked Potentials for Awakening From Coma*, Neurology 63 (2004) 669-673.

Fischer, C. et al., *Event-Related Potentials (MMN and Novelty P3) in Permanent Vegetative or Minimally Conscious States*, Clinical Neurophysiology 121 (2010) 1032-42.

Fries, P. A., *A Mechanism for Cognitive Dynamics: Neuronal Communication Through Neuronal Coherence*, Trends in Cognitive Sciences 9 (2005) 474-80.

Gaillard, R. et al., *Converting Intracranial Markers of Conscious Access*, PLoS Biology 7 (2009) 1-21.

Galanaud, D. et al., *Assessment of White Matter Injury and Outcome in Severe Brain Trauma: A Prospective Multicenter Cohort*, Anethesiology 117 (2012) 1300-1310.

Garrett, D. D. et al., *Blood Oxygen Level-Dependent Signal Variability is More Than Just Noise*, The Journal of Neuroscience 30 (201) 4914-21.

Giacino, J. T. et al., *The JFK Coma Recovery Scale-Revised: Measurement Characteristics and Diagnostic Utility*, Archives of Physical Medicine and Rehabilitation, 85(12) (2004) 2020-2029.

Giacino, J. T. et al., *The Minimally Conscious State: Definition and Diagnostic Criteria*, Neurology 58 (2002) 349.

Giacino, J. T. et al., *Diagnostic and Prognostic Guidelines for the Vegetative and Minimally Conscious States*, Neuropsychological Rehabilitation 15 (2005) 166-74.

Gill, M. et al., *Can the Bispectral Index Monitor Quantify Altered Level of Consciousness in Emergency Department Patients?* Academic Emergency Medicine: Official Journal of the Society of Academic Emergency Medicine, 10(2) (2003) 175-9.

Goldfine, A. M. et al., *Determination of Awareness in Patients With Severe Brain Injury Using EEG Power Spectral Analysis*, Clinical Neurophysiology 122 (2011) 2157-68.

Gosseries, O. et al., *Automated EEG Entropy Measurements in Coma, Vegetative State/Unresponsive Wakefulness Syndrome and Minimally Conscious State*, Functional Neurology, 26(1) (2011) 25-30.

Graham, D. I. et al., *Neuropathology of the Vegetative State After Head Injury*, Neuropsychological Rehabilitation 15, 198-213.

Haynes, J.-D., *Multivariate Decoding and Brain Reading: Introduction to the Special Issue*, NeuroImage 56 (2011) 385-6.

Inouye, T. et al., *Quantification of EEG Irregularity by Use of the Entropy of the Power Spectrum*, Electroencephalography and Clinical Neurophysiology 79 (1991) 204-210.

Jordan, D. et al., *Electroencephalographic Order Pattern Analysis for the Separation of Consciousness and Unconsciousness: An Analysis of Approximate Entropy, Permutation Entropy, Recurrence Rate, and Phase Coupling of Order Recurrence Plots*, Anesthesiology 109, 1014-22 (2008).

Kampfl, A. et al., *The Persistent Vegetative State After Closed Head Injury: Clinical and Magnetic Resonance Imaging Findings in 42 Patients*, Journal of Neurosurgery 88 (1998) 809-16.

Kayser, J. et al., *Principal Components Analysis of Laplacian Waveforms as a Generic Method for Identifying ERP Generator Patterns: II. Adequacy of Low Density Estimates*, Clinical Neurophysiology 117 (2006) 369-80.

King, J.-R. et al., *Comment on "Preserved Feedforward but Impaired Top-Down Processes in the Vegetative State"*, Science (New York, NY) 334 (2011) 1203.

Knerr, S. et al., *Single-Layer Learning Revisited: A Stepwise Procedure for Builidng and Training a Neural Network*, Neurocomputing: Algorithms, Architectures and Applications (1990).

Kolmogorov, A., *Three Appraches to the Quantitative Definition of Information*, Problems of Information Transmission 1 (1965) 1-7.

Kotchouby, B. et al., *Information Processing in Severe Disorders of Consiousness: Vegetative State and Minimally Conscious State*, Clinical Neurophysiology 116 (2005) 2441-53.

Lachaux, J. P. et al., *Measuring Phase Synchrony in Brain Signals*, Human Brain Mapping 8 (1999) 194-208.

Lambert, I. et al., *Alteration of Global Workspace During Loss of Consciousness: A Study of Parietal Seizures*, Epilepsia 53 (2012 ) 2104-10.

Lamme, V. A. F. et al., *The Distinct Modes of Vision Offered by Feedforward and Recurrent Processing*, Trends in Neurosciences 23 (2000) 571-579.

Lamme, V. A. F., *How Neuroscience Will Change Our View on Consciousness*, Cognitive Neuroscience 1 (2010) 204-220.

Lau, H., *A Higher Order Bayesian Decision Theory of Consciousness*, Progress in Brain Research 168 (2008) 35-48.

Laureys, S. et al., *Coma Consciousness: Paradigms (Re)framed by Neuroimaging*, NeuroImage, 61(2), (2012) 478-91.

Laureys, S. et al., *Restoration of Thalamocortical Connectivity After Recovery From Persistent Vegetative State*, Lancet 355 (2000) 1790-1.

Laureys, S. et al., *Impaired Effective Cortical Connectivity in Vegetative State Preliminary Investigation Using PET*, NeuroImage 9 (1999) 377-82.

Laureys, S. et al., *Residual Cognitive Function in Comatose, Vegetative and Minimally Conscious States*, Current Opinion in Neurology 18 (2005) 726-33.

Lee, U. et al., *Propofol Induction Reduces the Capacity for Neural Information Integration: Implications for the Mechanism of Consciousness and General Anesthesia*, Consciousness and Cognition 18 (2009) 56-64.

Lehembre, R. et al., *Resting-State EEG Study of Comatose Patients: A Connectivity and Frequency Analysis to Find Differences Between Vegetative and Minimally Conscious States*, Functional Neurology 27 (2012) 41-7.

Lempel, A. et al., *On the Complexity of Finite Sequences*, IEEE Transactions on Information Theory 22 (1976) 75-81.

Li, X. et al., *Using Permutation Entropy to Measure the Electroencephalographic Effects of Sevoflurane*, Anesthesiology.

MacKay, D. J. C., *Information Theory, Inference and Learning Algorithms*, Cambridge University Press, 640 (2003).

Massimini, M. et al., *Breakdown of Cortical Effective Connectivity During Sleep*, Science 309 (2005) 2228-32.

Melloni, L. et al., *Expectations Change the Signatures and Timing of Electrophysiological Correlates of Perceptual Awareness*, The Journal of Neuroscience 31 (2011) 1386-96.

Meyer, K. et al., *Convergence and Divergence in a Neural Architecture for Recognition and Memory*, Trends in Neurosciences 32 (2009) 376-82.

Monti, M. M. et al., *Willful Modulation of Brain Activity in Disorders of Consciousness*, New England Journal of Medicine 362 (2010) 579-589.

Naccache, L. et al., *Auditory Mismatch Negativity is a Good Predictor of Awakening in Comatose Patients: A Fast and Reliable Procedure*, Clinical Neurophysiology 116 (2005) 988-9.

Nashida, T. et al., *Automatic Auditory Information Processing in Sleep*, Sleep 23 (2000) 821-828.

Newcombe, V. F. J. et al., *Aetiological Differences in Neuroanatomy of the Vegetative State: Insights From Diffusion Tensor Imaging and Functional Implications*, Journal of Neurology, Neurosurgery, and Psychiatry 81 (2010) 552-61.

Northoff, G., *What the Brain's Intrinsic Activity Can Tell Us About Consciousness? A Tridimensional View*, (2012) Neuroscience and Biobehavioral Reviews.

Ogashiwa, M. et al., *Clinicopathological Studies of the Vegetative State: Distinction Between the Vegetative State and Brain Death*, Brain and Nerve 28 (1976) 901-12.

Owen, A. M. et al., *Detecting Awareness in the Vegetative State*, Science, 313 (5792) (2006), 1402.

(56) References Cited

OTHER PUBLICATIONS

Parvizi, J. et al., *Neuroanatomical Correlates of Brainstem Coma*, Brain 126 (2003) 1524-36.
Parvizi, J. et al., *Neural Connections of the Posteromedial Cortex in the Macaque*, Proceedings of the National Academy of Sciences of the United States of America 103 (2006) 1563-8.
Pedregosa, F. et al.l, *Scikit-Learn: Machine Learning in Python*, The Journal of Machine Learning Research 12 (2011) 2825-2830.
Platt, J. C., *Probabilistic Outputs for Support Vector Machines and Comparisons to Regularized Likelihood Methods*, Advances in Large Margin Classifiers 10 (1999) 61-174.
Posner, J. B. et al., Posner's Diagnosis of Stupor and Coma 71 (2007).
Rampil, I. J., *A Primer for EEG Signal Processing in Anethesia*, Anesthesiology 89 (1998) 980-1002.
Rees, G. et al., *Neural Correlates of Consciousness in Humans*, Nature Reviews, Neuroscience 3 (2002) 261-70.
Reza, H. et al., *Common Fronto-Parietal Activity in Attention, Memory, and Consciousness: Shared Demands on Integration?*, Consciousness and Cognition 14 (2005) 39-425.
Rohaut, B. et al., *Prédiction du réveil et détection de la conscience: intérêt des potentiels évoqués cognitifs*, Réanimation 18 (2009) 659-663.
Rosanova, M. et al., *Recovery of Cortical Effective Connectivity and Recovery of Consciousness in Vegetative Patients*, Brain: A Journal of Neurology 135 (2012) 1308-20.
Schiff, N. D. et al., *Residual Cerebral Activity and Behavioural Fragments Can Remain in the Persistently Vegetative Brain*, Brain 125 (2002) 1210-34.
Schnakers, C. et al., *Diagnostic Accuracy of the Vegetative and Minimally Conscious State: Clinical Concensus Versus Standardized Neurobehavioral Assessment*, BMC Neurology (2009) 9, 35.
Schnakers, C. et al., *Diagnostic and Prognostic Use of Bispectral Index in Coma, Vegetative State and Related Disorders*, Brain Injury, 22(12) (2008) 926-31.
Schnakers, C. et al., *Detecting Consciousness in a Total Locked-In Syndrome: An Active Event-Related Paradigm*, Neurocase 15 (2009) 271-7.
Schnakers, C. et al., *A French Validation Study of the Coma Recovery Scale-Revised (CRS-R)*, Brain Injury 22 (2008) 786-92.
Schurger, A. et al., *Reproducibility Distinguishes Conscious From Nonconscious Neural Representations*, Science 327 (2010) 97-9.
Sebel, P. S. et al., *The Icidence of Awareness During Anesthesia: A Multicenter United State Study*, Anesthesia and Analgesia, 99(3), (2004) 833-9.
Sergent, C. et al., *Timing of the Brain Events Underlying Access to Consciousness During the Attentional Blink*, Nature Neuroscience 8 (2005) 1391-400.
Seth, A. K. et al., *Causal Density and Integrated Inforamtion as Measures of Conscious Level*, Philosophical Transations, Series A, Mathematical, Physical, and Engineering Sciences 369 (2011) 3748-67.
Shaw, F. Z. et al., *Algorithmic Complexity as an Index of Cortical Function in Awake and Pentobarbital-anesthetized Rats*, Journal of Neuroscience Methods 93 (1999) 101-10.
Silva, S. et al., *Wakefulness and Loss of Awareness: Brain and Brainstem Interaction in the Vegetative State*, Neurology 74 (2010) 313-20.
Soddu, A. et al., *Identifying the Default-Mode Component in Spatial IC Analyses of Patients with Disorders of Consciousness*, Human Brain Mapping 33 (2012) 778-96.
Salomon, D., Data Compression: The Complete Reference, vol. 10, Springer-Verlag (2007).
Stam, C. J. et al., *Phase Lag Index: Assessment of Functional Connectivity From Multi Channel EEG and MEG with Diminished Bias From Common Sources*, Human Brain Mapping 28 (2007) 1178-93.
Stam, C. J., *Nonlinear Dynamical Analysis of EEG and MEG: Review of an Emerging Field*, Clinical Neurophysiology 116 (2005) 2266-301.
Staniek, M. et al., *Symbolic Transfer Entropy*, Physical Review Lettes, 100(15) (2008) 1-4.
Supp, G. G. et al., *Cortical Hypersynchrony Predicts Breakdown of Sensory Processing During Loss of Consciousness*, Current Biology: CB21 (2011) 1988-93.
Tononi, G. et al., *A Measure for Brain Complexity: Relating Functinoal Segregation and Integration in the Nervous System*, Proceedings of the National Academy of Sciences of the United States of America 91 (1994) 5033-7.
Tononi, G. et al., *Measuring Information Integration*, BMC Neuroscience 4 (2003) 31.
Tononi, G., *An Information Integration Theory of Consciousness*, BMC Neuroscience 5 (2004) 42.
Tononi, G., *Consicousness as Integrated Information: A Provisional Manifesto*, Biol. Bull 215 (2008) 216-242.
Tononi, G. et al., *Consciousness and Complexity*, Science 282 (New York, NY) 1846.
Tononi, G. et al., *The Neural Correlates of Consciousness: an Update*, Annals of the New York Academy of Sciences 1124 (2008) 239-61.
Vakkuri, A. et al., *Time-Frequency Balanced Spectral Entropy as a Measure of Anesthetic Drug Effect in Central Nervous Systrem During Sevoflurane, Propofol, and Thiopental Anesthesia*, Acta Anesthesiologica Scandinavica 48 (2004) 145-153.
Vanhaudenhuyse, A. et al., *Default Network Connectivity Reflects the Level of Consciousness in Non-Communicative Brain-Damaged Patients*, Brain 133 (2010) 161-71.
Viertio-Oja, H. et al., *Description of the Entropy Algorithm as Applied in the Datex-Ohmeda S/5 Entropy Module*, Acta Anaesthesiologica Scandinavica, 48(2) (2004) 154-61.
Vogt, F. et al., *High-Frequency Components in the Alpha Band and Memory Performance*, Journal of Clinical Neurophysiology 15 (1998) 167-72.
Wagner, A. D. et al., *Parietal Lobe Contributions to Episodic Memory Retrieval*, Trends in Cognitive Sciences 9 (2005) 44.
Walter, W. G. et al., *Contingent Negative Variation: An Electric Sign of Sensori-Motor Association and Expectancy in the Human Brain*, Nature 203 (1964) 380-384.
Wijnen, V. J. M. et al., *Mismatch Negativity Predicts Recovery From the Vegetative State*, Clinical Neurophysiology 118 (2007) 597-605.
Zhou, J. et al., *Specific and Nonspecific Thalamocortical Functional Connectivity in Normal and Vegetative States*, Consciousness and Cognition 20 (2011) 257-68.

\* cited by examiner a.
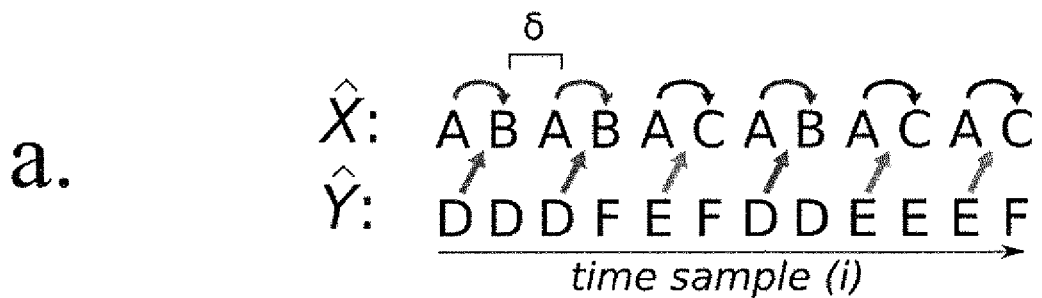
b.
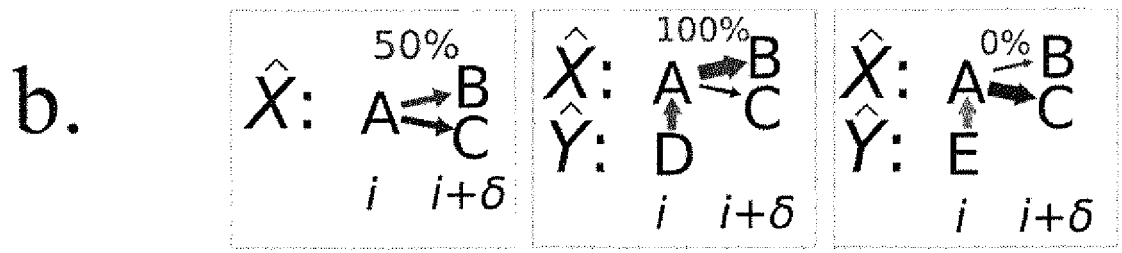
c. $STE_{\hat{Y},\hat{X}} = \sum p(\hat{x}_{i+\delta}, \hat{x}_i, \hat{y}_i) \log \frac{p(\hat{x}_{i+\delta}|\hat{x}_i, \hat{y}_i)}{p(\hat{x}_{i+\delta}|\hat{x}_i)}$
Figure 1

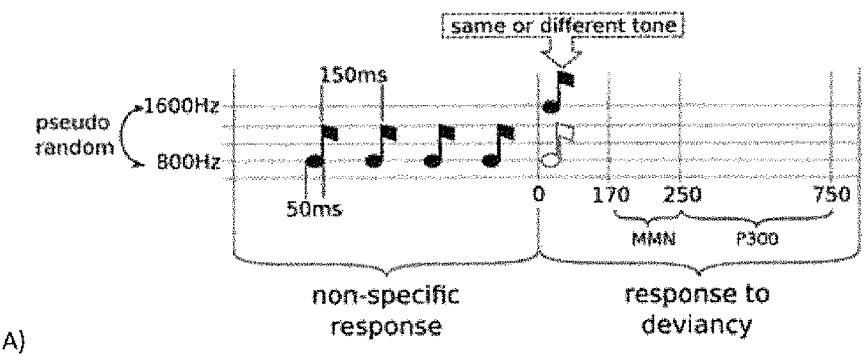

A)

Measures

| Event-related potentials | | Ongoing activity | | | |
| --- | --- | --- | --- | --- | --- |
| | | Single electrode | | Across electrodes | |
| Early components | Late components | Spectrum | Information theory | Spectrum | Information theory |
| P1 | P3a | Power in frequency bands | Permutation entropy | Phase locking value | Symbolic mutual information |
| MMN | P3b | Spectral summaries | Kolmogorov complexity | Phase locking index | Global Kolmogorov complexity |
| CNV | | Spectral entropy | | | |

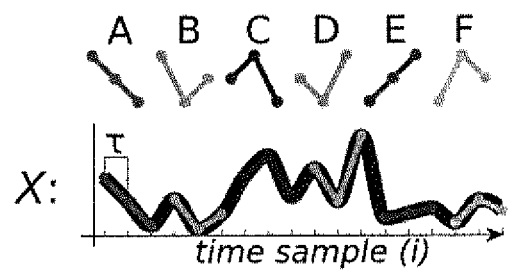
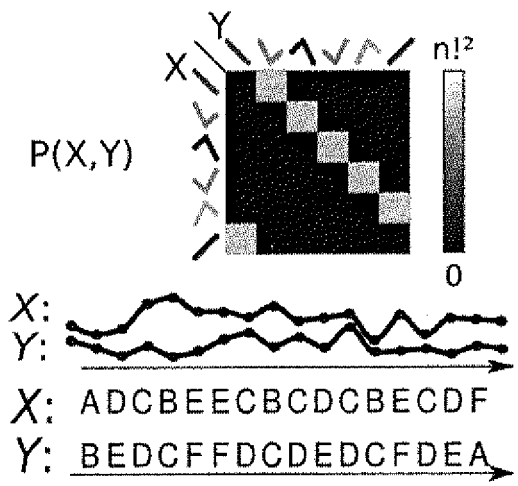
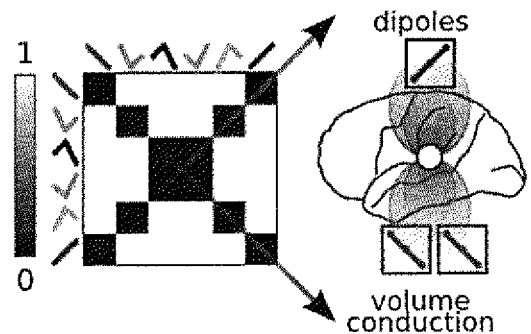
Figure 17

METHODS TO MONITOR CONSCIOUSNESS

FIELD

The present invention relates to methods to measure and monitor consciousness in a subject and involves the assessment of EEG or an equivalent data set by assessing the sharing of information between different parts of the brain using symbolic mutual information (SMI) and/or by assessing the complexity of the brain signals using Kolmogorov symbolic complexity (KSC) and determining a consciousness index (CI) for the subject on the basis of this assessment. The present invention also relates to methods to measure and monitor consciousness in a subject and involves the assessment of EEG or an equivalent data set; using a strategy of combining one or both of these measures as well as additional indices and generating a consciousness index (CI) for the subject on the basis of the combined results of the various assessments. The present invention also relates to methods and apparatus to monitor the consciousness of a subject and to administer cognitive or another form of stimulation and/or medication to the subject on the basis of their level of consciousness or alterations therein.

BACKGROUND

Developing a test capable of detecting conscious is an important and ongoing area of research and further insights into the basis of consciousness are of general interest, but such a test is essential in two cases: for patients with Disorders of Consciousness (DOC) and for subjects undergoing general anesthesia.

Many patients cannot communicate explicitly and are described with clinical labels such as coma, vegetative state, minimally conscious state, and locked-in state, this general class of condition being classified as Disorders of Consciousness. A distinction has been introduced between the vegetative state (VS) and the minimally conscious state (MCS). Both exhibit similarly preserved arousal, but MCS patients show signs of intentional behavior while VS patients remain utterly unresponsive. The clinical distinction between these two states is very difficult. It has been reported that up to 43% of patients are erroneously diagnosed as VS (1). Unfortunately, even in the case of patients assessed by specially trained neurologists, science and modern medicine remain hard-pressed to decide whether a patient diagnosed as VS could still be conscious but unable to communicate (2,3).

For subjects undergoing general anesthesia, although infrequent, consciousness during a surgical procedure has been reported and can lead to surgical complications and even led to post-traumatic stress disorders (PTSD). It has been reported that this phenomena occurs at a rate of 2-3 cases per 1000 patients (4). In France there are approximately 4 million surgeries under general anesthetic per year and therefore it would be expected that around 10000 instances of intraoperative consciousness occur every year in this country alone.

Currently no reliable method has been developed to routinely identify consciousness in a subject in spite of intense experimental and theoretical efforts. This is in part due to continued uncertainty as to the precise neural signatures of conscious processing. Similarly, from a cognitive psychology perspective, it has proven difficult to identify operations unique to the conscious brain (5).

Several approaches have been attempted in the art, with varying degrees of success. For instance, Owen and collaborators have shown that functional MRI could detect consciousness in some VS patients (3) and, in one case, restore some communication (7). Similar results may be obtained using scalp electroencephalography (EEG), a more economical and practical technique that can be easily applied at the bedside (8-10).

Specifically concerning the detection of unexpected consciousness in anaesthetized patients there are two principal commercial EEG anesthesia monitors available:

1) The Bispectral index (BIS) from Aspect Medical Systems, Inc., USA and Covidien plc, Ireland.
2) The "Entropy Module" from GE Healthcare, USA (11).

These two systems have also been tested in DOC patients. The bispectral index showed contradictory reports: while Gill et at. showed that it does not reliably correlate with the patients conscious state (12), Schnakers et. al. reported statistically significant differences (p<0.05) between the VS and MCS patients (13).

In a recent study Avidan et al. (14) showed that BIS monitoring might not be better to prevent intraoperative awareness than standard monitoring of end-tidal anesthetic-agent concentration (ETAC). The study reported a total of 7 of 2861 patients with intraoperative awareness in the BIS group compared to 2/2852 in the ETAC group.

Gosseries et al. tested the Datex-Ohmeda S/5 entropy monitoring system and their study showed that entropy could reliably discriminate VS from MCS but only in the acute phase (15).

In DOC patients the need for a system that automatically detects consciousness is mostly relevant in the boundary between the VS and the MCS state. In standard clinical practice, the behavioral classification between these conditions is done using the Coma Recovery Scale Revised (CRS-R) (16). On this scale the boundary between the groups corresponds to a CRS-R equal to 9. In both the Gosseries and Schnakers studies the VS and MCS populations had CRS-R scores distant to that boundary (VS=4±1; MCS=11±3) making the comparison less relevant. Efficiency invariance to the delay post-injury is also very relevant. Both studies showed discrimination efficiency only for acute cases.

A further method to monitor consciousness under anesthesia has been developed which is based on symbolic transfer entropy (WO2012/150015). This method, originally introduced by Staniek et al. quantifies the directionality of the information transfer between signals (17). In simple terms this method looks for the transmission of information, as indexed by a given set of electrical signals, from one portion of the subject's brain to a second, the detection of this directional transmission of information being taken by the proposed system as an indication of consciousness. Although as good as existing methods, it is not clear that this approach is superior to those which already exist. As detailed in the present Patent Application below, the inventors have proven that this earlier method (based on directional symbolic transfer entropy) to able to discriminate between VS from MCS patients less well that the methods proposed in the present Patent Application.

No reliable method or apparatus yet exists which routinely allows the detection of residual consciousness and especially the differential diagnosis of a VS and MCS subjects.

SUMMARY

The inventors have now proposed and tested a new approach to measuring consciousness in a subject, comprising analyzing brain activity with symbolic mutual information (SMI) and/or Kolgomorov symbolic complexity (KSC).

This new test allows the differentiation of MCS and VS subjects, as well as the deteunination of unwanted consciousness in a normal subject undergoing anesthesia.

In particular the brain activity is measured using a technique selected from the group comprising: electroencephalography (EEG), Magneto-encephalography (MEG), electro-corticography (ECOG), intracranial local field potentials (LFPs), functional magnetic resonance imaging (fMRI) and functional near-infrared imaging (fNIRS).

In accordance with the present invention when brain activity is measured using EEG at least 2 electrodes are used (plus a reference site electrode), in further embodiments up to 256 or more electrodes may be used.

In the context of the present invention the measurement of brain activity when made using EEG, in its simplest form, measures the difference in electrical potential between the electrodes and a further reference point/electrode.

In accordance with a further aspect of the present invention the recorded brain activity undergoes pre-processing. In such pre-processing artifacts, such as movement artifacts, are removed and the recorded signal is bandpass filtered (typically with cutoff frequencies of 0.5 Hz and 30 Hz).

In accordance with a further aspect of the present invention the recorded brain activity undergoes Symbolic Transformation or an equivalent mathematical mapping. The brain activity signals are transformed to a series of discrete symbols using the same principles as in (Bandt & Pompe, 2002) or an equivalent mathematical mapping. The main advantages of this method are (1) the possible identification of nonlinear patterns in the signal (2) the reduction of the problem space to a limited set of discrete symbols and (3) its robustness to noise. The transformation is performed by first extracting sub-vectors of the signal recorded from a given sensor, each comprising n measures separated by a fixed time delay ($\tau$). The parameter $\tau$ thus determines the broad frequency range to which the symbolic transform is sensitive. Each sub-vector is then assigned a unique symbol, depending only on the order of its amplitudes. For a given symbol size (n) there are n! possible orderings and thus equal amount of possible symbols. In actual brain recordings, symbols may not be equiprobable, and their distribution may not be random either over time or over the different sensor locations. The method evaluates these deviations from pure randomness.

In accordance with the present invention the sharing of information across different brain areas is analyzed using weighted symbolic mutual infoiniation (wSMI).

In accordance with this aspect of the present invention, a non-directional estimate of the coupling between two EEG recordings is obtained by computing the weighted mutual information between time series corresponding to the two electrodes sites. This is achieved by computing the weighted mutual information between each pair of electrodes after firstly transforming the brain activity using symbolic transformation. A key aspect of the invention and which distinguishes it from classical Mutual Information approaches and makes it more sensitive to consciousness, is that the different combinations of symbols x and y are assigned a weight w(x,y) which can range from zero to one. The inventors refer to this measure as weighted Symbolic Mutual Information (wSMI) and it is estimated as follows:

$$wSMI = \sum_{x \in X} \sum_{y \in Y} w(x, y) p(x, y) \log \frac{p(x, y)}{p(x)p(y)}$$

where x and y are all symbols present in signals X and Y respectively; p(x,y) is the joint probability of co-occurrence of symbol x in signal X and symbol y in signal Y; and p(x) and p(y) are the probabilities of those symbols in each respective signal. Finally, w(x,y) is a weight matrix. The weight matrix can be optimized to be most sensitive to the types of symbol correlations that characterize consciousness. In particular, the weights can be used to reduce the impact of a trivial coupling such as when x and y are the same symbol or when are mirror symbols (same symbol after sign change). By reducing the weight w(x,y) for such pairings, and letting the rest of the elements of w(x,y) equal to one, the inventors can reduce the impact of the contribution of common brain sources to the two recorded signals X and Y, and ensure that the wSMI measure gives a more accurate estimation of true information sharing between two regions of interest, which is thought to reflect consciousness.

Algorithmic information theory has been introduced by Andrey Kolmogorov and Gregory Chaitin as an area of interaction between computer science and information theory. The concept of algorithmic complexity or Kolmogorov-Chaitin complexity (K) is defined as the shortest description of a string (or in this case a time series). That is to say, K is the size of the smallest algorithm (or computer program) that can produce that particular time series. Unfortunately, it can be demonstrated by reductio ad absurdum that there is no possible algorithm that can measure K (Chaitin, 1995). To sidestep this issue, the inventors estimated an upper-bound value of K(X). This can be concretely realized by applying a lossless compression of the time series and quantifying the compression size. Capitalizing on the vast signal compression literature, the inventors heuristically used classical open-source compressors (gzip and bzip2) (109) to estimate K(X). Following the same logic as for wSMI, the inventors computed the complexity from the symbolic transformed series, the inventors call this measure: Kolgomorov Symbolic Complexity (KSC). To compute it, the symbolic series are compressed and KSC(x) is calculated as the size of the compressed string divided by the size of the original string. The premise is that, the bigger the size of the compressed string the more complex the structure of the time series, thus potentially indexing the local neural processing captured by that sensor.

In accordance with this aspect of the present invention therefore the method to measure consciousness in a subject may use Kolmogorov-Chaitin complexity or following transformation of the brain activity data set as indicated above, Kolgomorov Symbolic Complexity so as generate a measurement or monitor consciousness in a subject.

In accordance with a further aspect of the present invention, a number of further analyses maybe performed upon the brain activity, selected from the group comprising:

Event-Related Potentials (ERPs) such as Mid-latency auditory potential corresponding to the first sound (P1); Contingent Negative Variation (CNV); P3a; P3b; Mismatch negativity ($\Delta$MMN), Contrasted P3a ($\Delta$P3a) and contrasted P3b ($\Delta$P3b);

Time frequency analysis such as power quantification in different spectral bands;

Spectral summaries such as Power spectrum centroids {i.e., medium spectral frequency (MSF), spectral edge frequency (SEF)} and Spectral entropy (SE);

Signal complexity such as Permutation entropy; Kolmogorov Chaitin complexity;

Information sharing (across electrodes) such as Phase Locking Value (PLV); Phase Lag Index (PLI); Global algorithmic complexity (GK);

In accordance with another aspect of the present invention, following the analysis of the brain activity according to wSMI, KSC and/or any of the above indices, a consciousness index (CI) is produced. The optimal measure or combination of measures leading to CI is determined using machine learning techniques (including support vector machines and/or neural networks and/or regression). As explained below the combination of these various measures using this approach successfully enhances the discrimination power in a study of patients with disorders of consciousness.

In accordance with a preferred embodiment of the present invention a support vector machine is used to analyze the various data and predict which group the subject belongs to.

In accordance with a preferred embodiment of the present invention therefore there is provided a method to measure or monitor consciousness in a subject comprising the steps:

a) Acquisition of EEG signals via an array of at least 2 electrodes (and a reference) positioned upon a subjects head;
b) Pre-processing of the EEG signals of step a);
c) Symbolic transformation of the signals from step b);
d) Analysis of the signal from step c) using at least wSMI and/or KSC.
e) Calculation of a consciousness index.

In accordance with a further aspect of the present invention there is provided a system to automatically stimulate a patient according to the real-time output of the consciousness index calculated according to the present invention.

Such a system would be used to attempt to influence the transitions across states of consciousness, and possibly enhance the recovery of a stable conscious state, by delivering to patients cognitive or other suitable stimulus (e.g.: a familiar voice uttering the patient's name), specifically during periods in which the consciousness index reaches a critical value or target window, as revealed by electrophysiological markers. This positive reinforcement approach may help to speed up significantly consciousness recovery in patients with long-lasting fluctuations and slow emergences from the vegetative state. Alternatively modes of stimulation could involve: pharmacological or transcranial electromagnetic stimulation.

For a better understanding of the invention and to show how the same may be carried into effect, there will now be shown by way of example only, specific embodiments, methods and processes according to the present invention with reference to the accompanying drawings in which:

BRIEF DESCRIPTION OF THE DRAWINGS

FIG. 1. Symbolic Transfer Entropy (STE) quantifies the amount of information transferred from one signal to another, as the divergence of transitional probabilities in a given signal when the information from a second signal is available. In the present example (a), when signal X is in state A, it is either followed by B or by C. Based on knowledge of signal X alone, the transitions Ai→Bi+δ and Ai→Ci+δ appear random (b). However, one can note that the Ai→Bi+δ transition only occurs when signal Y at time i is in state D, and the Ai→Ci+δ transition only when signal Y is in state E at time i. Thus, the state of Y at time i adds information about the future (i+δ) of X. This information transfer is formalized in equation (c).

(a) Directional connectivity analyses are represented by two 1-dimensional graphs, each organizing 13 scalp regions of interest along the antero-posterior axis. These two 1D topographies respectively represent the source (predictor) and the destination (predicted) of information transfer. Results are also separately depicted for ipsilateral connections, contralateral connections, and midline regions. (b) ΔSTE for each group is summarized using similar 2×1D topographies. Regression analyses across the four states of consciousness demonstrate that the balance of information flow (ΔSTE) from centroposterior regions was positively correlated with the state of consciousness.

Figure 3:
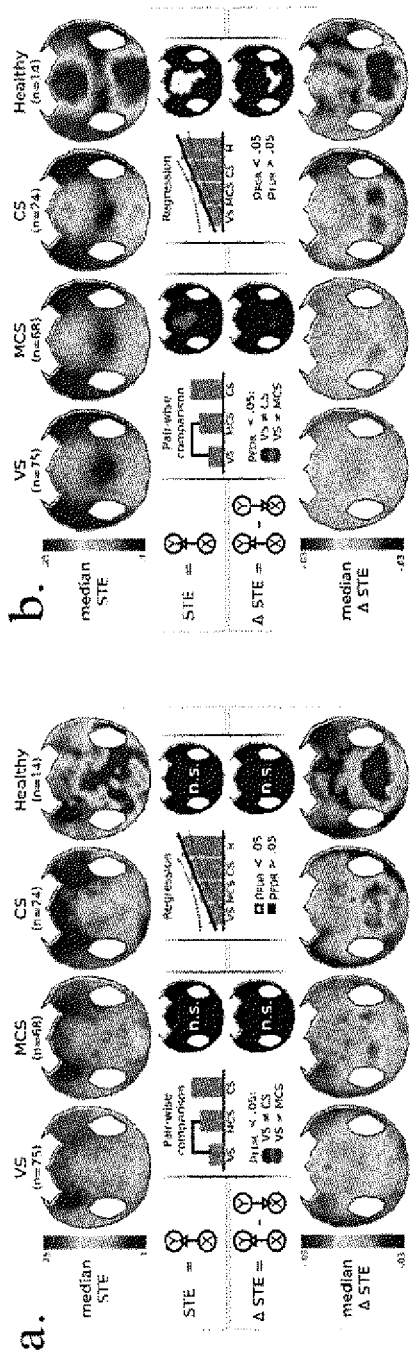

FIG. 3. Median STE and ΔSTE at each CSD site and each electrode.

(a) Current-Source Density (CSD) Topographies summarize STE (top) and ΔSTE (bottom) changes across states of consciousness. Despite an apparent trend, statistical analyses reveal no significant mean differences across groups.

(b) Similar graphs are plotted for (non-CSD) EEG Topographies. Regression analyses reveal an overall increase of frontal EEG channels' STE. Pair-wise comparisons confirm this effect by revealing that frontal EEG channel present a significantly lower STE in unconscious (VS) subjects. A similar trend was also visible across posterior channels, but did not resist correction for multiple comparisons (FDR). ΔSTE analyses suggest that the balance of information flow is positively increased with conscious states over centroposterior regions.

Figure 4:
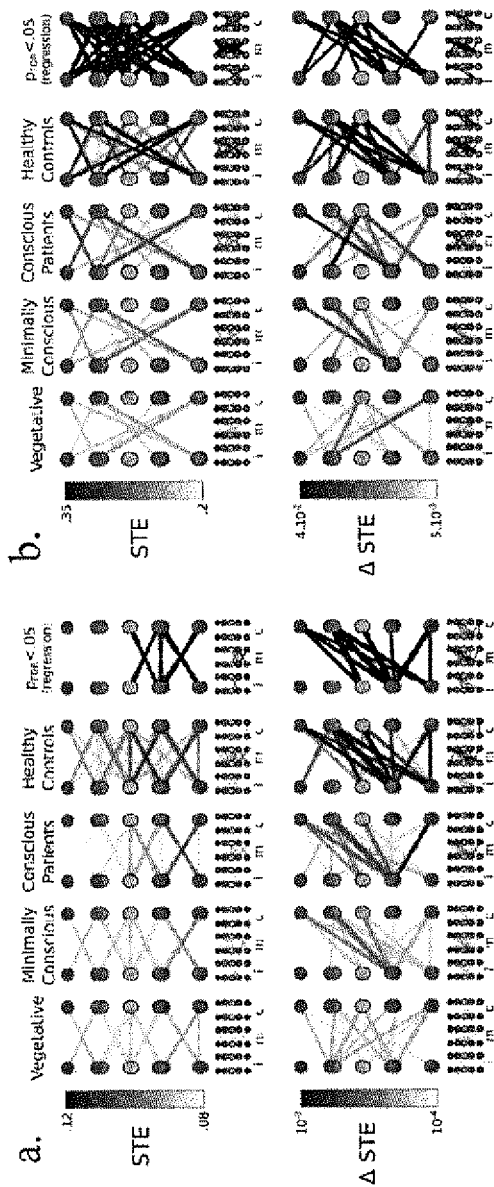

FIG. 4. STE and ΔSTE for each pairs of CSD and EEG clusters. (Supplement of FIG. 2)

STE (top) and ΔSTE (bottom) for each group is summarized using 2×1D topographies based on the same representation code as FIG. 6. (a) Directional connectivity analyses applied to CSD signals only revealed a small trend across states of consciousness: information transfers from and to centroposterior areas were positively associated with consciousness. ΔSTE results are identical to FIG. 6.

(b) Similar analyses were applied between (non-CSD) EEG channels. The results confirm that consciousness is associated with an overall increase of bidirectional information transfers across scalp regions. ΔSTE analyses revealed similar patterns for EEG and CSD data.

Figure 5:
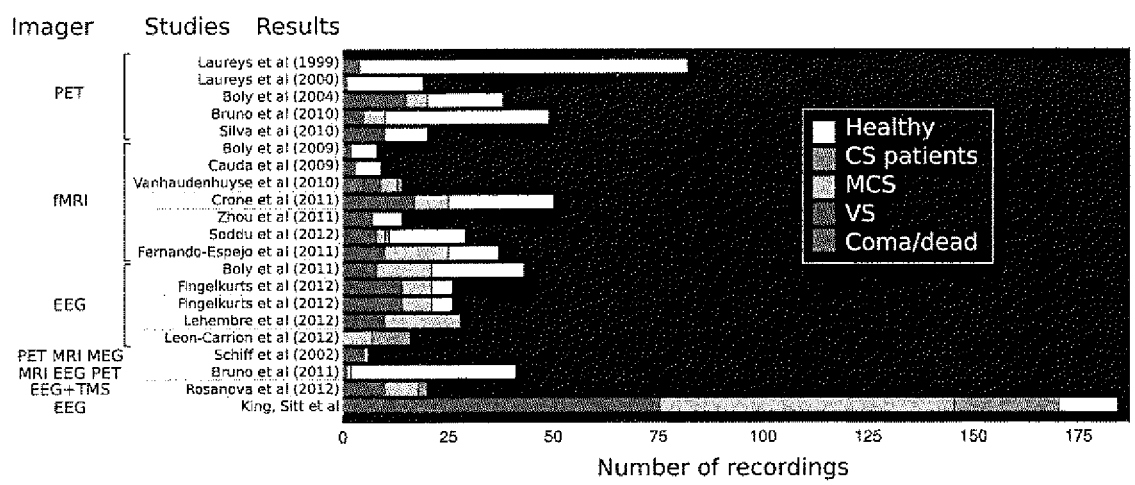

FIG. 5. Review of functional connectivity studies in DOC patients.

The number of patients recorded with different apparatus is summarized for most studies investigating functional connectivity in DOC patients. The present study gathers a unique cohort of VS and MCS patients suffering from different etiologies and levels of acuteness.

FIG. 6. A multi-dimensional approach to categorize states of consciousness. (A) Paradigm used for patient stimulation. Spectral and information-theory measures were computed in the non-specific response window, while event-related potentials (ERPs) were computed on the later window. (B) Taxonomy of EEG-derived measures used to categorize states of consciousness. Measures can be conceptually organized along several dimensions: First, the inventors distinguish measures of stimulus processing (event-related potentials (ERPs), further subdivided into early versus late components) from measures of ongoing activity. The latter are classified according to the theoretical background used to derive the measure: (1) Spectral (Fourier frequency analysis) or Information Theory; (2) Local dynamics or connectivity: some measures are computed within each electrode, while others index the interactions between electrodes; and (3) average parameter value or fluctuation across trials: the inventors study either the mean ($\mu$) or standard deviation ($\sigma$) of a measure across trials.

Figure 7:
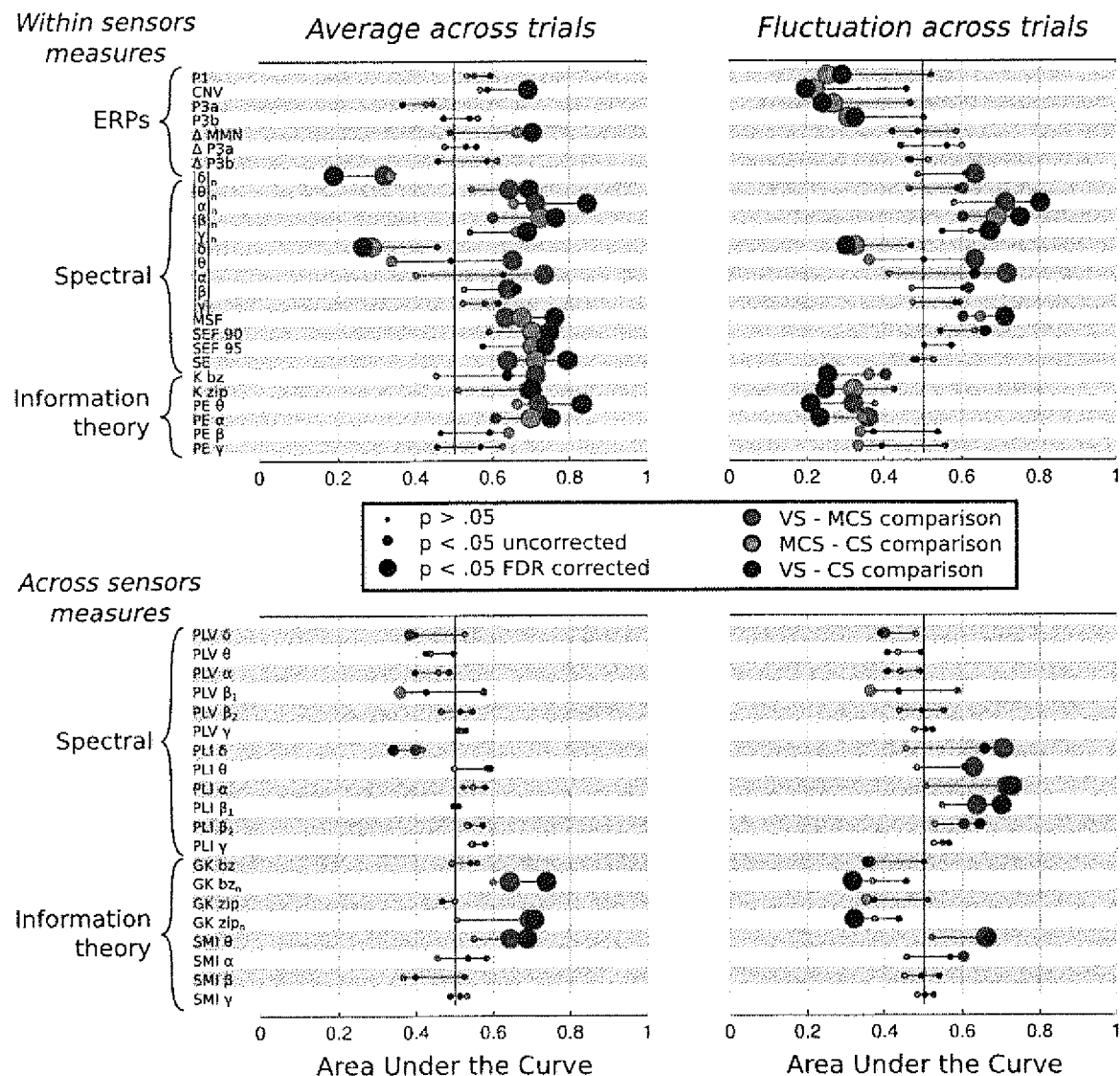

FIG. 7. Discrimination power for all measures. Each line provides a summary report of one measure. The measures are ordered according to the taxonomy presented in FIG. 6. The location of each dot corresponds to the area under the curve (AUC) for a pairwise comparison of two states of consciousness (see Methods). Chance level corresponds to AUC=50% (central vertical line). If AUC is bigger than 50%, it means that the corresponding measure tends to increase in parallel to the state of consciousness (from VS to MCS and CS). If AUC is smaller than 50%, it means that the corresponding measure tends to decrease when states of consciousness increases. Dot shade and size indicate the type and significance of the comparison (see legend in the middle panel). The red color is the most relevant since it indicates a significant difference between the VS and MCS states of consciousness.

Figure 8:
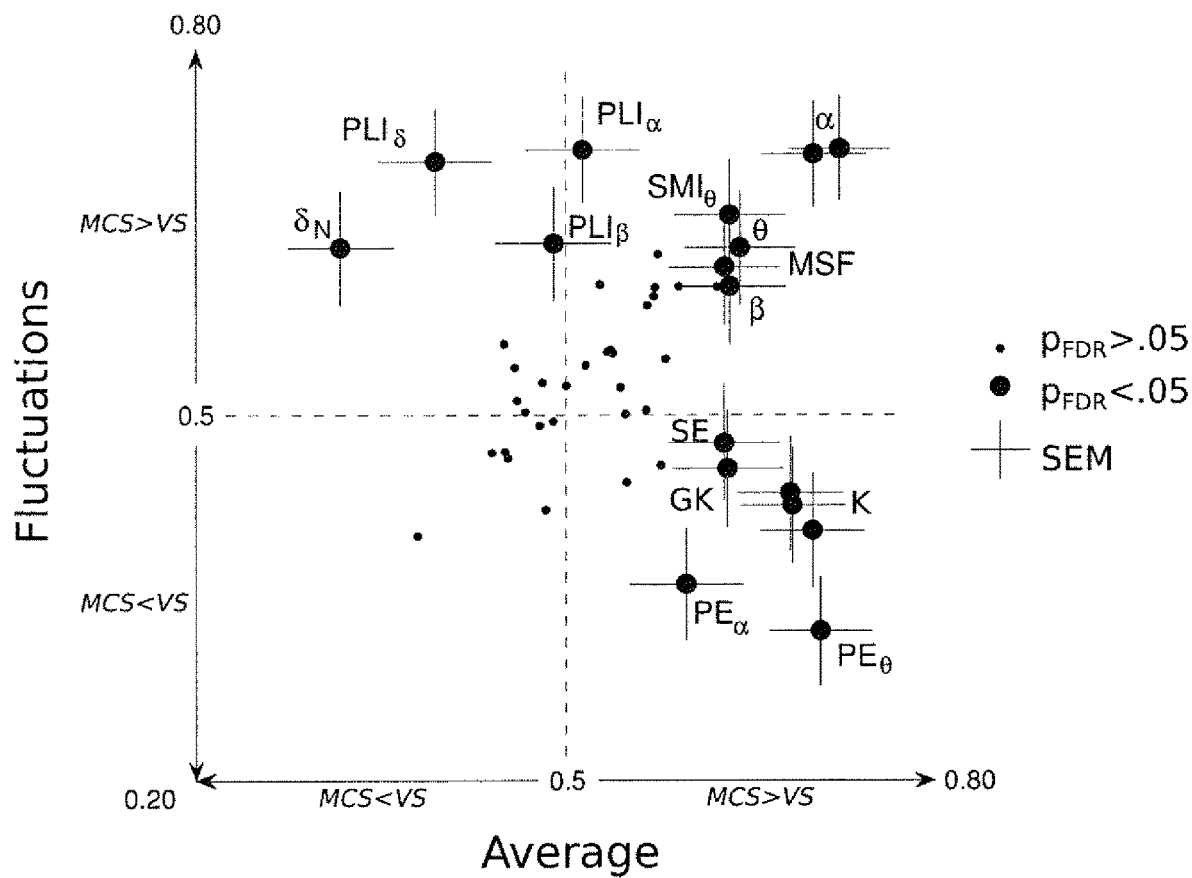

FIG. 8. Summary of the measures that discriminate the VS and MCS states of consciousness. In this diagram, each measure is placed at coordinates that reflect its power in discriminating MCS from VS recordings (area under the curve, AUC). The x axis indicates discriminatory power for the average of this measure over trials, while the y axis indicates discriminatory power for its fluctuations across trials. For instance, the Kolmogorov complexity (K) measure appears in the bottom right quadrant, which means that its average value is significantly higher in MCS than in VS, while its standard deviation, conversely, is higher in VS than in MCS. Measures marked in bold were significant ($p_{FDR}<0.05$). Non-significant measures are indicated with dots.

Figure 9:
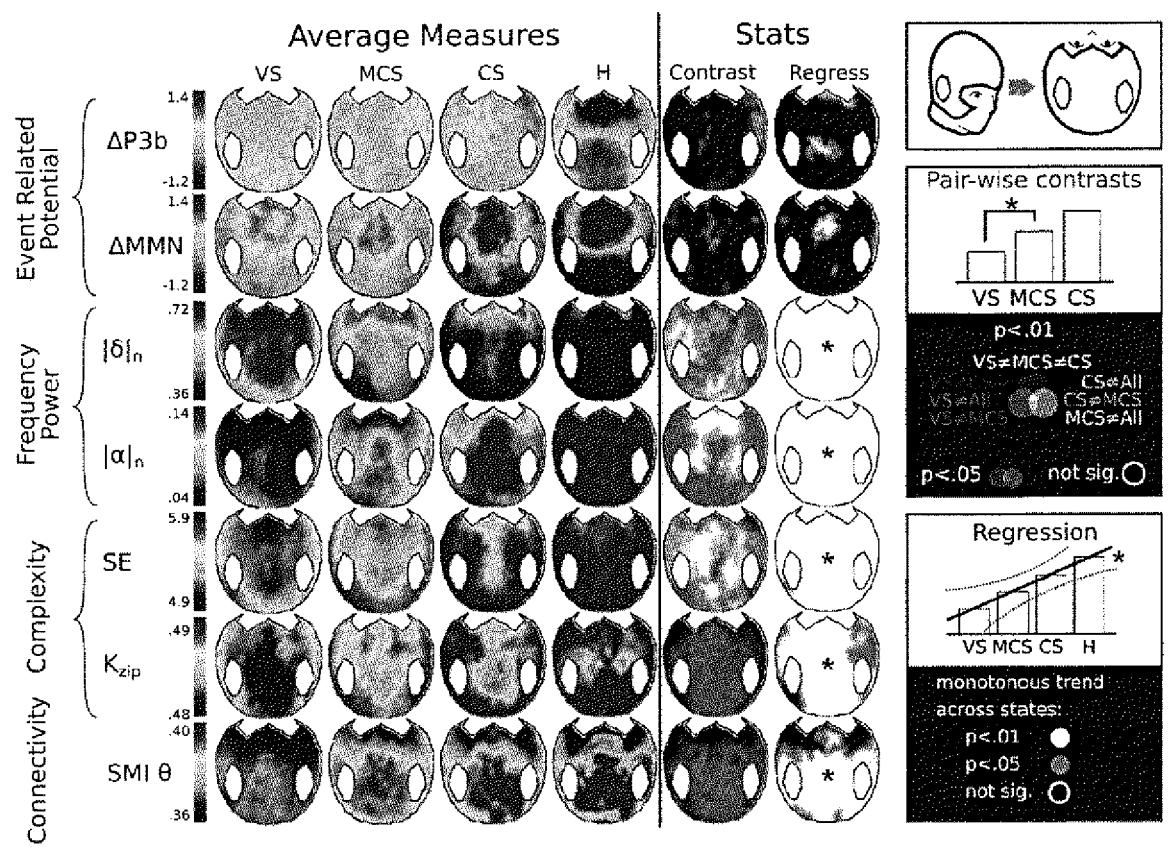

FIG. 9. Scalp topography of the main measures that discriminate between states of consciousness. The first four columns show interpolated views of the corresponding measure on the scalp surface, in polar coordinates (top=front, bottom=back), for each group (VS, MCS, CS and Healthy controls). The fifth column shows the statistics (p<0.01 uncorrected) of the comparisons between the three patient groups. The code for the comparisons is indicated in the lower right corner of the figure (grey and white colors are most relevant since they indicate a significant difference between the VS state and all other states of consciousness). The sixth column shows the statistics of a regression analysis of the measure across the four groups (light gray indicates p<0.05, white p<0.01).

Figure 10:
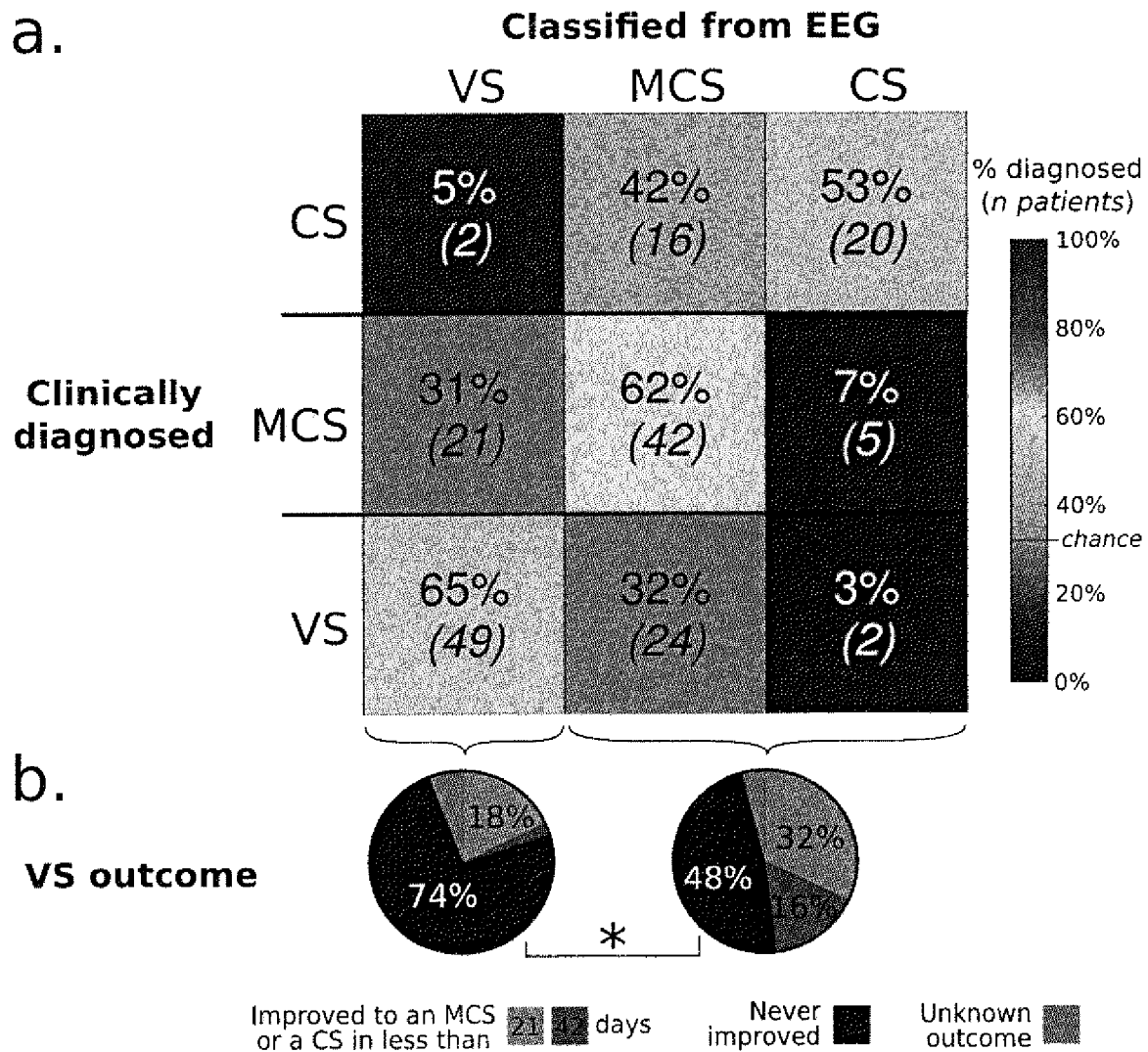

FIG. 10. Comparison of EEG-based classification with clinical diagnosis and patient outcome. Top, confusion matrix showing, on the y axis, the clinical diagnosis, and on the x axis, the prediction using the automatic classifier based on EEG measures. In each cell, the inventors indicate the number of recordings and, in parentheses, the corresponding percentage (out of the total number of recordings with this clinical diagnosis). The diagonal indicates that the EEG-based classification matches the clinical diagnosis in a majority of cases. Off-diagonal terms suggest an inappropriate classification, but may also indicate that EEG measures are detecting information unseen by clinicians. Indeed, the bottom pie charts show the clinical outcome of the VS patients, as a function of whether EEG measures classified them as VS or in a higher state of consciousness (MCS or CS). The probability of recovery was significantly higher ($p_{FDR}<0.05$) for patients classified into a higher state of consciousness than for patients predicted to be truly VS.

Figure 11:
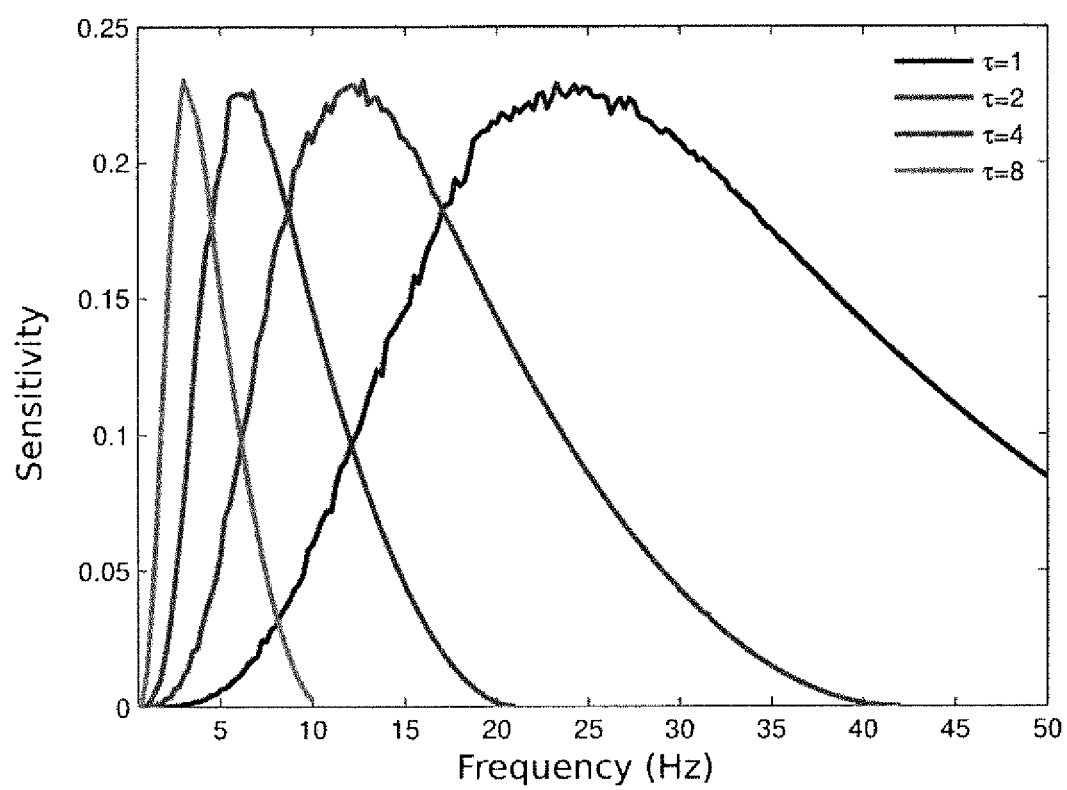

FIG. 11. Sensitivity of the permutation entropy measure to frequencies in the EEG, given different tau parameter values. Sensitivity was measured as one minus the permutation entropy (1−PE). The inventors evaluated how sensitivity varied when the frequency spectrum was scanned using a sinusoidal oscillation embedded in white noise. The graph shows that, when the parameter $\tau$ increases, PE becomes increasingly sensitive to lower frequencies.

Figure 12:
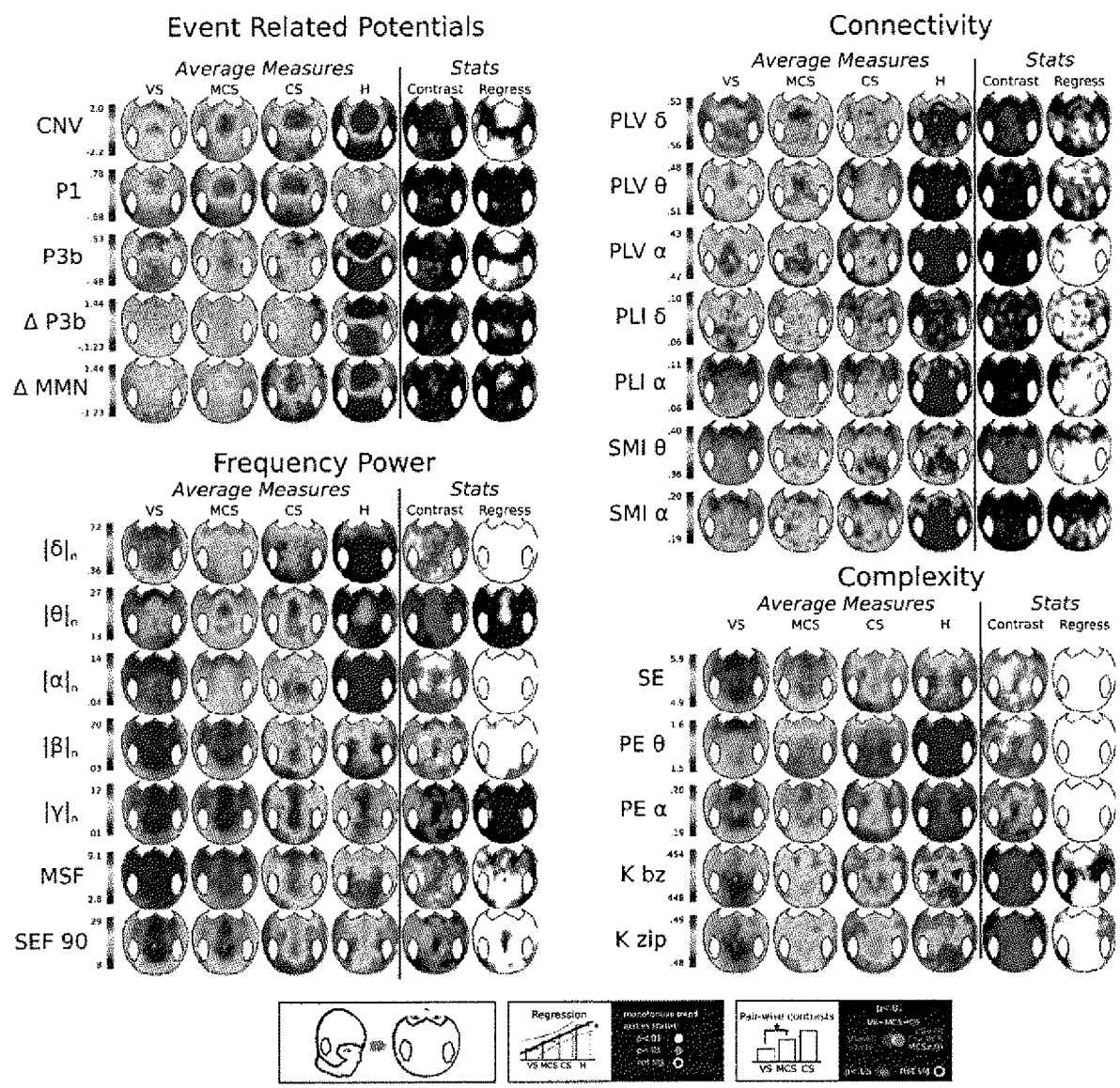

FIG. 12. Scalp topography of all the measures that discriminated between states of consciousness. Same format as FIG. 9.

Figure 13:
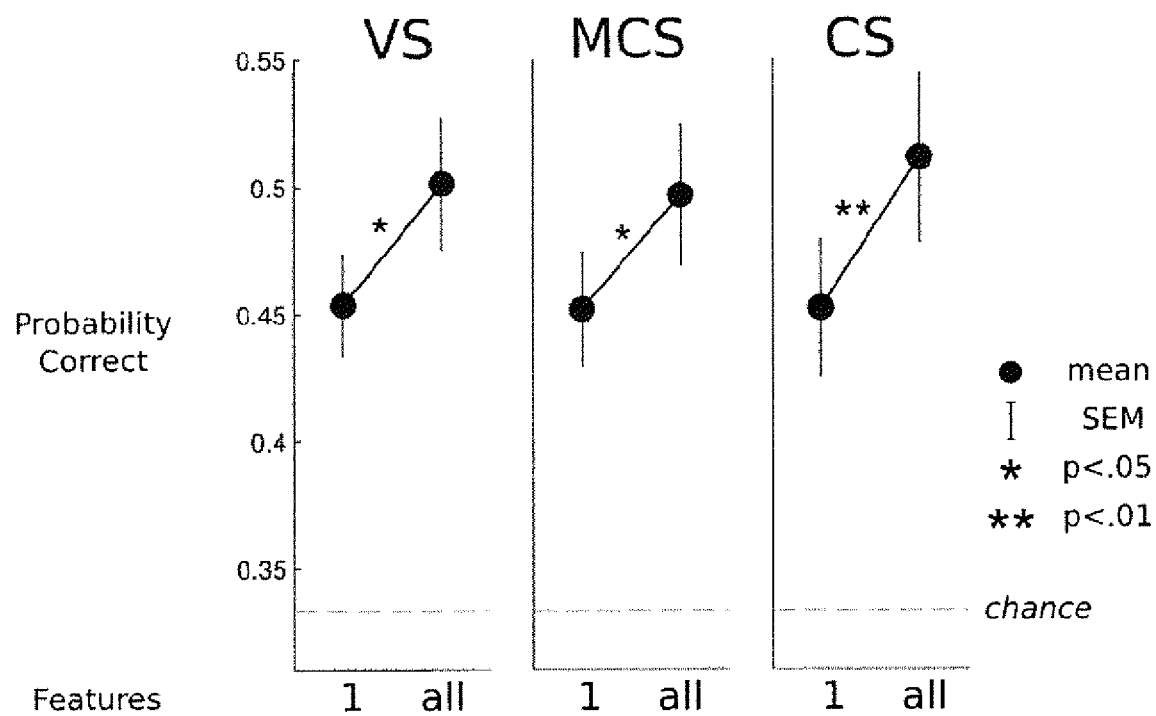

FIG. 13. Discrimination power of the single best measure vs. the combination of all measures. For each conscious state group (VS, left, MCS, middle and CS, right). The inventors compared the probability of being correctly classified based a single measure or on multiple measures combined. In both cases, a k-fold cross-validation procedure was used to obtain an unbiased quantitative estimate of discrimination power (chance 33%). Note that the combination of measures is more efficient than any single measure, suggesting a synergistic interaction: different measures convey partially independent information about states of consciousness.

Figure 14:
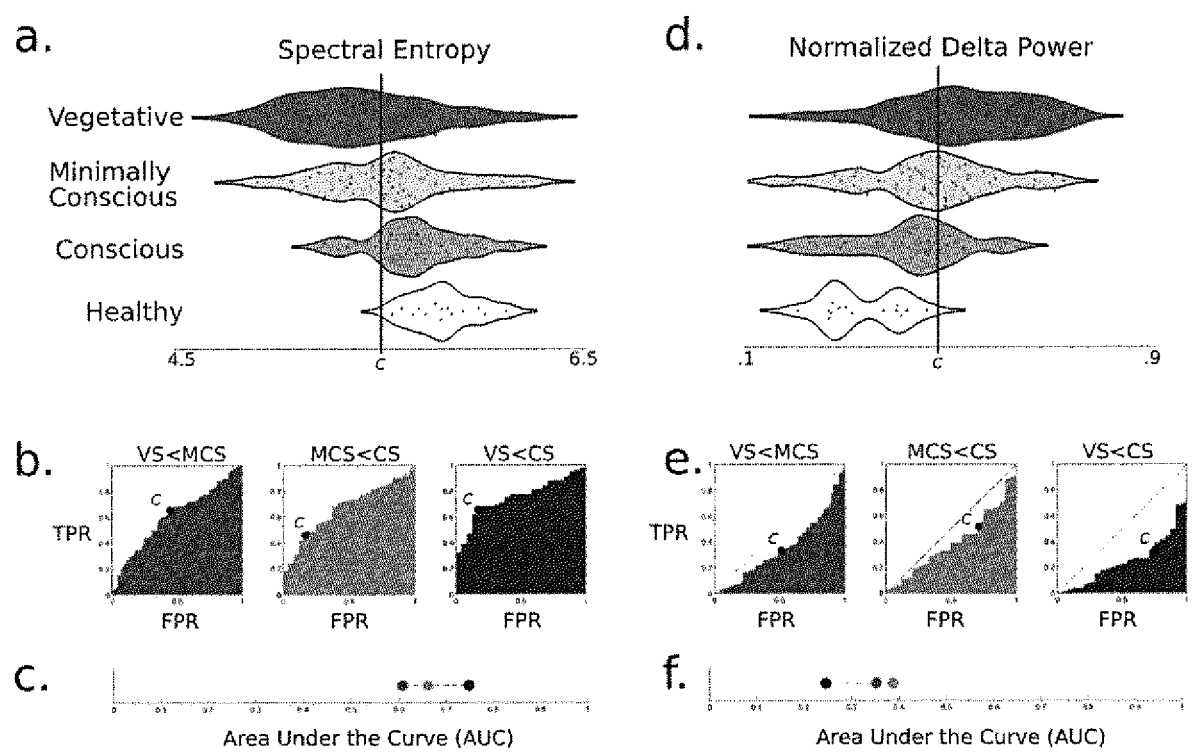

FIG. 14. Receiver operating characteristic (ROC) calculation. ROC curves are calculated from the comparisons between the distributions (i.e. panel A for spectral entropy (SE)) of a given measure for all clinical groups. The curve displays the false positive rates (FPR) versus the true positive rates (TPR) as a discrimination criterion C is varied. In panel B the inventors show the ROC curves corresponding to the MCS>VS, CS>VS and CS>MCS comparisons. The discrimination power of the comparison is quantified from the Area under the curve (AUC) which is equal to the probability of a random element of class A to have a higher value than a random element of class B. For the SE measure the AUC is always >50% for all comparisons, meaning that higher values of this measure index higher clinical states. Panel C displays the AUCs corresponding to the comparisons in same ways as in FIG. 7. In panels D, E and F the inventors repeat the analysis for normalized delta power. This measure has the opposite trend to SE, decreasing with conscious state. In this case, this is capture by AUCs<50%.

Figure 15:
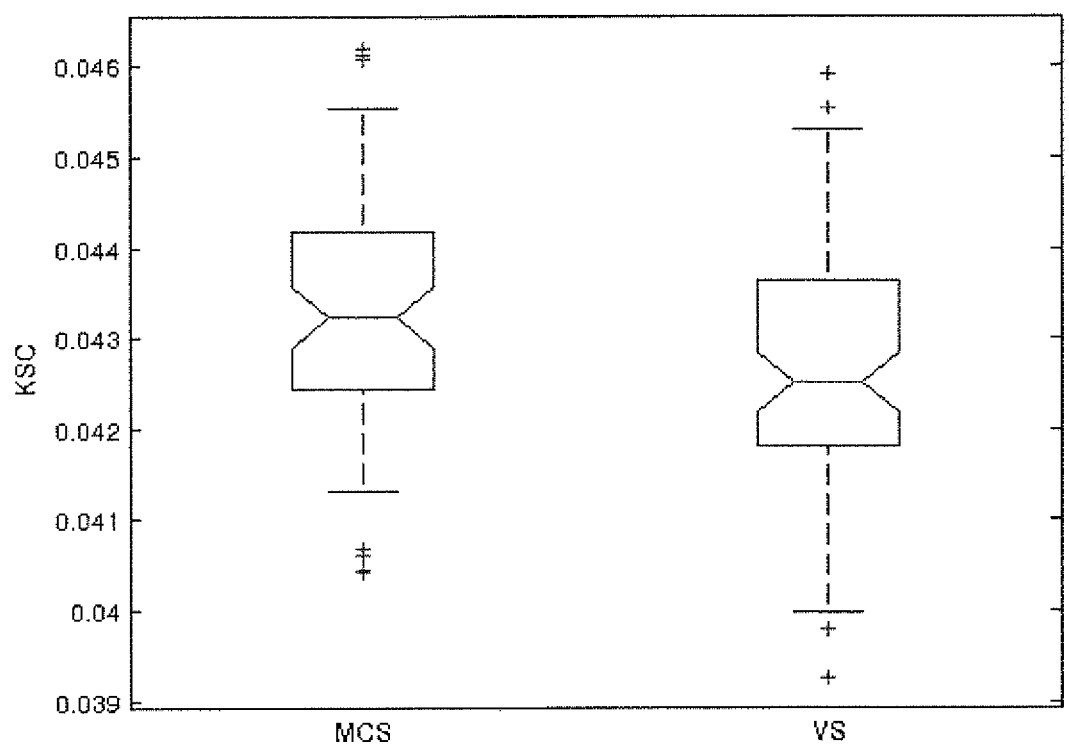

FIG. 15. KSC connectivity summary for VS and MCS patients

Figure 16:
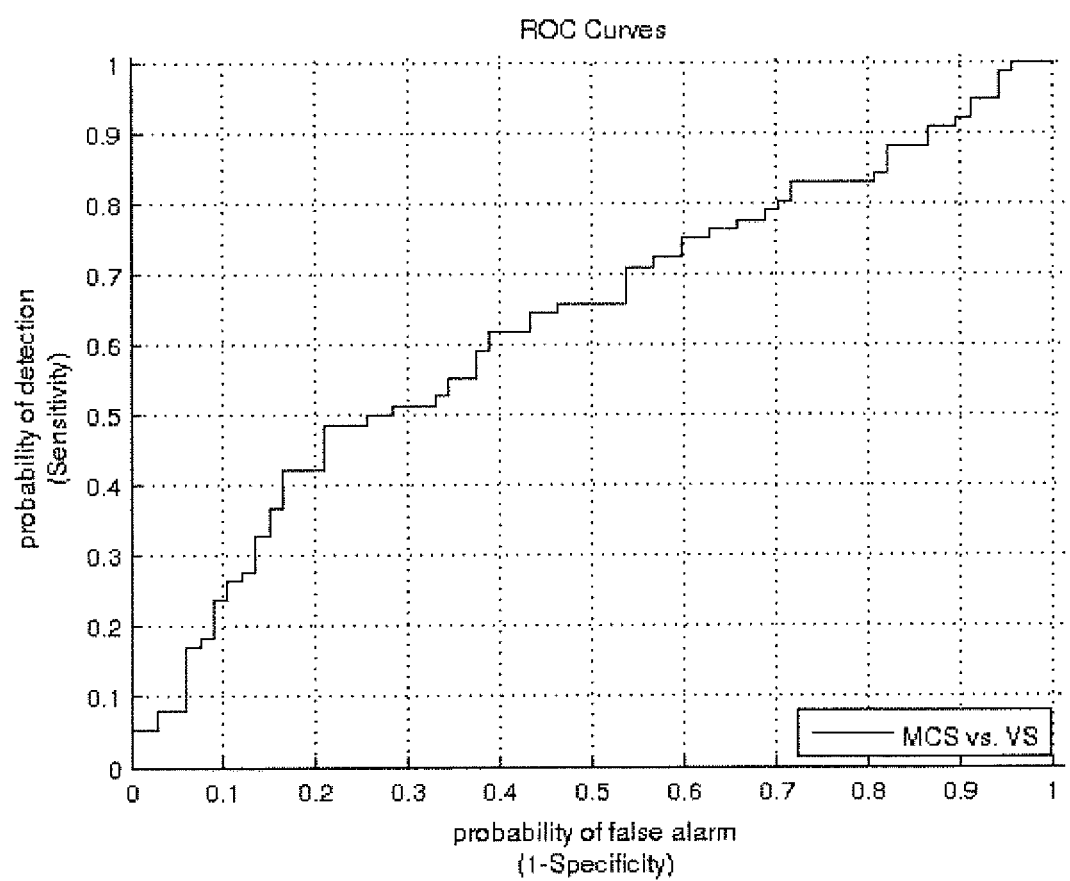

FIG. 16. ROC analysis for the KSC measure

FIG. 17. Symbolic transformation of the EEG signal and wSMI computation (a) The transformation of continuous signals (X) into sequences ($\hat{X}$) of discrete symbols (A, B . . . F) enables an easy and robust estimation of the mutual information shared between two signals. $\tau$ refers to the temporal separation of the elements that constitute the symbol. (b) By computing the joint probability of each pair of symbols the inventors can estimate the Symbolic Mutual Information (SMI) shared across two signals. (c) SMI is weighted to disregard conjunction of symbols confounded with common sources.

Figure 18:
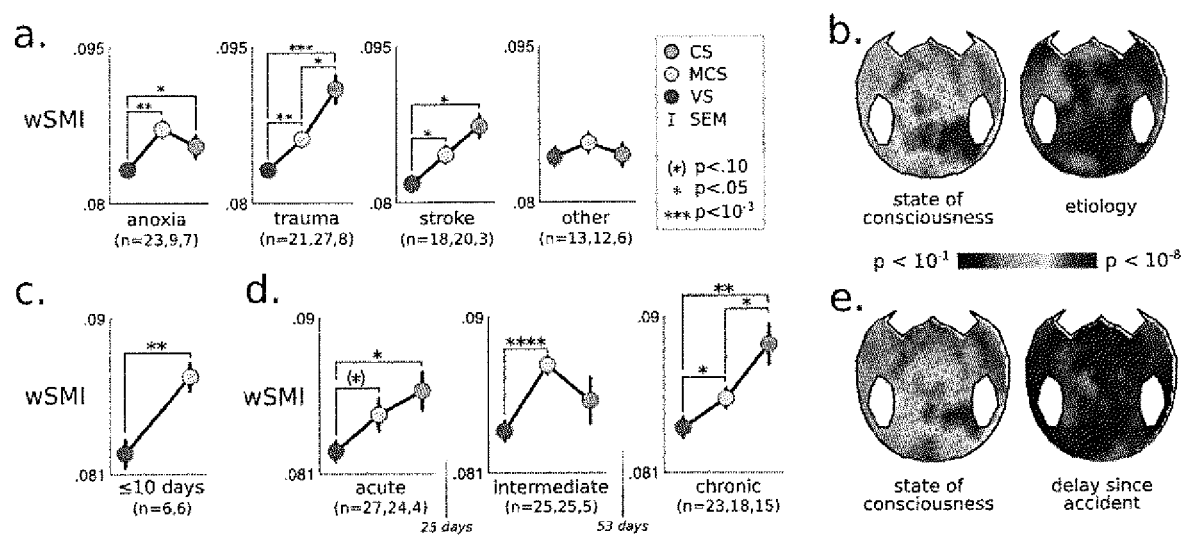

FIG. 18. Etiology and acuteness factors on wSMI (a) The median wSMI across current sources is depicted for each state of consciousness. Error bar represent standard error of the mean (SEM). Significant pair-wise comparisons are denoted with stars. Analyses were reproduced for each (b) etiology and (c-d) degree of acuteness. Results show that median wSMI is mainly affected by consciousness states.

Figure 19:
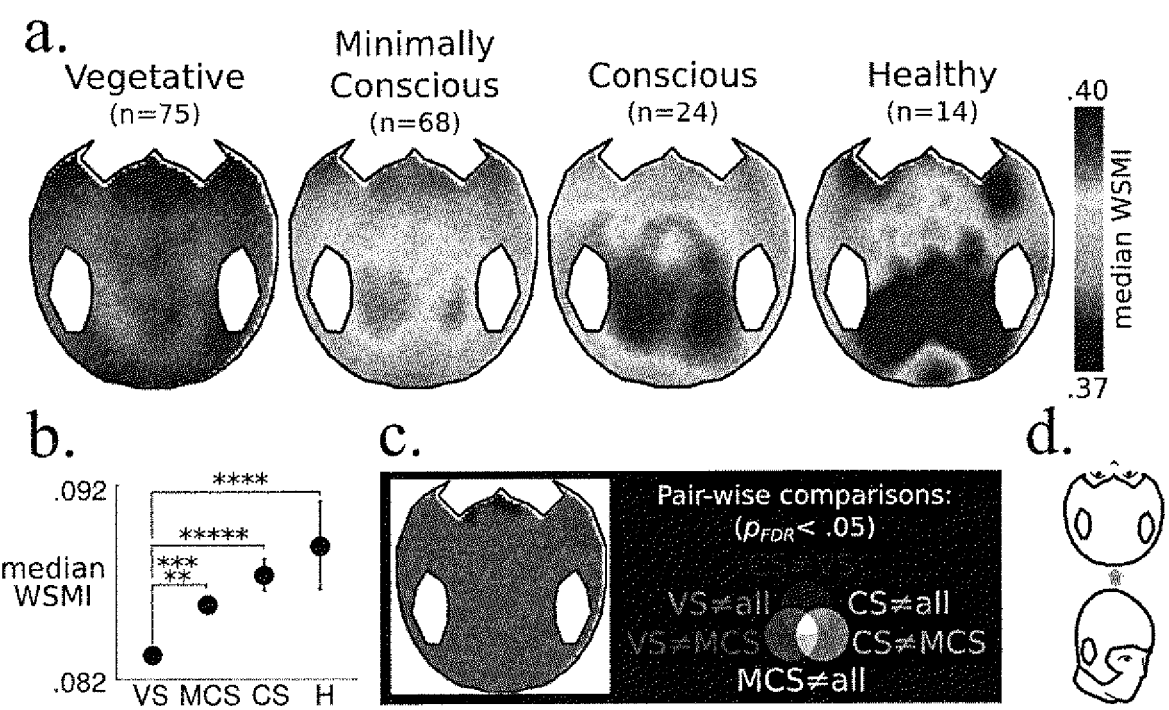

FIG. 19. wSMI increases with consciousness state (a) The median wSMI that a given EEG channel shares with all other channels is depicted for each state of consciousness. (b) Significant pair-wise comparisons are color coded for each EEG channel. (c) Topographies are constructed from the two-dimension transform of the 256 EEG net.

Figure 20:
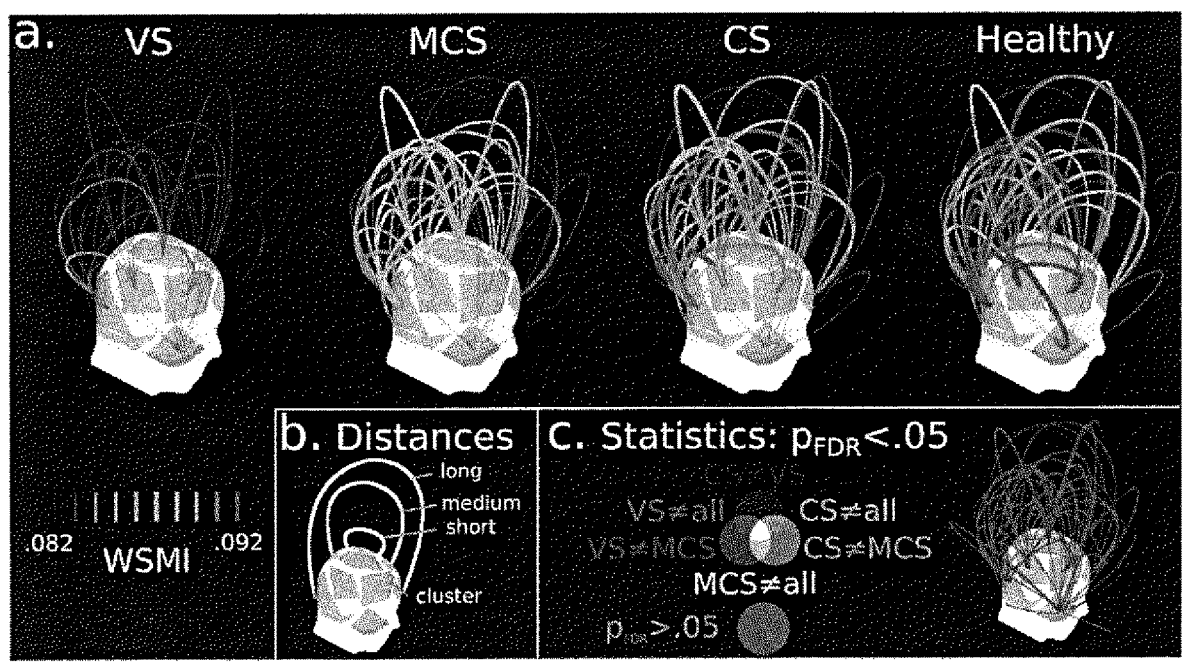

FIG. 20. 3D display of wSMI between major scalp regions.

(a) All 120 pairs formed by 16 clusters of EEG channels are depicted as 3D arcs.

(b) The radius of each arc is proportional to the Euclidian distance separating the two clusters. Color and thickness are proportional to the mean wSMI shared across pairs of clusters.

(c) Statistical comparisons show that VS patients' wSMI is impaired across most clusters.

Figure 21:
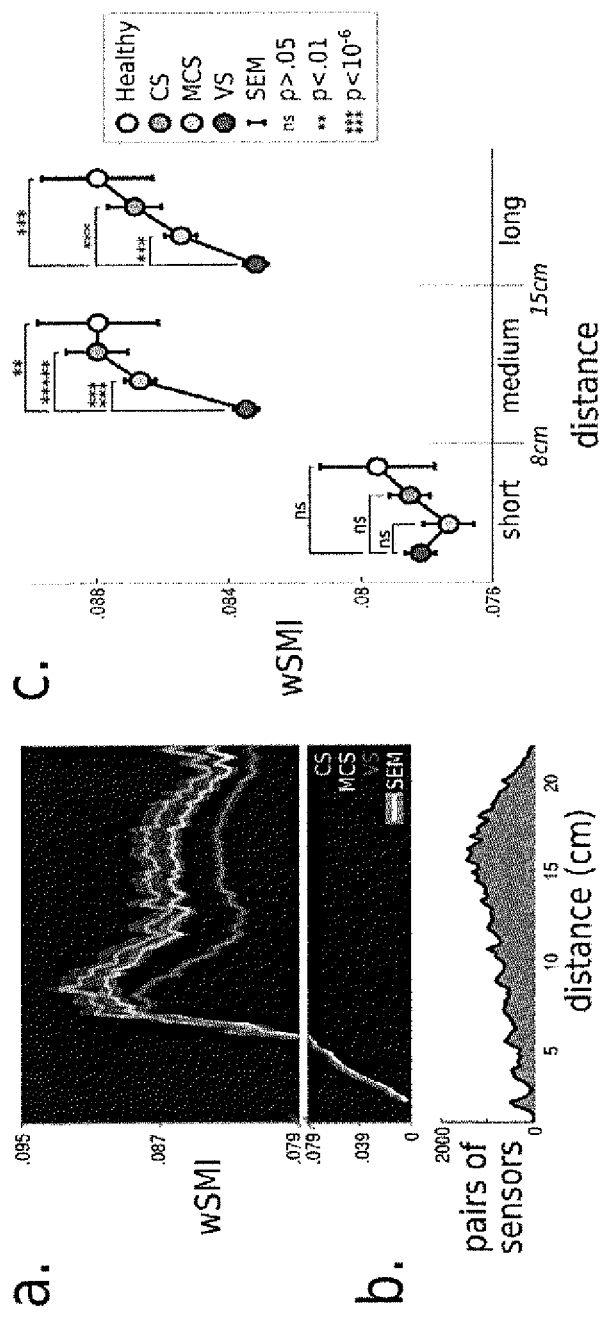

FIG. 21. wSMI as a function of Euclidian distances between EEG channels.

(a) wSMI is plotted as a function of the Euclidian distance separating each pair of EEG channels. wSMI drops towards zero as distances diminish, but are relatively stable from 8 onwards. (b) Histogram plotting the density of channels pairs as a function of distance. (c) Whereas wSMI does not differentiate consciousness states at short distances, VS patients' wSMI is strongly—and is more—impaired at medium and long distances.

Figure 22:
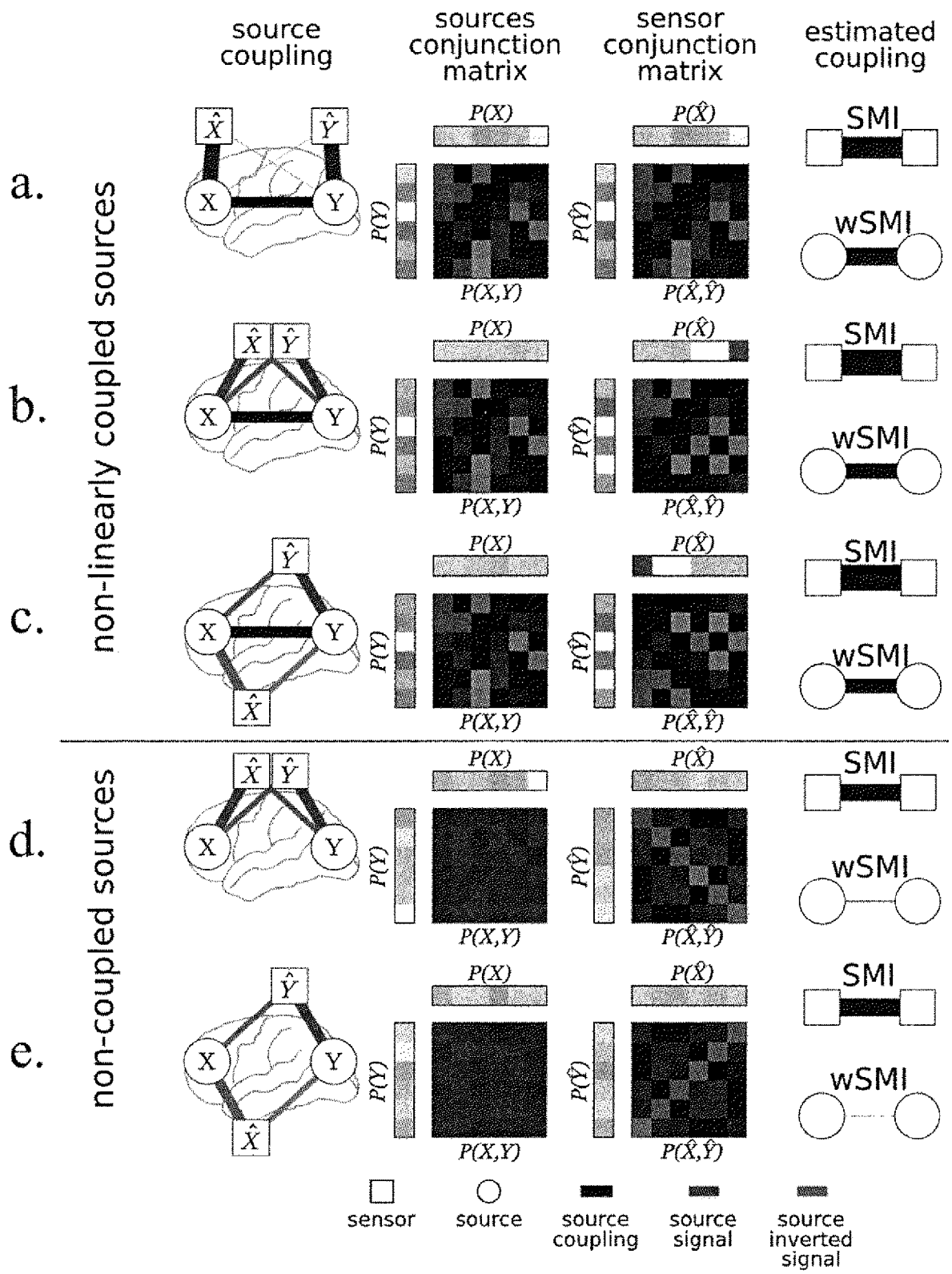

FIG. 22. Qualitative simulations.

The figure depicts, for each simulation (lines) the diagram of the simulation (i), the prior and joint probabilities matrices at the source (ii) and at sensor level (iii) as well as the SMI and wSMI estimated at the sensor level (iv). (i), Circles represent simulated sources (X, Y) and their coupling strength (i.e. the amount of information sharing measured with SMI at the source level) is indicated by the width of the horizontal bar joining X and Y. Squares represent sensors (X hat Y hat), which can both capture a heterogeneous mixture of signals from source X and Y. The amount of signal they received from X and Y is represented by the width of the lines. Blue lines indicate a signal recorded on the positive side of the simulated "electric field" whereas red lines indicate recorded signals with the opposite sign. Line width is proportional to the respective values in the simulations. Red lines indicate a signal recorded at the opposite site of the electric dipole.

(ii) Prior probability of each symbol to belong to each source (P(S|X), P(S|Y)) as well as the joint probability matrix depicting the probability of each symbol SY to occur in Y if X is in SX. (iii) Similar prior probabilities and joint probabilities are estimated at the sensor level.

(iv) Qualitative SMI and wSMI results as estimated from sensor signals (X hat Y hat).

(a-c). Set of scenarios in which there is a strong XY coupling.

(d-e) Set of scenarios in which there is an very small coupling.

(a) Sensors capture quasi pure signals (95%) from their respective source and only a small proportion of the other source (5%). In this trivial case, SMI and wSMI applied at the sensor level are both good estimates of the XY coupling.

(b) Sensors capture heterogeneous signals (65%) from their respective source but are largely contaminated by the other source (35%). In this difficult case, wSMI indicate a real XY coupling.

(c) A similar case to (b), except that one of the sensors is located at the opposite side of X and Y—mimicking the bipolar characteristics of electric fields.

(d) Sensors capture a 65% mixture of X and Y, although XY coupling is close to zero. SMI thus overestimates the amount of XY coupling because it captures mutual information observed at the sensor level. This overestimation is in due to the projection of common source's signals on sensors. Note that the sensor joint probability matrix overestimates the downward diagonal. In contrast to SMI, wSMI remains robust to common source artifacts.

(e) A similar case to (d), except that one of the sensor is located in the opposite side of the sources. Note that the joint probability matrix now overestimates the opposite diagonal. In contrast to SMI, wSMI remains robust to common source artifacts.

Figure 23:
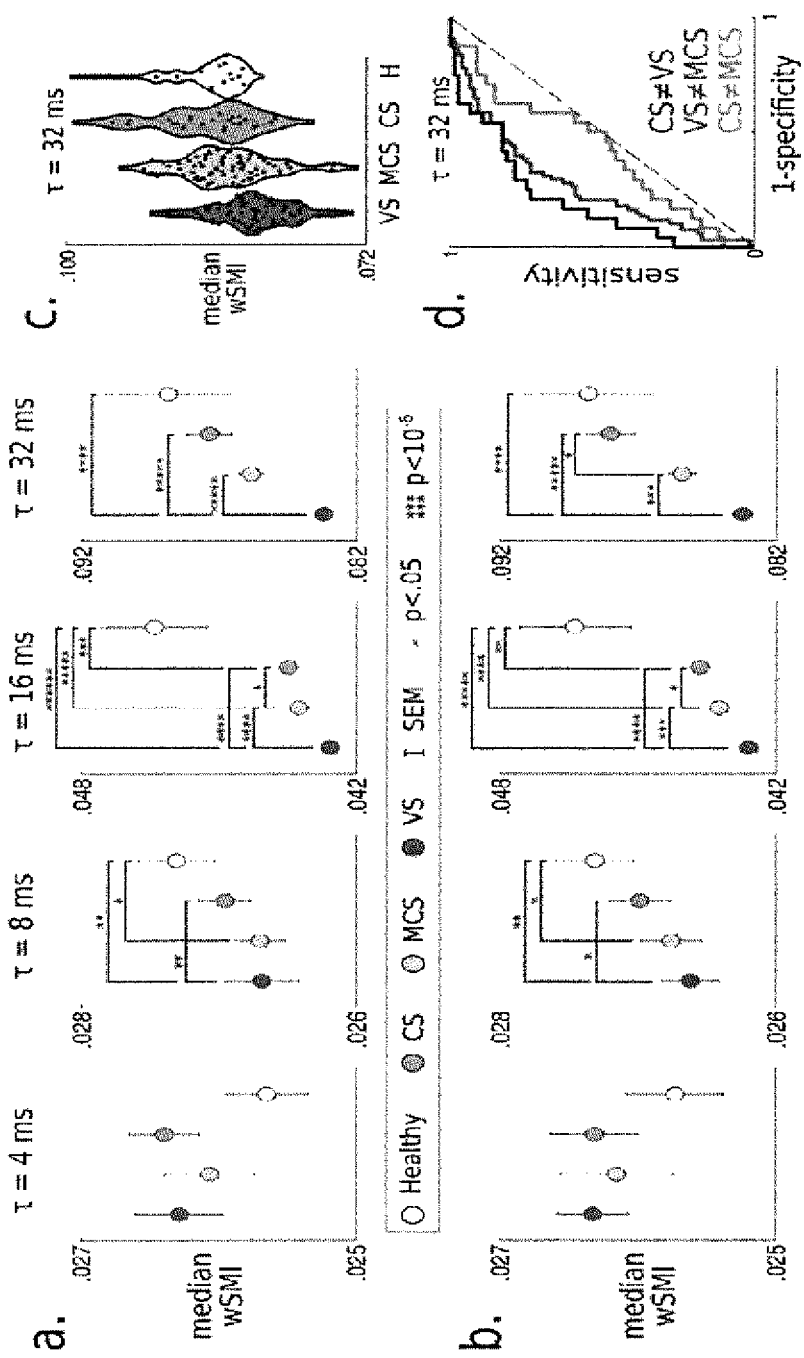

FIG. 23. wSMI is robust to the chosen parameters.

a. Median wSMI obainted all tested parameters ($\tau$=[4, 8, 16, 32] ms).

b. A few DOC patients were evaluated and recorded several times to identify consciousness improvements (see example 1 Methods). This analyses replicates (a) using only EEG recordings obtained from unique subjects.

c. Median wSMI obtained in each individual EEG recording (black dot) as a function of state.

d. Sensitivity—specificity analyses estimated with an empirical Receiver-Operating Curve.

Figure 24:
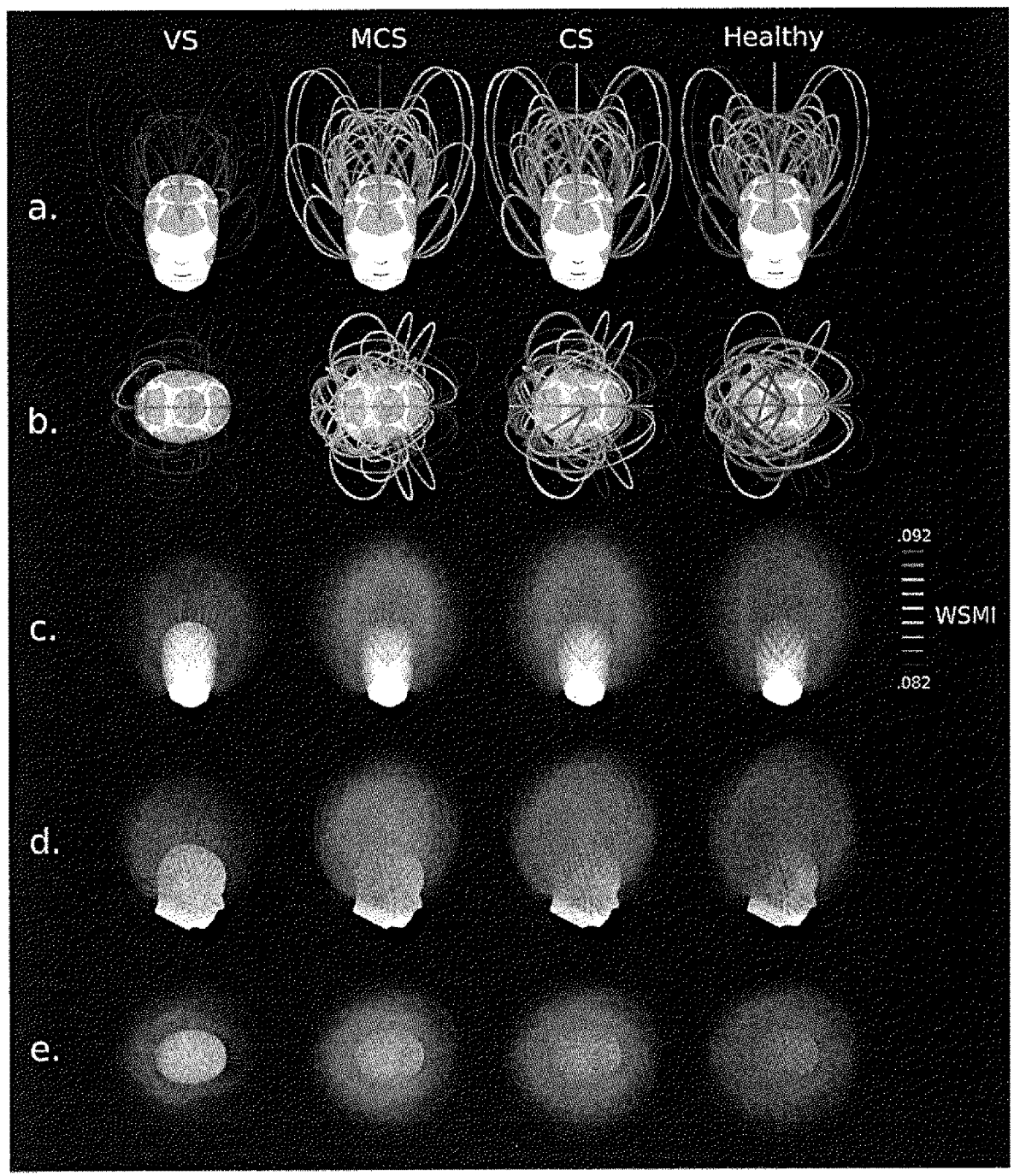

FIG. 24. Non-clusterized wSMI across states of consciousness. (Supplement of FIG. 26)

For each clinically defined state of consciousness, all of the 32640 pairs of current sources are plotted in 3-dimensions following the principles described in FIG. 3. The color of each arc indicates the symbolic mutual information (SMI) for the corresponding channel pair. As in the cluster analysis (FIG. 26), results show that the mutual information between a priori distinct cortical sources increases with states of consciousness.

Figure 25:
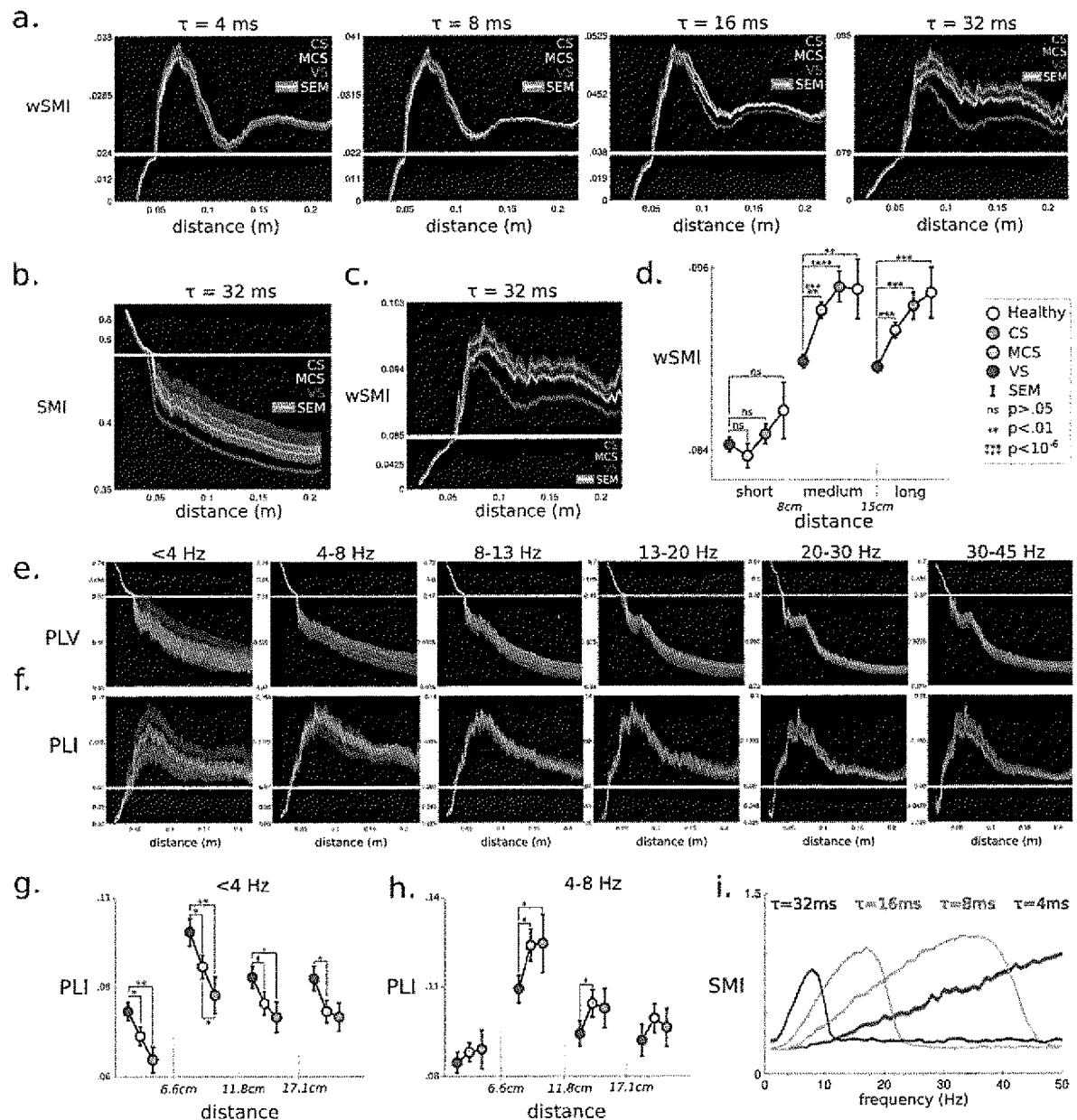

FIG. 25. Complementary analyses.

a. wSMI is presented for all tested ($\tau$=[4, 8, 16, 32] ms). FIG. 28 corresponds to $\tau$=32 ms.

b. SMI at $\tau$=32 ms is displayed. Results show that in contrast to wSMI, SMI exponentially increases as the distance separating two EEG sensors tends towards zero.

c. Replication of the wSMI ($\tau$=32 ms) distance analyses using different time periods of the EEG (post auditory stimulation).

d. Replication of the wSMI ($\tau$=32 ms) statistical analyses using different time periods of the EEG (post auditory stimulation). Results show very similar effects than the one reported in the manuscript.

e. Phase Locking Value (PLV) across distances for each consciousness state and frequency of interest.

f. Phase Lag Index (PLI) across distances for each consciousness state and frequency of interest.

g. PLI statistical analyses across consciousness states at the $\delta$ frequency range. Results suggest a small but significant increase of delta synchrony among VS patients. However this results doesn't interact with distance.

h. PLI statistical analyses across consciousness states at the $\alpha$ frequency range. Results suggest a small but significant impairment of alpha synchrony among VS patients.

DETAILED DESCRIPTION

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Example 1

1.1 Materials and Methods for Example 2, 4 and 5
Participants 181 high-density EEG recordings (75 VS, 68 MCS, 24 Conscious patients (CS), and 14 Healthy controls) were obtained from 126 subjects (Age: M=47 years old, SD=18 years, males: 72%). CS patients refer to patients with severe brain damage but who were still capable of functional communication and therefore did not belong to the MCS category. Note that 60% of CS patients had actually recovered from a VS or an MCS state. 16 DOC patients were recorded twice during their stay at the hospital, and 13 other were recorded between 4 and 6 times. Each of these subsequent recordings were performed between 1 and 673 days (mean=74 days, STD=157 days) following the initial EEG recording, and were aimed at tracking improvements in the patients' clinical state. The inventors categorized each patient in one of three types of delay (acute, intermediate and chronic) separating their accident from the time of EEG recording. Acuteness thresholds were determined from percentile analyses: the acute state refers to the third of patients with the shortest delays between their accident and the EEG recording (<25 days) whereas the chronic state refers to the third of patients with the longest delays (>50 days).

Etiologies were typical of DOC patients: 23% had gone through an anoxia or a hypoxia, 34% had had an intracranial hemorrhage (either ischemic infarcts or intracerebral hemorrhages), and 25% suffered from a traumatic brain injury (TBI). The rest of the patients had suffered from other miscellaneous or mixed etiologies. A chi-square testing the interaction between etiology (hypoxia, intracranial hemorrhage, TBI or other) and conscious state (VS, MCS or CS patients) revealed no significant result: $\chi(6,N=172)=7.13$, $p>0.308$, which suggests that analyses looking at the correlations between EEG measures and patients' states of consciousness will not be confounded by etiology. The delay separating DOC onset and the EEG study was variable (mean=187 days, STD=533 days)), and mainly depended on the necessity for the patients to get an EEG to facilitate clinical diagnosis.

All patients had been without sedation for at least 24 hours prior to the recording session. Trained neurologists (FF, BR, LN) performed a careful clinical evaluation of patients' conscious state based on the French version of the Coma Recovery Scale Revised (CRS-R) (40) before each EEG recording.

Note that EEG recordings of healthy subjects differed from the patients' in many respects that are irrelevant to conscious states: EEG recordings were performed in a quiet EEG room rather than at bedside, without any surrounding clinical equipment, subjects were fully attentive to instructions, clearly understood the task, etc. Thus, the inventors focus primarily on statistical comparisons between the clinical groups of VS, MCS and CS patients. Results from healthy subjects are nevertheless useful in the sense that they inform on the monotony of a given measure of consciousness.

Experimental Design

The EEG recordings were obtained during auditory stimulation following Bekinschtein et al's paradigm (18) for clinical purposes. Except if stated otherwise, analyses focus on time periods during which subjects were presented to undifferentiated series of tones. Thus, and unlike previous studies (10, 18, 20), all trials were pooled independently of the condition of auditory stimulation.

Patients undertook this paradigm for clinical purposes. The auditory stimuli were 50 ms-duration sounds composed of 3 sinusoidal tones (350, 700, and 1400 Hz, hereafter sound A; or 500 Hz, 1000 Hz, and 2000 Hz, hereafter sound B), with 7-ms rise and 7-ms fall times. Sequences were composed of five stimuli presented at a Stimulus Onset Asynchrony (SOA) of 150 ms, and were separated by a variable silent interval of 1350 to 1650 ms (50 ms steps). The sequences could comprise five identical tones (XXXXX, where X can be sound A or sound B) or four identical tones followed by a distinct one (XXXXY). In a given block, 80% of trials consisted in one type of sequence (frequent) and 20% of trials were of the other type (rare sequence), pseudo randomly distributed at least one and at most six frequent trials apart. Each block started with a 30 s habituation phase during which the frequent sound sequences were repeatedly presented to establish the global regularity, before the first rare sequence was heard. Sounds were presented via sterilized headphones with an intensity of 70 dB, using E-prime v1.2 (Psychology Software Tools Inc.). At the beginning of each block, the experimenter gave a spoken instruction to count the rare sequences. The instructions attempted to motivate the patient to pay attention to sound, and patients were systematically called by their first names. All subjects heard at least 8 blocks in a pseudo-random sound fixed-rule order (two runs of AAAAA, BBBBB, AAAAB, BBBBA global standards). Up to four additional blocks could be performed in case of highly noisy recordings.

Since the goal was to probe information exchanges in ongoing brain activity, unlike previous studies (21-23), all trials were pooled independently of the condition of auditory stimulation. Analyses were performed over 800 ms epochs, first during the initial period of auditory stimulation (−200 ms before 1st sound until the beginning of last sound which could differ across conditions), and were then subsequently replicated on the time period following the beginning of the last sound (+600 ms to +1336 ms) for control analyses.

EEG Recording and Preprocessing

EEG recordings were sampled at 250 Hz with a 256-electrode geodesic sensor net (EGI, Oregon, USA), band-pass filtered (0.2-45 Hz) and segmented from −200 ms to +1336 ms relative to the onset of the first sound and baseline corrected over the first 200 ms. Trials in which voltages exceeded ±150 V, eye-movements activity exceeded ±80 mV or eye-blinks exceeded ±150 mV were rejected. All these processing stages were performed in the EGI Waveform Tools Package. Channels with a rejection rate superior to 20% across trials were rejected. Bad channels were interpolated with non-artifacted neighboring channels. Trials with more than 20 bad channels were rejected. Four recordings with fewer than 200 remaining non-artifacted trials were excluded from the present study.

Current Source Density (CSD) estimates—also known as Laplacian transforms—were implemented using Kayser & Tenke (24) script on each subject separately. CSD is close to subtracting, from each channel, the activity of neighboring sensors; this technique thus diminishes volume conduction and increases the spatial focalization of EEG information.

Analyses specifically referring to Fz, Cz and Pz EEG channels were based on an average of 6 EEG channels surrounding each of these channels.

Indices of Information Sharing

In order to quantify the coupling between sensors the inventors introduce a novel index: symbolic mutual information (SMI). EEG signals were transfolined in a series of discrete symbols using the same principles as in (25). The main advantages of this method are (1) the possible identification of nonlinear patterns in the signal (2) the reduction of the problem space to a limited set of discrete symbols and (3) its robustness to noise. The details of this computational step are provided in the supplementary method. The inventors calculated the symbolic transformation for every channel/trial with the following parameters: n=3 time samples (sampled at 250 Hz) and τ=4, 8, 16 or 32 ms (i.e. 1, 2, 4 or 8 time samples).

A non-directional estimate of the coupling between two EEG recordings can be obtained by computing the mutual information between two time series. In this case, the inventors computed the mutual information between each pair of electrodes after doing the previously described symbolic transformation. The inventors refer to this measure as Symbolic Mutual Information (SMI) whose computation is described in the supplementary method.

Phase-lag index (PLI) (26) which measures the asymmetry of the distribution of phase differences between two signals was also estimated on various frequency bands (0-4 Hz, 4-8 Hz, 8-13 Hz, 13-20 Hz, 20-30 Hz, 30-45 Hz).

Directional connectivity measures based on the symbolic transform mentioned above were finally implemented. Symbolic Transfer Entropy (STE) (17) accounts for the divergence of transitional probabilities in a given signal when the infolination from a second signal is available and can thus be used to estimate the information flow from between two signals.

Statistics

Except if stated otherwise, statistical analyses were performed with R and Matlab (2009b), with non-parametric methods and two-tail tests (based on Wilcoxon, Mann-Whitney U tests and robust regression methods). Significance level was set to p<0.05, and false discovery rate (FDR) was used to correct for multiple comparisons (hereafter noted as $p_{FDR}$).

Connectivity analyses were performed on each pair of CSD transform of EEG signals. Except if stated otherwise, topographies represent the median connectivity each CSD estimate share with all other non-facial channels. Cluster analyses were performed by averaging the measures obtained from the 256 CSD within 13 (SMI) or 16 regions (STE).

Distance analyses were performed to estimate how functional connectivity varies with the spatial distance separating two EEG channels. Distance between channels was calculated along a straight line in a 3-dimensional Euclidian space using the EGI default electrode coordinates.

Indices of Information Sharing

In order to quantify the coupling between sensors the inventors introduce a novel marker: symbolic mutual information (SMI). SMI is an extension of the permutation entropy analysis (27) and is calculated between each pair of channels, and for each trial, after the transformation of the EEG time series into a string of discrete symbols. As explained below, the advantage of this measure is its ability to detect non-linear coupling, its computation time and its robustness to noisy EEG.

Symbolic Transform

Permutation entropy (PE), introduced by (27), is an effective method to compare time series and distinguish different types of behavior (i.e. periodic, chaotic or random) in the signal. The main advantages of this method are (1) the possible identification of non-linear patterns in the signal (2) the reduction of the problem space to a limited set of discrete symbols (3) its robustness to noise. The basic principle of this method consists in transforming a signal into a sequence of discrete symbols and to quantify the entropy of the signal from the probability densities of those symbols. The transformation is performed by first extracting sub-vectors of the signal, each comprising n measures separated by a fixed time delay (τ). The parameter τ thus determines the broad frequency range to which the symbolic transform is sensitive.

Because using τ values larger than 1 can induce aliasing, the inventors applied a low pass filter to the continuous signal in order to maintain the frequency-band specificity of each measure. Cutoff frequencies were set according to the following empirical formula: $f_{LP}$=(80 Hz)/τ. Each sub-vector is then assigned a unique symbol, depending only on the order of its amplitudes. For a given symbol size (n) there are n! possible orderings and thus n! symbols. The inventors calculated the symbolic transformation for every channel/trial with the following parameters: n=3 time samples (sampled at 250 Hz) and τ=4, 8, 16 or 32 ms (i.e. 1, 2, 4 or 8 time samples). The parameter n determines the number of symbols in the transformation (n!). In this case, to robustly estimate the symbols probability densities, the inventors choose n=3. This value has been shown to be sufficient to detect dynamical changes in EEG during anesthesia (28). Symbolic transform of a signal X will be hereafter referred to as $\hat{X}$. After the symbolic transformation of the signal, the probability of each symbol to appear in a specific CSD estimate is calculated.

Symbolic Mutual Information (SMI)

A non-directional estimate of the coupling between two EEG recordings can be obtained by computing the mutual information between two time series. In this case, the inventors computed the mutual information between each pair of electrodes after doing the previously described symbolic transformation. The inventors refer to this measure as Symbolic Mutual Information (SMI) estimated as follow:

$$SMI(\hat{X}, \hat{Y}) = \sum_{\hat{x} \in \hat{X}} \sum_{\hat{y} \in \hat{Y}} p(\hat{x}, \hat{y}) \log \frac{p(\hat{x}, \hat{y})}{p(\hat{x})p(\hat{y})}$$

where $\hat{x}$ and $\hat{y}$ are all symbols present in signals $\hat{X}$ and $\hat{Y}$ respectively; $p(\hat{x}, \hat{y})$ is the joint probability of co-occurrence of symbol $\hat{x}$ in signal $\hat{X}$ and symbol $\hat{y}$ in signal Y; and $p(\hat{x})$ and $p(\hat{y})$ are the probabilities of those symbols in each respective signal. The probability rate $P_R(\hat{x}, \hat{y})$ refers to $$P_R = \frac{p(\hat{x}, \hat{y})}{p(\hat{x})p(\hat{y})}$$

Weighted Symbolic Mutual Information (wSMI)

Weighted Symbolic Mutual Information (wSMI) is introduced to disregards trivial conjunction of patterns across two signals. Indeed, EEG is notorious for being subject to a series of artifacts, including muscle contraction, eye blinks and volume conduction, which artificially induces common signal patterns in distinct EEG sensors. In consequence, SMI can be applied to conjunction of symbols which are less likely to be caused by common sources. With a symbol size of 3 (k=3), most trivial patterns corresponds to the conjunction of identical items (SX=SY), as well as the conjunction of opposed items (SX=−SY). Opposed items could indeed be found if two EEG sensors records each electric side of a common dipole. These two set of symbol pairs (identical and opposed) corresponds to the two diagonals of the joint probability matrix. The computation of wSMI follows SMI's with the addition of a weight parameter:

$$wSMI = \sum_{x \in X} \sum_{y \in Y} w(x, y)p(x, y)\log \frac{p(x, y)}{p(x)p(y)}$$

Phase Locking Value and Phase Lag Index

The Phase Locking Value (PLV) measure the phase correlations of two signals. The Phase Lag Index (PLI) method, proposed by (29) measures the asymmetry of the distribution of phase differences between two signals. The advantage of PLI, as compared to traditional functional connectivity analyses such as phase coherence and Phase Locking Value (PLV), as well as to the SMI method introduced above, is that it is avoids the spurious assignment of a high functional connectivity value to two EEG channels that both reflect the same underlying neural source. Indeed, whenever two channels record voltages arising from a shared source, their instantaneous phase difference is essentially 0 modulo $\pi$, leading the sign of the PLI to converge towards 0 (29).

To estimate it, signals are first band-passed filtered at a given frequency range and Hilbert transformed (in the present study: 0-4 Hz, 4-8 Hz, 8-13 Hz, 13-20 Hz, 20-30 Hz, 30-45 Hz). The 14 difference in instantaneous phase is computed for each pair of CSD estimate, at each time point and for each trial.

Both PLV and PLI methods are affected by the number of time samples they consider. Like the traditional Phase Locking Value method, PLI is affected by the number of time samples considered. At the extreme, if only one time-sample is considered, its average value will be equal to 1 or −1, even if the two channels are fully independent. The more time samples are considered, the less PLI overestimates the connectivity between two channels. As there was a variable amount of non-artifacted trials performed by each patient, the inventors first computed a single-trial PLI estimate, for each trial, by averaging the sign of the phase difference across all time samples within this trial. Each trial had the same number of time samples; these values could therefore be compared with one another. For each subject, the absolute value of these single-trial PLIs was then averaged across trials to yield a final PLI estimate. As a consequence, trial number only affected the robustness of the PLI estimate, and did not introduce a systematic bias related to the number of trials. Both measures are computed using the following formulas:

$$PLV = \left| \frac{1}{N} \sum_{\tau} \phi_{\Delta}(\tau) \right|$$

$$PLI = \frac{1}{N} \sum_{n=1}^{N} \left| \frac{1}{S} \sum_{s=1}^{S} \text{sign}[\phi 1(s) - \phi 2(s)] \right|$$

Where N is the total number of trials, S the total number of time sample in a given trial, and $\varphi 1(s)$ and $\varphi 2(s)$ the instantaneous phases of the two channels considered at a given time sample s.

Directional Connectivity: Symbolic Transfer Entropy (STE)

Beyond the mutual information of two signals, which provides only correlational evidence, several methods have been developed in the past decades to estimate the causal interactions between neural signals. Two main approaches have emerged in the neuroimaging field: Dynamical Causal Modeling (DCM) compares full causal models in their ability to fit a signal set, whereas granger causality or transfer entropy measures compare information flow across pairs of signals.

Dynamical Causal Modeling (DCM) provides a way to compare different models of brain activity that may account for a given dataset (30-31). While data cannot directly provide causal information, models fitted to the data make different assumptions about causal flows. These models are then compared with one another in their ability to fit the data with a minimum number of parameters. However, the derivation of DCM models from EEG data requires a series of non-trivial methodological steps. First, in order to create a realistic forward model of the head that may be inverted to yield current source estimates, the subjects' MRI must be correctly segmented and the conductances properly estimated a critical procedure in a clinical situation, as many patients present extensive brain and skull damage and limit the usage of common head models. Second, a very small set of areas contributing to the EEG signal must be decided a priori, as the number of DCM models increases over-exponentially with the number of areas (32). Yet, fMRI and intracranial recordings have shown that numerous cortical sites are recruited by the present auditory task (21), presumably reflecting its perceptual, attentional and working memory demands. Modeling such data with a small number of sources thus becomes difficult and potentially highly inaccurate (33-34).

For these reasons, and to keep the number of preprocessing layers and a priori assumptions to a minimum, the inventors did not perform DCM. Instead, to estimate causal interactions amongst patients' brain areas, the inventors quantified the Transfer Entropy (TE) of all pairs of current-source density estimates. This method has the advantages of not requiring a model of the interaction and to be able to capture nonlinear interactions (20). In this case the inventors calculated TE on the symbolic transformed signals; this method is named Symbolic Transfer Entropy (STE). As in Granger Causality analyses, the essence of STE is to estimate information flow from Y to X., i.e. the extent to which the knowledge of signals X and Y better predicts the future of X, than the knowledge of signal X alone. STE differs from Granger Causality, however, in the way that it actually estimates this added information. Granger relies on a multiple linear regression, whereas STE relies on information theory applied to non-linearly transformed signals.

STE accounts for the divergence of transitional probabilities in a given signal when the information from a second signal is available:

$$STE_{\hat{Y}, \hat{X}} = \sum p(\hat{x}_{i+\delta}, \hat{x}_i, \hat{y}_i) \log \frac{p(\hat{x}_{i+\delta} | \hat{x}_i, \hat{y}_i)}{p(\hat{x}_{i+\delta} | \hat{x}_i)}$$

Where the sum runs on all symbols of the sequences $\hat{X}$ and $\hat{Y}$. The lag separating the two time samples of interest is referred to as $\delta$. corresponds to the joint probability of concurrence of any given symbol in signal $\hat{X}$ at time i, in signal $\hat{Y}$ at time i and in signal at time i+$\delta$. $p(\hat{x}_i + \delta | \hat{x}_i)$ corresponds to the transitional densities in signal. Finally $p(\hat{x}_i + \delta | \hat{x}_i, \hat{y}_i)$ refers to the same transitional densities but conditional to the symbols in signal $\hat{Y}$ at time i.

FIG. 1 provides a schematic representation of the actual meaning of this equation. Symbols' size ($\tau$) was identical to SMI analyses ($\tau$=4, 8, 16 and 32 ms), and STE was tested at different lags ($\delta$=12, 36, 60, 84, 120, 144, 180, 204 and 240 ms) to check for parameters robustness. If not mentioned otherwise, analyses report STE computed with the following parameters: $\tau$=32 ms, $\delta$=36 ms.

To increase the robustness of probability density estimation, and therefore the reliability of the directional connectivity measure, STE was computed from the following procedure: 1) for each trials, EEG channel or CSD estimation were transformed into symbolic sequences. 2) Metatrials were then formed from the concatenation of 10 temporally consecutive trials. 3) Probabilities densities were computed for each meta-trial. 4) Finally, STE was averaged across all meta-trials.

The net information transfer, $\Delta$STE, is computed from the difference between $STE_{X,Y}$ and $STE_{Y,X}$.

Unlike STE, $\Delta$STE can be directly interpretable within a given recording. However, as any directional and non-directional connectivity analyses, the quantitative value of STE can be importantly affected by signal-to-noise-ratio (35); it is thus important to only consider the comparison across groups, rather than taking the STE values as representative of the actual amount of information transferred across brain regions.

Finally, it should be underlined that STE is an information flow measure and does not necessarily imply a direct causal link between the two signals considered (X & Y). For instance, if a third area Z influence both X and Y, it remains possible to find a net information flow from X to Y, even if X is not directly linked to Y. However, the more areas are considered, and the less the inventors can estimate transition probabilities with a given dataset. Following most directional connectivity, or "causality" analyses based on transfer entropy, the inventors therefore restricted the analyses to pairs of signals.

Because of both the difficulty in estimating causality from an EEG signal, directional connectivity analyses should be taken with great caution and should thus remain subject to later investigation using a combination of intracranial recordings and electric or magnetic stimulation of the neural networks involved.

Statistics:

Topographical Summaries

Connectivity analyses were performed on each pair of CSD transform of EEG signals. As a result, for each subject, the inventors obtained 32640 (256×(256−1)/2) values for non-directional analyses, and 65280 values for directional analyses. As this huge dimensionality leads to an important multiple comparison issue, statistics were often performed on reduced measures (e.g. median across all pairs) or in smaller search spaces.

Except if stated otherwise, topographies represent the median connectivity each CSD estimate share with all other non-facial channels. It thus estimates the amount of information shared by a given area with the rest of the brain. Note that the median connectivity is much more influenced by medium and long distance connections than short ones because most channels are distant by more than 10 cm from one another.

Cluster Analyses

Cluster analyses were performed in order to render the interpretation more straightforward and minimize the issues associated with multiple comparisons. Once SMI and STE were estimated for each pair of channels, the 256 channels were summarized into 13 (for STE: excluding facial channels) or 16 (for SMI: including facial channels) regions (symmetric across the antero-posterior axis). The inventors then calculated, within each of the pairs of clusters, a summary measure by averaging the median connectivity that every channel of the first cluster shared with every channel of the second cluster.

Distance Analyses

Distance analyses were performed to estimate how functional connectivity varies with the spatial distance separating two EEG channels. Distance between channels was calculated along a straight line in a 3-dimensional Euclidian space ($d=\sqrt{(x_1-x_2)+(y_1-y_2)+(z_1-z_2)^2}$ using the EGI default electrode coordinates.

1.2 Materials and Methods for Example 3

Patients

Patients undergone EEG recording for clinical purposes. The auditory paradigm they were presented (18) elicits event related potentials (ERPs) that help assessing patients' present and future state of consciousness (10, 20, 26, 37, 38, 39). Patients were recorded without sedation since at least 24 h in order to maximize their arousal and their cognitive abilities during the auditory stimulation. The inventors performed a total of 173 patient recordings. Six recording were discarded because they presented less than 200 non-artifacted trials (see below). The remaining 167 valid recordings were acquired from 112 distinct patients (78 males and 34 females, sex-ratio=2.29), aged from 16 to 83 years (mean=48±17 years). Patients were recorded from one to six times. They were affected by the following usual conditions: anoxia (24%), intracranial hemorrhage (35%), traumatic brain injury (24%), and other etiologies (17%). The cohort had variable delays separating the incident and the acquisition of the EEG (mean=178 days since DOC onset; median=35 days; SD=532 days; earliest=6 days; latest=4383 days).

Healthy Subjects

Experiments were approved by the Ethical Committee of the Salpêtrière hospital. All 14 healthy subjects (mean age=21.3±2.9; sex-ratio (M/F)=2.5) gave written informed consent.

Behavioral Assessment of Consciousness

Clinical evaluation of consciousness was based on the French version of the Coma Recovery Scale Revised (CRS-R) scale, and careful neurological examination by trained neurologists (FF, BR, LN). This scale consists of 23 items forming six subscales addressing auditory, visual, motor, oromotor, communication and arousal functions. CRS-R subscales are comprised of hierarchically arranged items. The scale enables a distinction between conscious (CS), minimally conscious (MCS) and vegetative (VS) states (26). Clinical examination and behavioral assessment were systematically performed right before EEG recording.

Auditory Stimulation

Subjects undergone the "local-global" protocol (18). Each trial was composed of a series of five 50-ms duration sounds presented via headphones with an intensity of 70 dB and a 100 ms interval between each sound (stimulus onset asynchrony [SOA]=150 ms). Each sound was composed (5) of three superimposed sinusoidal tones (either a low-pitched sound composed with a mixture of 350, 700 and 1400 Hz tones, hereafter sound X; or a high pitched sound composed with a mixture of 500, 1000 and 2000 Hz tones, hereafter sound Y). Tones were prepared with 7 ms rise and 7 ms fall times. Four different series of sounds were used, the first two using the same five sounds: XXXXX or YYYYY (hereafter denoted as XX); and the other two with the final sound differing from the four other: XXXXY or YYYYX (hereafter denoted as XY). Trials were separated by a variable interval of 1350-1650 ms (50 ms steps). Blocks were arranged to contain the XY trials, either as a rare (block type 1: 80% XX/20% XY); or as a frequent (block type 2: 80% XY/20% XX) series of sounds. Both blocks presented a local (the fifth sound could be deviant or identical to previous sounds) and a global regularity (one of the series of sounds was rarer than the other). In order to unambiguously establish the global regularity, each block started with ~30-second habituation time period during which only trials with series of sounds of the frequent type were presented. Following the original design (18), habituation trials following a rare auditory sequence were discarded from the analyses. In each block the number of rare trials varied between 22 and 30. Auditory stimulations were presented with Eprime v1.1 (Psychology Software Tools Inc., Pittsburgh, Pa.). Instructions to pay attention to the stimuli and to count deviant stimuli were delivered verbally to all patients at the beginning of each block. All subjects performed eight blocks (3-4 min duration) in a fixed order (two runs of XX, YY, XY, YX frequent stimulation).

High-Density Scalp EEG Recordings

EEG recordings were sampled at 250 Hz with a 256-electrode geodesic sensor net (EGI, Oregon, USA) referenced to the vertex. Recordings were band-pass filtered (form 0.2 to 45 Hz). Trials were then segmented from −200 ms to +1336 ms relative to the onset of the first sound. Trials with voltages exceeding ±150 V, eye-movements activity exceeding ±80 mV and eye-blinks exceeding ±150 mV were rejected. Trials were baseline corrected over the first 200 ms window preceding the onset of the first sound. Electrodes with a rejection rate superior to 20% across trials were rejected and were interpolated. Trials with more than 20 corrected electrodes were rejected. The remaining trials were digitally transfoinied to an average reference. All these processing stages were performed in the EGI Wavefolin Tools Package.

Connectivity measures were based on a spatial Laplacian transformation of the EEG—a computation also known as Current Source Density (CSD) estimate and implemented by (24). CSD consists, roughly, in subtracting, from each electrode, the activity of its neighboring electrodes. This has the main advantage of increasing spatial resolution and minimizing the influence of common sources on multiple distant electrodes, due to volume conduction.

Calculation of Putative EEG Measures of Consciousness

The inventors calculated the entire set of EEG measures (m) independently for each individual subject, trial and for every electrode ($n_e$=256) or pair of electrodes ($n_e$=32640). Connectivity measures were summarized by calculating the median value from each electrode to all of the other scalp (non-facial) electrodes. In this way all measure distributions ended up with the same number of values per subject and trial ($n_e$=256). Finally, for each subject, these values were again collapsed to two scalars by considering the mean and the standard deviation across trials.

At the exception of ERP measures, analyses were performed on EEG data recorded during the time period when subjects were presented with undifferentiated series of tones (from 200 ms prior to the onset of the first tone to the onset of the fifth tone). Thus, all trials were pooled independently of the condition of auditory stimulation.

Computation of Measures

Event-Related Potentials (ERPs)

Mid-Latency Auditory Potential Corresponding to the First Sound (P1)

In the present study, the P1 was computed by averaging the voltage of a cluster of 7 EEG electrodes surrounding Fz (electrodes [15, 22, 14, 6, 7, 16, 23] in the EGI 256-electrode net) between 68 ms and 116 ms following the onset of the first sound and across all trials.

Contingent Negative Variation (CNV)

In the present study, the CNV was computed by averaging the slope of the EEG electrodes' voltage observed between the onset of the 1st sound to the onset of the 5th sound (Linear regression, from 0 to 600 ms). For univariate analyses, the CNV was summarized as the average slope of a cluster of 7 EEG electrodes surrounding Fz (electrodes [15, 22, 14, 6, 7, 16 and 23] in the EGI net).

P3a

In the present study, the P3a was computed by averaging the EEG electrodes' voltage between 280 ms to 340 ms following the onset of the 5th sound and across local deviant trials only (XXXXY). For univariate analyses, the P3a was summarized as the average voltage of a cluster of 7 EEG electrodes surrounding Fz (electrodes [15, 22, 14, 6, 7, 16 and 23] in the EGI net).

P3b

In the present study, the P3b was computed by averaging the EEG electrodes' voltage between 400 ms to 600 ms following the onset of the 5th sound and across global deviant trials only (rare sequences). For univariate analyses, the P3b was summarized as the average voltage of a cluster of 5 EEG electrodes surrounding Cz (electrodes [9, 186, 132, 81 and 45] in the EGI net).

Mismatch Negativity (ΔMMN) and Contrasted P3a (ΔP3a)

The MMN was estimated by contrasting the local deviant trials (LD=XXXXY) vs. the local standard trials (LS=XXXXX). Each subjects' MMN was thus summarized as the 256-electrode topography of the LD/LS difference in the time window between 140 ms to 192 ms after the onset of the 5th sound. For the univariate analysis, this value was averaged over a subset of electrodes around Fz and Cz (electrodes [15, 22, 14, 6, 7, 16, 23, 9, 186, 132, 81 and 45] in the EGI net)

Similarly, the ΔP3a was estimated using the same contrast than for the MMN but averaging a time window from 280 ms to 340 ms after the onset of the 5th sound. The same electrodes as for the MMN were used for the univariate analysis.

Contrasted P3b (ΔP3b)

The ΔP3b was contrasted between the rare global deviant (GD) trials and the frequent global standard (GS) trials 5. Each subjects' ΔP3b was then summarized as the 256-electrode topography of the GD/GS difference in the time window between 400 ms to 600 ms after the onset of the 5th sound. For the univariate analysis, this difference was averaged over a subset of electrodes around Cz and Pz (electrodes [9, 186, 132, 81, 45, 101, 100, 129, 128, 119 and 110] in the EGI net).

Local Dynamics (within Electrodes)

Spectral Analysis

Power spectral density on each trial was estimated using the Welch method (49). For each trial, each electrode was divided in 500-ms sections with 400 ms of overlap. Sections were windowed with a Hamming window and zero padded to 4096 samples. The power in each frequency band was calculated as the integral of the power spectral density within each frequency bands, and finally log scaled. Frequency-bands of interest were: Delta ($\delta$: 0-4 Hz), Theta ($\theta$: 4-8 Hz), Alpha ($\alpha$: 8-13 Hz), Beta ($\beta$: 13-30 Hz) and Gamma ($\gamma$: 30-45 Hz). Higher frequencies were not estimated as they are generally difficult to capture with EEG.

Estimation of power spectral densities can be influenced by several phenomena (i.e. electrode impedances) creating inter-individual variance in the absolute EEG power. In consequence, following the method proposed in (50), the inventors also estimated normalized versions of the power in the frequency bands by dividing the power in each band by the total energy in the trial (total power of the five frequency bands equal to 100%). These estimates are referred to $\delta_n$, $\alpha_n$, $\beta_n$, and $\gamma_n$ respectively.

Spectral Summaries

Power Spectrum Centroids (MSF, SEF)

Spectral summaries were estimated using the following measures: median power frequency (MSF), spectral edge 90 (SEF90) and spectral edge 95 (SEF95) (reviewed in 51). These measures are defined as the particular frequencies that divide the power spectrum into two parts of equal area (MSF), a lower part equal to 90% of the total area and a higher part equal to 10% (SEF90), or a lower part equal to 95% of the total area and a higher part equal to 5% (SEF95).

In all cases, measures were estimated using the power spectral density for each electrode in each trial.

Spectral Entropy (SE)

The entropy of a time series is a measure of signal predictability and is thus a direct estimation of the information it contains (52). Entropy can be measured in the time domain but also in the spectral domain. Spectral entropy basically quantifies the amount of organization of the spectral distribution (53). The inventors implemented the spectral entropy (SE) measure using the algorithm described for anesthesia monitors (11). The SE index for each electrode in each trial was estimated with the following procedure: i) the power spectral density of each trial was normalized by dividing it by the total energy in that trial; ii) SE was calculated, using the Shannon Entropy formula for all frequency bins:

$$SE = -\Sigma_f PSD_n(f) \log^{[n]}(PSD_n(f))$$

Signal Complexity

Permutation Entropy

Permutation entropy (PE), introduced by Bandt & Pompe (25), is an effective method to compare time series and distinguish different types of behavior (e.g. periodic, chaotic or random). One key feature of the method is its robustness to low signal to noise ratios compared to other similar methods (25). The basic principle of this method is the transformation of the time signal into a sequence of symbols before estimating entropy. The transformation is made by considering consecutive sub-vectors of the signal of size n. These sub-vectors can be made of either consecutive elements or of elements separated by samples (where is an integer). The parameter thus defines a broad frequency-specific window of sensitivity for this measure (see FIG. 11 for the spectral sensitivity of the method given the present parameters. Since using values larger than 1 induce aliasing effects, the signal was low pass filtered before PE calculation, in order to maintain the frequency-band specificity of each measure. Cutoff frequencies were set according to the following formula:

$$f_{LP} = \frac{80 \text{ Hz}}{\tau},$$

appropriate given the sampling rate. Each sub-vector of length is associated with a unique symbol, based solely on the ordering of its n signal amplitudes. Given the parameter there are possible vectors, corresponding to distinct categories of signal variations. After the symbolic transform, the probability of each symbol is estimated, and PE is computed by applying Shannon's classical formula to the probability distribution of the symbols. In this case the inventors computed PE for every electrode in every trial with parameters n=3 and τ=[8, 4, 2, and 1], corresponding respectively to $PE_\theta$, $PE_\alpha$, $PE_\beta$ and $PE_\gamma$. Repeating the analysis with =4 yielded very similar results. However PE becomes harder to robustly estimate for larger n values, because the size of the estimated probability matrix increases rapidly.

Kolmogorov Chaitin Complexity

Algorithmic information theory has been introduced by Andrey Kolmogorov and Gregory Chaitin as an area of interaction between computer science and information theory. The concept of algorithmic complexity or Kolmogorov-Chaitin complexity (K) is defined as the shortest description of a string (or in this case a time series). That is to say, K is the size of the smallest algorithm (or computer program) that can produce that particular time series. Unfortunately, it can be demonstrated by reductio ad absurdum that there is no possible algorithm that can measure K. To sidestep this issue, the inventors can estimate an upper-bound value of K(X). This can be concretely realized by applying a lossless compression of the time series and quantifying the compression size. Capitalizing on the vast signal compression literature, the inventors heuristically used classical open-source compressors (gzip and bzip2) to estimate K(X). The inventors exported as ASCII files the time series for every electrode and trial. K(x) was calculated as the size of the compressed file divided by the size of the original string. The premise is that, the bigger the size of the compressed file the more complex the structure of the time series, thus potentially indexing the local neural processing captured by that sensor. The here used measure interprets complexity as the degree of randomness. Further work will study alternative versions of this measure that could better capture complexity as the critical state between order and randomness (45).

Information Sharing (Across Electrodes)

Phase Locking Value (PLV)

The phase locking value (PLV) proposed by Lachaux et al (46) consists in correlating the phase $\varphi x$ of a signal X to the phase $\varphi y$ of a signal Y at given frequency. The inventors computed PLV using a series of traditional steps: (1) For each frequency-bin of interest (f, in $\delta$ [0-4 Hz], $\theta$ [4-8 Hz], $\alpha$ [8-13 Hz], $\beta 1$ [13-20 Hz], $\beta 2$ [20-30 Hz] and $\gamma$ [30-45 Hz]), each pair of electrodes, and at each trial, the signal X and Y were band-passed filtered at f. (2) Then the inventors applied the Hilbert-transformation to estimate the instantaneous phase $\varphi(\tau)$ and amplitude $\psi(\tau)$ of X and Y at each time point $\tau$. (3) The phase difference ($\varphi\Delta$) between the two signals X and Y was then calculated as:

$$\varphi\Delta(\tau) = \varphi x(\tau) - \varphi y(\tau)$$

Finally, the inventors computed the PLV in each trial separately, from norm of the average phase vector ($\varphi\Delta$) across all time samples of the trial:

$$PLV = \left| \frac{1}{N} \sum \varphi\Delta(\tau) \right|$$

Note that the PLV is traditionally computed directly across trials, in order to estimate the evoked functional connectivity across trials. However, this approach is biased by the number of trial it is computed from (46, 26). In the present study, the inventors overcome this issue by first averaging across time in a given trial, to compute the PLV of that given trial and then averaging this PLV_trial across trials. As the number of time samples is fixed across trials the variability in trial number does not bias the PLV, but, as in any other analysis, only affects the validity of its estimates.

Phase Lag Index (PLI)

The Phase Lag Index (PLI), initially proposed by Stam, Nolte & Daffertshofer (26) measures the asymmetry in the distribution of phase differences between two signals. To estimate it, the first three steps were identical to the PLV. However, in the final step, the sign of the angle of the difference between φx(τ) and φy(τ) was calculated, and averaged across time.

$$PLI = \left| \frac{1}{N} \sum \text{sign}(\varphi \Delta(\tau)) \right|$$

Again, the mean PLI was calculated for each trial, and then averaged across trials. Note that although PLI and PLV are highly related, PLV can more easily conclude that two EEG electrodes are synchronized, because it is sensitive to common sources. By contrast, the PLI is insensitive to perfect, zero-phase synchrony and therefore focuses on connectivity between two electrodes which does not originate from a single common source. Finally, because the PLI is signed across pairs of electrodes, when the inventors needed a summary value of PLI across electrode pairs, the inventors averaged the absolute value of PLI.

Symbolic Mutual Information

In order to quantify the coupling of information flow between electrodes the inventors introduced a novel marker: symbolic mutual information (SMI). This method is based on the PE analysis and is calculated between each pair of electrodes, and for each trial, after the transformation of the time series into sequence of symbols (see methods for permutation entropy). Identically to PE, the symbolic transformation depends on the applied tau parameter (in this case: τ=8,4,2,1 corresponding to $SMI_\theta$, $SMI_\alpha$, $SMI_\beta$ and $SMI_\gamma$).

The non-directional estimation of the coupling is quantified by the mutual information between the two time series. Mutual Information is calculated using the traditional formula:

$$MI(X, Y) = \left| \sum_{x \in X} \sum_{y \in Y} p(x, y) \log\left(\frac{p(x, y)}{p(x)p(y)}\right) \right|$$

where x and y are all symbols present in signals X and Y respectively, p(x,y) is the joint probability of co-occurrence of symbol x in signal X and symbol y in signal Y. Finally p(x) and p(y) are the probabilities of those symbols in each signal.

Global Algorithmic Complexity (GK)

The inventors extended the K index in order to quantify the complexity of the whole recording to each trial. To this aim, the inventors applied the same procedure than for the local K, but instead of compressing independently the signal from each electrode, the inventors compressed the time series from all electrodes simultaneously. In this way, the inventors have one measure of Global algorithmic complexity (GK) per trial. Because this measure may be confounded with the complexity of the individual time series corresponding to each electrode, the inventors also introduced a version (GKn) of the measure normalized to the mean K of all electrodes for that trial. Identically as for K, GK was estimated using two types of compressors: gzip and bzip.

The data provided to the classifier corresponds to the 94 EEG measures, topographically summarized as the mean and the standard deviation across non-facial electrodes. Similarly to topographical analyses, connectivity measures were first averaged as the median value each electrode shared with all other non-facial electrodes, and subsequently summarized as the mean and standard deviation across these non-facial averages. The data provided to the classifier thus corresponded to a matrix X of n samples (EEG recordings) by f features (f=94 EEG measures*2 topographical summaries) and a vector y of n samples corresponding to subjects' states of consciousness (1: VS, 2: MCS, 3: Conscious). Note that to account for the small number of CS patients and Healthy subjects, for this analysis the latter were regrouped in a single category.

Multivariate Pattern Analyses Computation

The Support Vector Classifier (SVC) was repeatedly cross-validated with stratified k-folding (k=10). Cross validation is a method aiming at testing the performance of a predictive model. It consists in repeatedly fitting this model on a subset of the data (training set) and subsequently testing it on the remaining data (test set). Stratified k-folding consists in arranging the partitioning of the data so that training and test sets keep constant proportion of each category samples. Stratified folding thus aims to minimize fold-specific effects. The classifier is fitted on the train set and subsequently assigns, to each test sample, a continuous probability of belonging to each class (VS, MCS, Conscious, see below). So as to minimize folding effects, the predicted probabilities of each sample were averaged across 100 repetitions of the SVC, each using pseudo-randomly partitioned stratified folding.

The inventors used a one-against-one discrimination SVC method (47), as MCS are likely more difficult to be contrasted to the combination of CS and VS than to each group separately. In practice, for each pair-wise comparison, the SVC categorizes each sample into one of two considered categories. Three comparisons were thus performed (VS/MCS, MCS/CS, VS/CS). The SVC algorithm then estimate the category in which each subject is most likely to belong.

For each comparison, the SVC aims at finding the optimal linear combination of features (w) that separates the training samples with distinct classes in the hyperspace of features. As there are more features than samples (f>>n), there is an infinity of possible w. A penalization parameter is thus used to find a solution which is likely to generalize to another dataset, and hence avoid over-fitting. Here, the penalization parameter C, was chosen by nested cross-validation among the values=[0.001 0.01 0.1 0.2 0.5 1 2 10] using a grid-search method (48). In other word, in each fold, the classifier subdivided the training set to find the optimal C.

The SVC can provide a continuous probability by fitting the distribution of the samples with regard to w (49). To do so, a sigmoid function is fitted from the distributions of the signed distances separating the train samples and w. This sigmoid fit is then used to monotonically transform the signed distance separating the test samples and w into a meaningful probability (49).

Within each fold, the inventors applied two successive preprocessing steps fitted on the train samples and subsequently applied to the test samples. Because SVCs are not scale independent, the inventors first normalized each feature (remove mean, divide by standard deviation). The inventors then applied a 20% feature selection based on F-tests to reduce the dimensionality f of the problem.

All MVPAs analyses were performed with the Scikit-learn package (48).

Statistics

Univariate ROC

Pair-wise comparisons were performed across the three clinical groups (VS, MCS and CS), leading, for each measure, to three statistical comparisons (1:VS/MCS, 2:MCS/CS, 3:VS/CS). Several measures appeared clearly non-Gaussian. The inventors thus implemented a non-parametric statistical method (Mann-U Whitney test) and report the effect size as the Area under the curve (AUC) from an empirical Receiver Operating Curve (ROC) analysis.

The ROC shows the false positive rates (FPR) as a function of true positive rates (TPR). For example, in a comparison of the alpha power between CS and VS patients, one can observed the percentage of CS patients (TPR) who show a higher alpha power than an arbitrarily setup criterion C. By computing the percentage of VS patients who show a higher alpha power than C, the inventors can thus plot the TPR and the FPR at a fixed criterion. By testing all possible empirical criterion (all patients' values), the inventors can draw the ROC curve, and compute the AUC. An AUC of 50% implies that the TPR is on average equal to the FPR, which thus means that no difference is observed across the two groups. Values higher than 50% means that CS have on average higher alpha power, and values lower than 50% implies that CS patients have lower alpha power than VS patients.

Note that the estimates of statistical effect size are intrinsically problematic in mass-univariate analyses, as one tends to look at the effect size of significant tests only. However, the effect size itself is an estimate and subject to error. The inventors decided to make all values available to the reader, but stress that it is incorrect to peak the best measure without leading to an overestimation of its effects size.

Each measure is intrinsically high dimensional, as it was measure on each EEG electrode (n=256) or on each pair of EEG electrodes (n=32640). To sum up these large datasets, the inventors thus summarized each measure in a single value.

ERPs measures were summarized as the mean value observed in regions of interests traditionally used in the literature.

Connectivity measures computed for each pair of EEG electrodes were summarized as follows:

for each non facial electrode, the inventors computed the median value it shared with all other non-facial electrode. The inventors then average these 224 values to summarize the amount of shared information across the scalp.

All other measures were summarized by averaging the 224 values non-facial electrodes.

To account for the large number of statistical tests (n=94 measures×3 comparisons), statistical significance was systematically corrected for multiple comparison with a false discovery rate method (FDR at alpha=0.05) across all measures and comparisons.

Topographical Analysis

Topographical analyses were performed using a similar approach to the method above. Pair-wise comparisons across clinical states were performed with Mann-U Whitney tests on each electrode separately. Robust regression analyses were performed across the four groups (VS:1, MCS:2, CS:3, Healthy:4) to test for the monotony of the changes observed across states of consciousness. Statistical significance are reported after correction for multiple comparison across electrodes (FDR at alpha=0.05).

Multivariate Pattern Analyses

Multivariate Pattern Analyses (MVPAs) have proven to be an efficient neuroimaging tool to combine multiple sources of evidence within a single test (50). In the present case, each analysis aimed at predicting the clinically-defined state of consciousness (VS, MCS or conscious) of each subject from the EEG-based measures of conscious processing. For this purpose, the inventors used a Support Vector Classifier (SVC) (48) with a probabilistic output calibration.

Example 2

Measurement of Consciousness Using SMI

The inventors have evaluated whether new mathematical indices of information sharing, derived from EEG recordings, could determine whether awake but non-communicative patients are or are not conscious—a difficult clinical question which leads many conscious but non-communicating patients to be misclassified as vegetative (1, 3, 55). This research capitalized on a large number of experimental studies in normal subjects (reviewed in (5)), which have identified brain activity patterns that systematically distinguish trials in which stimuli were reported as visible or as invisible. These patterns include the presence of a late non-linear "ignition" of brain-scale neural assemblies, with activation propagating dorsally and anteriorly into a broad parietal and prefrontal network, leading to increased bidirectional functional connectivity, particularly over long cortical distances (27, 29-31, 57). Several theories of conscious processing share the hypothesis that it is this massive bidirectional communication between several distant cortical areas, making information globally available, that the inventors experience as a conscious state (22, 23, 45, 57, 58-63).

The inventors therefore put this idea to a test by computing measures of global information sharing and contrasting minimally different states of consciousness in patients suffering from Disorders of Consciousness (DOC). To quantify global information sharing, the inventors relied on novel indices which are based on a robust transformation of EEG signals into sequences of discrete symbols (25), followed by a quantification of their shared and transferred (FIG. 1) information.

To provide a minimal contrast, the inventors restricted ourselves to patients with preserved arousal abilities (largely intact sleep-wake cycle), but who suffer from an inability to communicate with their surrounding environment. Within this category, vegetative State (VS) patients present no clinical signs of conscious behavior, whereas Minimally Conscious State (MCS) patients demonstrate fluctuating but consistent deliberate responses (64). The inventors compiled an unusually large database of 181 EEG recordings with high spatial density (256 electrodes). The inventors first tested whether MCS patients present systematically more information sharing across cortical sites than VS patients. The inventors also compared these results to those obtained in conscious subjects, including 25 clinical recordings, to assess the monotony of the observed effects across states of consciousness (see example 1). The inventors then ran a series of control analyses to check for the potential effects of etiologies and of the duration of the DOC, as well as for a variety of EEG artifacts potentially confounding the observed effect. Finally, the inventors probed whether VS patients present impairments of bidirectional transfer of information across cortical sites.

Symbolic Mutual Information Increases with Conscious State

The inventors have used Symbolic Mutual Information (SMI) to evaluate the extent to which two EEG signals present a nonrandom arrangement of their joint fluctuations, suggesting that they participate in a joint state and share partially similar information. This method presents two advantages. First, it looks only for qualitative or "symbolic" patterns of increase or decrease, rendering it more robust to noise (25).

Second, the mutual information measure sets no a priori on the type of interactions, making this approach capable of detecting non-linear relations. SMI depends on two parameters: the size (n=3) and the temporal spread ($\tau$) of the symbols. The inventors computed SMI after current source density (CSD) transformation of the EEG data, which increases the spatial focalization of the data over active sources, and therefore reduces the possibility of common-source artifacts.

When considering the median SMI across all channel pairs, analyses with $\tau$=32 ms revealed that VS patients presented significantly lower mutual information across EEG channels than MCS patients (p=0.0018), CS patients (p=0.004) and healthy controls (p=0.01). These results thus suggest that VS patients exhibit an overall impairment in information sharing. A robust regression confirmed that median SMI predicted the clinical group to which the subjects belonged (1=VS, 2=MCS, 3=CS, 4=Healthy; p<0.001). These effects were partly reproduced using a smaller temporal spread of the symbols ($\tau$=16 ms): VS<MCS (p=0.098), VS<Healthy (p<0.0001), MCS<Healthy (p=0.002), CS<Healthy (p=0.002)). Time constants capturing shorter events ($\tau$=4 ms and $\tau$=8 ms) did not reveal any significant trends across consciousness states.

A Centro-Posterior Topography of Impairments

Topographies summarizing the amount of information that each EEG channel shares with others suggest that an information sharing deficit in DOC patients was present over most scalp regions (pFDR<0.05 in more than 90% of the CSD transforms of EEG channels). Frontal areas generally showed significantly smaller differences across conscious states than posterior regions (e.g. Fz<Pz, beta=0.003, p=0.023).

Further analyses focusing on each channel pair confirmed this overall effect. As it is difficult to interpret the very large number of pairs of CSD estimates (256×(256−1)/2=32 640 pairs), the inventors reduced the data to 16 clusters composed of ~16 CSD estimates each. The results, confirmed that VS patients exhibited an overall reduction of information sharing from and to posterior areas: 56% of the 120 cluster pairs showed significantly smaller SMI in VS than in MCS and than in CS patients (at p<0.05; 47% at pFDR<0.05).

Symbolic Mutual Information Indexes Consciousness Regardless of Etiology or Acuteness.

The inventors examined whether the change in SMI could be explained by the patients"differing etiologies or by the acuteness of their impairment. An ANOVA across patients, states of consciousness (VS, MCS, CS) and etiologies (anoxia, stroke, traumatic brain injury (TBI) and other) showed that SMI was affected by patients"state (F(2,125) =4.54, p=0.012) but not by their etiology (F(3,125)=0.62, p=0.605). The difference in SMI between VS and non-VS patients was observed in stroke (p=0.013) and TBI patients (p=0.009). Although in the same direction, this effect did not reach significance in the two remaining groups.

Similarly, after categorizing each patient in one of the three types of delay separating their accident from the time of EEG recording (acute, intermediate and chronic), the inventors found a main effect of consciousness state (F(2, 136)=3.62, p=0.02) but no effect of delay (F(2,136)=0.98, p=0.378). The effect of state of consciousness on functional connectivity was observed in acute patients (p=0.042) and in inteiniediate patients (p=0.002) but it did not reach significance in the chronic category (p=0.286), although it was again in the same direction.

Finally, testing for interaction effects between states, delays and etiology revealed no significant two or three-way interaction effect (all p>0.434). Overall, these results indicate that SMI is sensitive to states of consciousness independently of the etiology and the acuteness of the disorder.

Long-Distance Functional Correlations Index Consciousness

EEG is notorious for its low spatial resolution, mainly due to volume conduction of electric currents through the head tissues. Although the inventors applied a Current Source Density (Laplacian) transform to reduce these artifacts, the connectivity analyses may still be partly confounded by common source artifacts. The inventors confronted this issue with two types of analyses. Firstly by restricting SMI analysis to pairs of channels spread apart by more than 10 cm. The results still demonstrated a significantly smaller SMI in VS patients relative to MCS and CS patients (pFDR<0.05). The SMI difference between patient groups was largely independent of spatial distance, suggesting that it reflected a global brain-scale change in information sharing.

Second, the inventors computed the Phase Lag Index (PLI), another measure of functional correlation which minimizes common-source artifacts by discarding zero-phase correlations. For nearby pairs of EEG recording sites (distances<5 cm), PLI quickly dropped towards zero, confirming that this analysis helped minimize common source artifacts. However, for larger distances, PLI again varied across patient groups. On average, the VS patients"medium (>10 cm) and long-distance (>15 cm) PLI were significantly lower than MCS and CS patients"(medium: p<0.05, long: p<0.001) for frequencies between 4 and 8 Hz. Higher frequencies did not showed systematic effects. Importantly, low (<4 Hz) frequencies presented stronger PLI in VS than in CS patients (p<0.01), confirming that unconsciousness is associated with enhanced synchrony in the low-frequency range, as observed during anesthesia and sleep (64, 44).

In summary, both distance and PLI analyses suggest that the overall reduction in functional connectivity observed in VS patients likely reflects a genuine change in long-distance functional connectivity.

Information Sharing Deficits are Replicated After Auditory Stimulation

The above analyses were performed on time periods during which patients were repeatedly stimulated with 4-sound sequences (see Methods). The inventors also replicated these analyses on an independent time interval following these auditory stimulations. The results were similar to the one described above.

Directional Measures Show a Bidirectional Deficit of Information Transfer Across Anterior and Posterior Regions SMI and PLI are non-directional measures of information sharing across two sites. The inventors also implemented a Symbolic Transfer Entropy measure (STE) (see FIG. 1) in order to estimate the directionality of the flow of information. Like Granger causality analysis, STE can quantify the information transfer from A to B, from B to A, or both.

Figure 2:
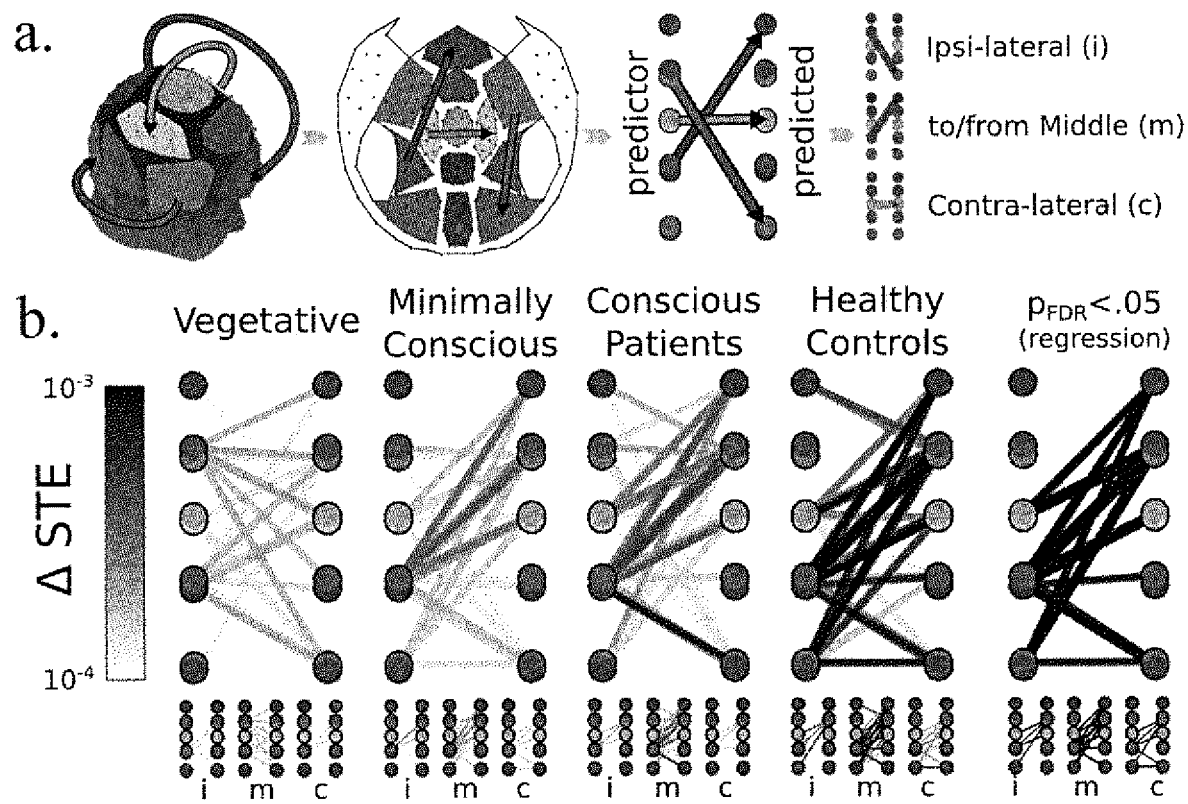
FIG. 2. Symbolic Transfer Entropy reveals a change of information transfer from and to centro-posterior regions across states of consciousness.

STE results, summarized in FIGS. 2, 3 and 4, suggest that the amount of bidirectional information transfer from and to clusters surrounding postero-central electrode Pz is associated with the subjects"state of consciousness ($p_{FDR}$<0.01). Note however that pair-wise comparisons between groups of patients were significant but did not resist FDR correction for multiple comparisons (centroposterior to centro-anterior regions: VS-MCS, p>0.05, VS-CS: p<0.05, $p_{FDR}$>0.05).

For any electrode pair, the inventors also estimated ΔSTE which captures the imbalance of information transfer between two signals and which provides a robust measure directly interpretable in terms of net information flow. Results are displayed in FIG. 2. ΔSTE was positive from centroposterior areas to frontal regions, and the degree of imbalance was associated with consciousness ($p_{FDR}$<0.01). In other words, patients who showed more evidence of consciousness showed a larger directional transfer of information from posterior regions to frontal areas. Although similar trends were observed amongst multiple clusters of EEG channels, including Fz to Cz, Oz to Cz and Oz to Fz connections, pair-wise comparisons between VS and other clinical states revealed only modestly significant differences in the balance of postero-anterior information transfer (p<0.01, but $P_{FDR}$>0.05).

The inventors reasoned, however, that the CSD transform could have increased the noise level in recordings because it involves the computation of a spatial derivative over nearby EEG signals. The CSD transform is not strictly necessary for the STE measure, because the STE computation includes a subtraction of within-sensor mutual information and therefore STE, unlike SMI, is essentially immune to common-source artifacts (STE would be zero if two sensors picked a common source). Thus, the inventors replicated their STE analyses without the CSD transform. All of the above trends were replicated and reinforced, and suggested that bidirectional infoimation exchanges, particularly over the centro-posterior region, index the state of consciousness (see FIGS. 3.b and 4.b).

Discussion

Several theoretical models of consciousness predict that global brain-scale information sharing should provide a consistent signature of conscious processing [22, 56, 66, 67, 68]. In agreement with this prediction, the inventors have shown that infoimation sharing across cortical areas, estimated with an original analysis of a large number of EEG recordings (FIG. 5), increases as a function of state of consciousness and separates vegetative state (VS) from minimally conscious states (MCS), conscious state (CS) and healthy (H) subjects. Topographical and cluster mapping results showed that the increase was particularly prominent across centro-posterior areas. Traditional spectral-based measures replicated this result in the theta band, including in different auditory stimulations conditions. Finally, CSD transform of the EEG recordings, distance analyses and PLI estimates consistently suggested that the present results truly reflect changes in long-distance functional connectivity and are not due to a single common source being picked up by distinct EEG channels.

The observed changes in long-distance functional connectivity fit with the idea that consciousness may be affected by many distinct anatomical lesions to the cortex and its white matter, thalamic nuclei, or brain stem nuclei (69). In particular, several studies have underlined the prominent role of diffuse white matter lesions in persistent vegetative state (70-79). These anatomical lesions may lead to functional deficits in thalamo-cortical (80-82) as well as cortico-cortical communication (17, 83-88) and to abnormal default mode network activity in VS patients (20, 74, 85, 88-82).

The present results also fit with recent EEG studies. Fingelkurts and collaborators have provided a series of original analyses differentiating groups of patients based on their resting state EEG (93, 94, 95). They show that the "operational synchrony" is higher in MCS patients than in VS patients suggesting an correlation between information sharing and consciousness state. Similarly, Lehembre et al (35) observed a higher functional connectivity across frontal and posterior electrodes in MCS than in VS patients. Compared to these findings, this study presents several important advantages. The inventors analyzed a much larger patient cohort, with high-density recordings that allow the estimation of distance and directionality of information exchanges. The inventors also rely on a robust estimate with a demonstrable insensitivity to etiology and to common-source artifacts.

Topographically, these results show that the largest differences in information sharing were over the centro-posterior region. Although this effect may appear at odds with the preponderant role of the prefrontal cortex in conscious processing (5, 21, 96), it fits with the recent identification of posterior cingulate and precuneus as essential hubs of a major long-distance cortical network (5, 87, 97, 98) and the correlation of the activity of mesio-parietal regions with the state of consciousness (99, 100). In particular, numerous studies have highlighted a frequent hypoactivation of the precuneus and the posterior cingulate in VS patients (2, 100). These areas are also involved in the default mode network, whose regions have been repeatedly associated with self-referential conscious projective activities in the domains of time (episodic memory of past and future), space (spatial navigation mental imagery), and social interactions (theory of mind) (see reviews in (102-104). It is possible that impairments are more easily detectable in these regions because of their elevated baseline activity and metabolism in normal conscious subjects, and that conscious processing is also supported by other areas such as the prefrontal cortex. Further analyses, either using intracranial recordings or source reconstruction, should help to narrow down the location of the network of areas underlying consciousness. Directional connectivity analyses, estimated with Symbolic Transfer Entropy (STE), suggest that bidirectional information flow, both from and to centro-posterior areas, indexes consciousness. The balance of information transfer (ΔSTE), a measure which is more robust to noise artifacts, presented similar effects, but also emphasized the forward transmission of information (from central towards more anterior prefrontal regions) as a major correlate of consciousness. These results complement a series of similar observations reported in conscious subjects as well as in patients presenting partial or complete loss of consciousness because of epilepsy or other brain lesions or anesthesia. They fit with the idea that conscious processing arises from bidirectional (bottom-up and top-down) information sharing by enabling information encoded in posterior cortical processors to gain access to, and be amplified by, higher association cortices (5). Still, two methodological reasons suggest that this aspect of the results should be considered with caution. First, the present analyses were performed with CSD transformed EEG recordings, which only provide coarse information about the localization of the underlying sources. Computing SMI after cortical source modeling is an interesting avenue for further research, but would be computationally complicated given the very large number of time points and cortical sources. Furthermore, it is unlikely to be spatially accurate given the patients"lesions.

Second, imaging studies are necessarily limited in their ability to estimate causal relationships. Further work using intracranial recordings and electric or magnetic stimulations will thus be required to determine whether bottom-up and/or top-down information flow is necessary for consciousness.

Nevertheless, the inventors may note that the unique intracranial recording study that compared functional connectivity for visible versus invisible images supports the present conclusions of increasing long distance synchrony, bidirectional flow, and enhanced forward propagation during conscious processing.

The present results are based on an unusually large dataset of 181 high-density EEG recordings from 126 distinct subjects in different states of consciousness. This large size allows the inventors to demonstrate the reliability of these indices across patients suffering from various etiologies and across distinct durations of the disorder of consciousness. Previous studies have typically used much smaller numbers of subjects with a very broad range of etiologies and deficit durations (see FIG. 5 for a formal comparison) and therefore were unable to explicitly test the reproducibility of their measures. While Boly et al. (33) argue that the finding of a significant effect in a small number of heterogeneous patients guarantees a robust effect, the inventors disagree (34) and find it preferable to replicate in separate subgroups. In the present case, the inventors present evidence that the cause (traumatic brain injury, stroke, and anoxia) and the acuteness of disorders of consciousness cannot explain the difference of global information sharing from MCS to VS.

The present study could be criticized for pooling over a group of VS patients with presumed loss of consciousness, while recent results with fMRI suggest that some of them may actually show preserved consciousness and intentionality undetectable by classical clinical examinations. Current estimates suggest that this category of patient is rare, however, attaining at most 15-20% (7) and thus minimally affecting the conclusions derived from this study. If anything, the comparisons were made more conservative if the inventors accidentally included a few conscious patients in the VS category. The inventors agree that, in the future, it will be crucially important to apply the present SMI and STE measures to individual cases of VS patients, in order to detect non-communicating patients with preserved consciousness. Indeed, based on current and other EEG measures, the inventors have developed an automatic computerized classification system (example 3). While overall successful in classifying VS and MCS patients, this algorithm does place a few patients clinically diagnosed as VS into the MCS category—and these patients do appear to recover earlier and shift to the clinical MCS category.

Taken together, these results support theories that associate consciousness either with a reverberation of neuronal activity in posterior networks (68), or with a highly distributed brainscale system of areas forming a global workspace or "dynamic core". While future studies will evaluate markers assessing specifically the integration of information exchanged across brain regions, the present measures may already usefully supplement the panoply of behavioral and neuroimaging tools available to diagnose disorders of consciousness. Relative to other proposed markers of consciousness in DOC patients, the present approach, based on a discrete symbolic labeling of ongoing EEG patterns, presents several advantages. First, it relies on an easily recorded parameter (EEG), available in all clinics, rather the complex and costly setting of functional MRI. Second, it indexes spontaneous EEG and can therefore be computed in the absence of any task instruction (although the present analyses were conducted on recordings obtained during an auditory test). Other tests currently require the patient to understand and maintain, for several minutes, a complex instruction such as imagining playing tennis, retrieving the response to a spoken question, or counting deviant sounds. These tests are therefore asymmetrical: when positive, they are highly indicative of preserved consciousness, but they may also fail to detect residual consciousness if the patient also suffers from hearing, linguistic, attentional or working memory deficits. For instance, in (7), 28 out of 33 MCS patients, who therefore gave consistent behavioral signs of consciousness upon clinical examination, showed no signs of communication via imagined tennis playing or spatial navigation. Fluctuations in consciousness may explain this finding. This factor may also affect this study, and stresses the importance of obtaining several recordings in order to increase the sensitivity of the measure and the confidence in its absence in individual VS or MCS patients.

Future research will investigate whether the present technique, which quantifies any form of residual brain-scale communication, proves more sensitive than other tests. As a first step in this direction, in example 3 it is shown that, for the systematic discrimination of VS and MCS patients, the present MSI measure is much more sensitive than the recording of event-related potentials during the local-global test (18). Ultimately, a combination of such techniques, each capitalizing on a distinct signature of consciousness, is likely to prove most useful in the clinic.

Example 3

Combination of Approaches to Increase Acuity of Consciousness Detection Methods

Introduction

The multiplicity of theoretical proposals and the practical need to improve diagnosis in DOC patients call for a systematic test of the capacity of candidate measures to index states of consciousness. The inventors provide an extensive analysis of empirically and theoretically derived measures of conscious activity that can be extracted from a large database of EEG recordings in DOC patients. The inventors show that local low-frequency power and complexity measures, together with long-range information exchange, are privileged markers of conscious states. These measures and their respective fluctuations are sufficiently robust to support an automatic classification system capable of predicting the clinical outcome of individual VS patients.

Below is presented a brief description of each measure used in this example.

Event Related Potentials

The auditory paradigm was designed to elicit both early and late event-related potentials, in order to test the theoretical proposal that early components correspond to unconscious stages of processing, whereas late components would be associated with conscious access (21, 107). In addition to early auditory P1 and N1 potentials, this paradigm elicited several early and late responses related to the detection or the expectation of an auditory novelty: the contingent negative variation (CNV), the mismatch negativity (MMN) and the P3b components.

The CNV is a slow negative drift ranging from the first to the last sound of each trial, measured by its slope over the frontal electrodes. This component has been reported to be relevant in distinguishing conscious and non-conscious patients using this paradigm (108-20). The MMN is elicited by a change in pitch in the last of the five tones (XXXXX versus XXXXY). This component has been repeatedly reported under non-conscious conditions, although its amplitude can be modulated by subjects' attention and conscious state (attention modulation (18), in sleep (42) and in DOC patients (18, 37, 38, 39, 43, 110, 111). Following the Local Global paradigm, the late P3b component was isolated by contrasting frequent and expected auditory sequences to rare and thus unexpected auditory sequences. For instance, in a given block, subjects were repeatedly presented to AAAAB trials. On rare occasions (20%), an AAAAA sequence was presented. In another block, subjects were frequently presented to AAAAA, and rarely to AAAAB. Contrasting rare and frequent trials is thus orthogonal to the local change in pitch within a given sequence. The P300b response is thought to be present only when subjects are attentive and aware of the violations (10, 20, 36).

Ongoing Activity

The rest of the measures were derived from ongoing EEG activity, acquired during the early stimulation window. Although neutral auditory stimuli were presented during these time periods, it is possible to quantify ongoing EEG activity because the latter dominates over evoked responses by approximately one order of magnitude. Moreover, auditory stimulations limit drowsiness by repeatedly calling patients' attention, and could thus help better differentiating MCS from VS patients. Ongoing EEG measures were organized according to two dimensions: whether they capture local dynamics or connectivity; and whether their theoretical background lies in a spectral decomposition of the EEG signal, or in information theory.

Measures of EEG Spectrum

Local dynamics refer to measures computed within a given EEG electrode or Current Source Density (CSD) estimate. At this level, spectral measures are traditionally applied to quantify EEG rhythms or broadband frequency patterns, many of which have been proposed to distinguish conscious states in anesthesia, sleep and DOC patients. A classical finding is that unconscious subjects, compared to conscious ones, exhibit a reduction in power in the alpha band (8-13 Hz) and an increase in low frequencies such as the delta band (1-4 Hz). In the inventors dataset they estimated power in five frequency bands (delta to low gamma). Frequency analyses were completed with spectrum summary measures that summarize distribution of power over various frequencies using a single value, for instance its median or its spectral entropy (SE, characterizing the complexity of the spectrum). These measures of spectrum summaries have been previously used to characterize the EEG recordings of DOC patients and subjects under anesthesia.

Measures of Complexity

Novel techniques from the fields of dynamical systems and information theory also provide insights into normal and perturbed neural mechanisms (48). These measures may prove more appropriate to detect and characterize changes in the EEG that are not unveil using traditional spectral frequency content methods (112).

The inventors included a representative set of infoli tation theory measures of local dynamics. In particular, permutation entropy (PE) is an increasingly used method to detect dynamical changes in a time series (113) which is known for its high resistance to low signal to noise ratios compared to other similar methods (25). PE has been successfully applied to detect, with EEG, loss of consciousness under anesthesia (44, 114). As described in details below, PE estimate the entropy of a signal transformed into a sequence of discrete "symbols". These symbols are generated from the qualitative (i.e. ranking) up and downs of the signal.

The inventors introduce an original method to quantify the complexity of EEG signals based on the application of the Kolmogorov-Chaitin complexity (K). This measure quantifies the algorithmic complexity (115, 116) of a single sensor's EEG by measuring his degree of redundancy. Algorithmic complexity of a given string (in this case an EEG sequence) can be described as the length of shortest computer that can generate it. A short program corresponds to a less complex sequence. The inventors estimated K by quantifying the compression size of the EEG using variants of the Lempel-Ziv zip algorithm (117). This measure has been previously applied to detect changes in the cortical activity in anesthetized animals (118).

Measures of Information Sharing

Connectivity, in the sense of information sharing across distant cortical areas, has been proposed as a key element of several theories of consciousness. Recent advances in theoretical neuroscience have shown that long-distance communication could be established by a frequency-specific synchronization of across different brain areas (119). Intracranial recordings and M/EEG comparing neural processing elicited by subliminal and visible images revealed an increase an association between conscious perception and long-range synchrony in the beta and gamma bands. Moreover, recent EEG studies suggest that VS patients present lower functional connectivity than MCS and CS patients. In the present study, the inventors have evaluated synchrony with two traditional spectral methods: phase locking value (PLV) and phase lag index (PLI).

However, such spectral methods cannot capture information integration based on non-oscillatory mechanisms. In his Information Integration Theory, Tononi (45) has proposed a framework to quantify such exchanges with a simple mathematical formula. However, this so-called "Phi" measure remains so far difficult to apply to large-scale EEG data. To handle this issue, the inventors introduce two original method of information sharing: symbolic mutual information (SMI) and global Kolmogorov-Chaitin (GK). SMI can robustly quantify non-oscillatory functional connectivity by transforming the EEG signals into symbolic sequences. GK evaluates the algorithmic complexity of the pooled EEG signals for all electrodes, and thus reflects how much information is shared across them.

For all measures, the inventors introduced a final distinction between their average value and their fluctuation across time (in this case indexed across trials). This method proved to extract independent information from the BOLD signal in an fMRI experiment (120). Thus, the inventors studied both the mean ($\mu$) and standard deviation ($\sigma$) of each measure across trials. While the mean across trials is the traditional operation used to quantify an EEG measure, measuring its variability over the 20 minutes of recording might be meaningful to distinguish between patient groups.

Results

The inventors analyzed a large set of 181 high-density EEG recordings from 167 patients (75 VS, 68 MCS, 24 CS) and 14 controls (see example 1 for details), acquired in a twenty-minute paradigm designed to probe the depth of processing of auditory regularities (118) (FIG. 6a). This procedure allowed us to jointly quantify the event-related potentials (ERPs) evoked by exogenous stimuli and the presence of endogenous fluctuations in the EEG, while maximizing and normalizing the patients' attention and vigilance. From each recording, the inventors systematically extracted a representative set of candidate measures organized according to a theory-driven taxonomy (FIG. 6b). Full details and motivations for each measure can be found in example 1 above and hereafter.

A first distinction separates measures of the processing of external stimuli (auditory ERPs) from measures reflecting ongoing aspects of the EEG. Given that theories differ in their attribution of conscious awareness to early or late ERPs (5), these are further classified according to their latency (early, <250 ms, versus late, >300 ms) and whether they are locked to local or global regularity aspects of the sequence of tones (18). Measures of ongoing EEG activity are further classified based on two criteria: 1) dynamics of a single-electrode versus connectivity measures across electrodes; and 2) whether the measure is based on spectral frequency content or on information-theoretic estimates of sequence complexity which do not presume any specific hypothesis about the signal. Finally, all of these measures are estimated on a trial-by-trial basis, leading to two measures: the inter-trial average, which reflects the overall value across the test and the fluctuation of this measure (standard deviation), during the recording period, which tests the hypothesis that stability may be a hallmark of consciousness (121).

EEG Differences Between Groups of DOC Patients

To reduce dimensionality and to quantify the discriminative power of each measure, the inventors first summarized spatial information by considering the average over pre-defined electrodes regions of interest. This procedure yielded a total of 94 measures per subject.

The first objective was to investigate which measures showed significant differences across groups of DOC patients. To this aim, the inventors implemented receiver operator curves (ROC) and quantified classification performance from the area under curve (AUC) (FIG. 7). See example 1 for details on how this analysis is corrected for multiple comparisons). An AUC of 50% corresponds to chance classification. AUC values larger than 50% imply that the given measure increases for the higher conscious state (i.e. MCS>VS). The converse also applies for AUC<50% (i.e. MCS<VS).

Average Measures Across Time

Only two out of seven computed ERP components significantly discriminated VS from CS patients (FIG. 7) and none of them could significantly discriminate the crucial VS-MCS comparison. The MMN and the P300, two ERPs which signal the detection of violations of the auditory regularities in the stimulation showed only a very modest variation across the different groups. Although MMN discriminated VS from CS and MCS from CS (respectively, AUC=70.4%, p FDR<0.01 and AUC=66.4%, p FDR<0.05), confirming that it increases when consciousness recovers (34), it did not discriminate VS from MCS, consistent with the fact that mismatch detection remains present in the absence of consciousness, even in coma patients (35). In contrast with the ERP components, almost all of the measures extracted from power in spectral bands had good discrimination capacity (FIG. 7). All measures showed monotonous effects from VS to CS patients groups, and six out of ten of them succeeded in discriminating VS from MCS. Within the lower frequencies, delta showed decreasing power (from VS to CS) separating VS from MCS (AUC=32.0%, $p_{FDR}$<0.01) and a fortiori from CS patients (AUC=18.9%, $p_{FDR}$<0.001). On the contrary, alpha and theta powers increased from VS to CS. Alpha power was the most discriminative spectral measure, separating VS from MCS (AUC=71.3%, $p_{FDR}$<0.001), and a fortiori from CS patients (AUC=84.3%, $p_{FDR}$<0.0001). Because of these opposing variations of low (delta) and higher (alpha and above) frequencies, spectral summaries such as the median spectral frequency (MSF), indexing the relative distribution of power in the spectrum, were particularly efficient. MSF proved to be the most efficient measure of this class distinguishing VS from the two other groups (MCS>VS, AUC=63.3%, $p_{FDR}$<0.05. CS>VS, AUC=76.2%, $p_{FDR}$<0.001). Finally, the structure of the spectral distributions estimated with spectral entropy (SE) was also very informative. This measure showed that CS and MCS patients presented less predictable spectral structure (higher entropy) than VS patients (MCS>VS, AUC=63.9%, $p_{FDR}$<0.01. CS>VS, AUC=79.4%, $p_{FDR}$<0.001).

Algorithmic (or Kolmogorov-Chaitin) complexity (K) estimates the complexity of a sequence based on its compressibility. Several theories predict that the complexity of information integration (122) or distributed processing (5) is elevated during conscious states. In agreement with this prediction, the inventors found that measured of complexity based on EEG compression discriminated VS from MCS ($K_{bz}$: MCS>VS, AUC=71.2%, $p_{FDR}$<0.001), as complexity increased in patients with better clinical consciousness states. A complementary mathematical approach is permutation entropy (PE) which evaluates the regularity of the probabilistic distributions of patterns in the signal (25). The inventors found that PE-based measures were particularly efficient in the theta frequency range, discriminating VS from the other groups ($PE_\theta$: MCS>VS, AUC=71.9%, $p_{FDR}$<0.001, CS>VS, AUC=83.1%, $p_{FDR}$<0.0001). Again, a greater PE, indicating a more complex and unpredictable distribution, indexed consciousness.

Similarly to the spectral measures at a single recording site, measures of functional connectivity between two recording sites proved particularly efficient in the lower-frequency domain. Amongst the spectral connectivity measures, only the phase-locking value (PLV) and phase-locking index (PLI) in the delta band were weakly significant, loss of consciousness being indexed by greater delta synchrony. Connectivity measures based on information theory, such as symbolic mutual information (SMI), demonstrated a higher sensitivity, as the information exchanges increased from VS to CS. VS patients presented significant lower SMI than both MCS ($SMI_\theta$: AUC=64.3%, $p_{FDR}$<0.01) and CS patients ($SMI_\theta$: AUC=68.7%, $p_{FDR}$<0.05), consistent with the theoretical notion that loss of consciousness in VS reflects impaired information exchanges across brain areas. In example 2, the inventors replicated these results on detailed analysis of the connectivity patterns across groups.

Fluctuation of Measures Across Time Convey Independent Information

Stability in evoked activity has been proposed as a marker of consciousness (121). Extrapolating this idea, the inventors hypothesized that the variability in time of a given measure, as opposed to its average value, might add independent information about consciousness. Indeed, fluctuations in ERPs proved very informative to discriminate patients groups, in sharp contrast with the poor discrimination achieved with their averaged values. Five out of eight ERPs components showed decreasing fluctuations as conscious state increased. Fluctuations in spectral, information-based and connectivity measures also efficiently discriminated between groups (FIG. 7). Interestingly, the inventors did not observe a strong covariance between the classifying power of a given measure based on its average and its fluctuations. For instance, average Kolmogorov complexity increased with increasing levels of consciousness, while its fluctuations decreased. This finding indicates that a stream of consciousness is associated with a complex and stable EEG pattern.

FIG. 8 provides a graphical comparison of discrimination power based on the mean or the fluctuation of each measure for the MCS/VS contrast. This analysis summarizes different types of measures. Some simply fail to separate these two groups. Others, show an increase in both the average and the fluctuation over time for MCS compared to VS (this is the case for power in the theta, alpha and beta pwers, MSF and SMI$_\theta$). Yet other measures show a dissociation of average and fluctuation. In particular, the state of consciousness is associated with a high average but a low fluctuation of K, PE$_\theta$ and PE$\alpha$, indicating that a stable and lasting increase in complexity and entropy reflects a conscious patient. Conversely, conscious states are associated with a low average and high fluctuation of power and PLI in the delta band: bouts of delta-dominated EEG may occur in the normal conscious brain, but stable and intense delta waves are a sign of non-consciousness. Finally, the remaining measures were discriminative only for averages (i.e., SE) or for fluctuations (i.e., PLI in beta and alpha bands) across time.

The latter finding suggests that consciousness implies a constantly fluctuating stream of transiently phase-locked brain states.

Topographical Variability Across Measures and Groups

While the above analysis considered measures collapsed across electrodes or electrode pairs, the inventors then investigated whether specific scalp topographies provide information that discriminates between groups. The inventors performed this analysis because: 1) it informs us about the spatial distribution of these measures, 2) it can demonstrate non-redundancy across measures and 3) it may highlight optimal recording regions for clinical practice. FIG. 9 presents topographies for a selection of measures (for a full description, see FIG. 12). Visual inspection revealed three salient aspects: (1) for all measures that effectively discriminated between groups in the previous section, a majority of electrodes showed efficient discrimination power; (2) Regression analyses across the four groups indicated monotony of the changes across states of consciousness (3) topographies differed widely across groups (for a given measure) and across measures (for a given group comparison). For example, while measures based on delta power showed group differences primarily over medial and frontal electrodes, measures based on mutual information and complexity differed on posterior electrodes (FIG. 9).

Such distinct topographies suggest that no single localized source conveys all the information used to discriminate between conscious and unconscious patients.

Combining Measures Improves Discrimination

The inventors next examined whether these EEG measures could be combined to improve discrimination of the state of consciousness of each individual patients. One goal was to determine whether combined measures, acting in concert, combine synergically to improve discrimination between groups or whether, instead, measures are highly redundant and, as a consequence, the best measure provides information comparable to the entire set. To this aim the inventors used as classification method a support vector machine (SVM) (48). The SVM was repeatedly fitted and evaluated on independent datasets using stratified nested cross validations. As output, this classifier quantifies the probability of each recording to belong to one group (VS, MCS or CS) for the given combination of measures. The average of the probability of being correctly classified was significantly increased from 45.3% to 50.2% (p<$10^{-5}$, see FIG. 13) when compared the case of use of a single measure versus the use of the whole set. In other words, the combination of measures led to a better discrimination of patients' states of consciousness than the unique best measure identified along the cross-validation.

The inventors repeated this comparison but, in this case, focusing on the variation of the discrimination power on the 2×2 comparisons. Results showed that the comparisons, using the best single measure, reached AUC=70.2% for VS-MCS, AUC=76.4% for MCS-CS and AUC=88.8% for VS-CS. On the other hand, when computed using the whole set of measures, AUCs were significantly higher than the best single measure: VS-MCS: 73.3% (p<0.01), MCS-CS: 77.5% (p<0.01), VS-CS: 90.5% (p<$10^{-4}$).

Automatic Classification and Consciousness Recovery Prediction

Automatic classification achieved above-chance levels of accuracy to identify the state of each individual patient. Identification rates were high compared to chance performance (33%): 65% of VS-diagnosed patients, 62% of MCS-diagnosed patients and 53% of CS-diagnosed subjects were classified in their respective categories purely from their brain activity (FIG. 10). Moreover, examination of the discrepancies between the EEG-based classification and clinical diagnosis (FIG. 10) revealed that the majority belonged to adjacent categories: misclassified CS subjects were mostly classified as MCS (42%) and misclassified VS patients were majorly classified as MCS (32%).

Disagreement between the automatic classification and the clinical label may represent an error of the classifier, but also, potentially, the presence of EEG-based information not accessible to the clinician. To investigate whether the information derived from neurophysiological activity may improve the diagnosis of consciousness' state, the inventors tested whether VS patients classified as MCS or CS would be later show signs of intentional behavior that may have been missed at the time of the recording. Most patients clinically diagnosed as VS and classified as VS from their EEG activity showed no signs of regaining consciousness in the two months following EEG recording. By contrast, the proportion of clinically diagnosed VS patients who later showed signs of consciousness was significantly (p=0.01) increased to 48% for the set of patients who were classified as CS or MCS based on their EEG activity. It should be emphasized that the mere clinical assessment at the time of the recording, based on the sum of the Coma Recovery Scale-Revised (CRS-R) scale or each sub-scores, neither predicted the VS patients' recovery nor the automatic classification category (see below for comparisons according to CRS-R subscores). Hence, within a behaviorally indistinguishable group of clinical VS patients, neurophysiological measures proved to provide substantial information about future improvement of consciousness. These results also strengthen the possibility of detecting conscious activity independently of overt behavior evidence.

Automatic Classification and Recovery Vs. CRS-R

To assess whether the recovery of the patients from the VS state could be predicted from the the Coma Recovery Scale Revised (CRS-R) scores at the moment of clinical evaluation of consciousness the inventors compared the CRS-R between the clinical VS patients that did recover vs. the VS patients that didn't recover. None of the CRS-R subscores or the full sum distinguished between the two groups (Mann-U Whitney, p>0.08 for CRS1, p>0.22 for CRS2, p>0.44 for CRS3, p>0.63 for CRS4, N.A.1 for CRS5, p>0.31 for CRS6 and p>0.41 for sum of CRS-R subscores).

The inventors repeated the analysis but this time the inventors compared the CRS-R scores of clinical VS patients classified as VS by the SVM classifier to the CRS of patients classified as MCS by the classifier. Again, none of the CRS-R subscores could differentiate between these two groups. (Mann-U Whitney, p>0.08 for CRS1, p>0.41 for CRS2, p>0.65 for CRS3, p>0.71 for CRS4, N.A.1 for CRS5, p>0.22 for CRS6 and p>0.33 for sum of CRS-R subscores).

Discussion

The inventors systematically evaluated potential signatures of consciousness in a large dataset of high-density bedside EEG recordings of patients suffering or recovering from disorders of consciousness. Many candidate measures could discriminate between VS and CS, probably indexing consciousness directly but also indirectly through its consequences on arousal, instruction understanding, active maintenance of stimuli and instructions in working memory, task monitoring, etc. Crucially, only a few of these measures were effective to discriminate the minimal contrast comparing VS and MCS patients. The inventors focus the discussion on the subset of measures which appeared to be most relevant to the objective identification of conscious processing from the patterns of EEG activity.

Spectral Measures Specific to Conscious State

Spectral power analysis revealed that alpha and theta powers were significantly lower in VS than in MCS patients, whereas delta power showed the opposite pattern. Classical EEG findings have revealed similar increases in low-frequency oscillations in coma and deep sleep (123). Here the inventors have demonstrated their relevance to distinguish VS from MCS patients, as recently reported in smaller groups of patients (35, 46). The fronto-parietal topography of these spectral effects is consistent with a crucial role of fronto-parietal networks in a 'global workspace' (GW) mediating a serial stream of conscious states at theta-like frequencies (100-300 ms per state). This regional hypothesis should be confirmed with cortical source analysis, which was not attempted here given the difficulty of obtaining an accurate source model in patients with massive brain and skull damage (34).

The inventors also have shown that spectral measures exhibit greater fluctuations in MCS than in VS patients, which agrees with the definition of MCS as a fluctuating state (124) and show that, contrariwise, a stable state of increase delta and reduced alpha-theta power is a solid sign of non-consciousness. Potential differences in vigilance, rather than consciousness, between MCS and VS patients may contribute to explain these results. Indeed, the CRS-R sub-score of vigilance was slightly larger in MCS than in VS patients (p<0.05). However, it is noteworthy that the statistical significance of the spectral measures was incomparably stronger (stepwise fit: $p<10^{-4}$ vs 0.05) than this behavioral effect.

Reduced EEG Complexity in the Vegetative State

Multiple EEG measures of signal complexity (SE, PE, K) discriminated VS from MCS patients, and the inventors show that the increase of EEG complexity and stability monotonically increased with patients' states of consciousness. This original result confirms that the complexity of cortical activity indexes consciousness, as explicitly formulated for instance by the dynamic core model of Tononi and colleagues (23, 61,122). According to these models, a minimal level of complexity is required to encode a rich and differentiated representation within a conscious core. Regions specifically implicated in the coding of conscious representations would thus show higher complexity during conscious than during non-conscious states, exactly as observed here.

The inventors found that consciousness was indexed not only by a high information complexity, but also by a stability of this complexity, with reduced fluctuations during the 20-minute recording. This result extends to spontaneous EEG the findings of a recent fMRI study showing that neural activation patterns are more reproducible when evoked by a visible than by an invisible stimuli (121). The inventors hypothesize that one property of the conscious brain is to achieve both a reproducible perception of identical sensory stimuli, as well as a never-ending internal chain of computations of roughly equal complexity, even in the absence of sensory stimulation. One intriguing aspect of this work is that spectral measures showed greater fluctuations in MCS compared to VS, whereas information complexity was more stable in the MCS than in the VS. This dissociation suggests that distinct neuronal mechanisms are captured by these measures. Indeed, there is no contradiction here, as spontaneous thought could be associated with states of fixed temporal complexity, yet variable duration (from hundreds of milliseconds to several seconds), thus creating significant fluctuations in frequency contents.

Increase of Long-Distance Connectivity in Conscious States

One of the most striking differences between patients was an increase in long-distance connectivity measures in the theta band (SMI theta) in MCS as compared to VS patients. This result strengthens previous findings relating long-distance synchronization with conscious states in DOC patients in similar frequency bands. In addition to generalizing this finding to a large dataset, the results precise the topography of this large-scale increase of communication by reporting a maximal effect over mesio-parietal areas, in close agreement with recent works showing the crucial role of precuneus and posterior cingulate 'hubs' in conscious integration.

Future research will investigate whether directional connectivity analysis also helps to distinguish these clinical groups (example 2). The importance of long-distance cortical communication in consciousness fits with a set of perturbational TMS-EEG studies conducted in DOC patients (125), sleep (126) and anesthesia (127). Most interestingly, the inventors also find larger fluctuations of functional connectivity in MCS than in VS patients, in particular in PLI (from delta to β1) and in SMIθ. Recent studies conducted with epileptic patients with implanted electrodes (SEEG) for pre-surgical mapping reported that loss of consciousness during the transition from partial simple to partial complex seizures was marked by a sudden excessive increase in cortico-cortical and thalamo-cortical synchrony (128). The inventors results lead to the testable prediction that this excessive synchronization would correspond to a marked decrease of information complexity, which would in turn explain the loss of consciousness.

A Collection of Measures Outperforms Traditional ERPs

This study reveals a low sensitivity of traditional ERPs extracted after signal averaging. EEG studies using active cognitive paradigms to probe conscious states often use ERPs as their main measures (36, 39) in particular because they index specific cognitive processes. Indeed, the auditory regularities violation task used here was designed to dissociate the automatic and unconscious MMN from the P3b complex associated with conscious access. The inventors have previously demonstrated that this P3b ERP measure, which indexes the detection of a violation of a global regularity, can be very useful in individual patients a specific marker of consciousness, sometimes in advance on clinical evaluations (10, 20). The present results, unfortunately, confirm that it lacks in sensitivity when used alone. High inter-individual variability in ERP timing and topography across patients may explain this finding. In a recent work, the inventors used a systematic within-subject decoding approach at the single-trial level in order to improve the detection of global P3-like ERP responses, resulting in a significant increase in detection at the individual level (reported herein). This finding call for the inclusion of this technique along with the successful proposed here to improve diagnostic performance. The present results also show that ERP fluctuations are sensitive measures, perhaps because their presence indicates a modulation by switches of attention and mind-wandering across the 20-minute recording, which would themselves be good indicators of preserved consciousness. Fluctuations on the ERPs could also be reflecting the fact the VS patients present more low-frequency power. This activity can directly produce more fluctuations on the ERPs of those patients. The present dataset cannot distinguish between the two hypotheses.

The Value of Combining Several Measures of Consciousness

A significant gain in discrimination was obtained by combining several EEG measures. This is an important result for both theoretical and clinical reasons. Theoretically, this gain of information suggests that these markers do not simply reflect distinct facets of the same neural process, but tap onto distinct and dissociable features of conscious states. From the medical perspective, these results stress the usefulness of combining a subset of EEG measures (spectral, informational and connectivity based). The first attempt to provide an individual patient diagnosis decoding is noteworthy: most patients were correctly decoded on the basis of their EEG measures, and misclassified patients were always classified in the closest clinical category. Furthermore, the inventors decoder discovered EEG information indicating a better functional status in a subset of clinically defined VS patients. This result fits with previous fMRI findings indicating that VS is not a homogeneous category, and that some VS patients may actually be minimally or even fully conscious (3). Because EEG is an economic, widespread, and easily repeatable method, it may prove more efficient than fMRI in order to identify these patients in the clinic. Indeed, these results point to the possibility that a reduced set of EEG measures, computed from a few selected scalp electrodes, could serve as a reliable bedside tool to probe consciousness in DOC patients.

Example 4

Measuring Consciousness Using KSC

The inventors tested whether KSC could distinguish EEG recordings corresponding to VS patients from recordings corresponding to MCS patients. The inventors recorded 75 VS patients and 67 MCS using a 256-electrode geodesic sensor net (EGI, Oregon, USA).

When considering the mean KSC across all channels. Analyses with τ=32 ms revealed that VS patients presented significantly lower complexity across EEG channels than MCS patients ($p<0.01$). The area under the curve (AUC) of the receiver operating characteristic (ROC) curve showed a discrimination power of 62.88% (FIGS. 15 and 16).

Example 5

Further Evaluation of wSMI of Consciousness

To test whether global information sharing can also discriminate conscious states, the inventors introduce a novel measure, weighted Symbolic Mutual Information (wSMI), which evaluates the extent to which two distinct EEG signals present non-random arrangements of their joint fluctuations, suggesting that they share partially similar information. This method presents three main advantages. First, it looks for qualitative or "symbolic" patterns of increase or decrease of the signal (FIG. 14.a). The symbolic transformation depends on the length of the symbol (here, k=3) and its temporal spread (here, τ=[4, 8, 16 or 32] ms, see methods. Second, the mutual information measure sets no a priori on the type of interactions, making this approach capable of detecting non-linear coupling (FIG. 14.b). Last but not least, the weights help disregarding spurious correlations across two EEG signals capturing common sources (FIG. 14.c). The inventors computed wSMI after a current source density (CSD) transformation of EEG signals, which increases the spatial focalization of the data over active sources, and therefore reduces common-source artifacts.

To maximize the specificity of the measure with regard to conscious state, the inventors focused their analyses on DOC patients with preserved arousal abilities, but who suffer from an inability to communicate with their surrounding environment. Within this category, vegetative state (VS) patients present no clinical signs of conscious behavior, whereas minimally conscious state (MCS) patients demonstrate fluctuating but consistent deliberate responses.

wSMI Increases with Consciousness State

When considering the median wSMI across all channel pairs, analyses with τ=32 ms revealed that EEG recordings acquired from VS patients (n=75) presented significantly lower information sharing across EEG channels than MCS patients' (n=68): U=3737, $p<10^{-5}$, AUC=0.73; than CS patients' (n=24): U=1445, $p<10^{-5}$, AUC=0.80; and than healthy controls (n=14): U=890, $p<10^{-4}$, AUC=0.85 (FIG. 19.b). These effects were observed for all tested parameters but τ=4 ms (FIG. 23.a)—which captures relatively short events.

wSMI is Robust to Syndromes' Etiology and Acuteness

An analysis of variance across patients, states of consciousness (VS, MCS, CS) and etiologies (anoxia, stroke, traumatic brain injury (TBI), other) showed a main effect of consciousness state ($F(2,119)=11.96$, $p<10^{-4}$), but no main effect of etiology ($F(3,119)=1.83$, $p=0.145$). The difference in median wSMI between VS and MCS patients was observable in anoxia (U=181, p=0.001, AUC=0.87), TBI (U=126, p=0.001, AUC=0.78) and stroke (U=102, p=0.024, AUC=0.72) patients (FIG. 18.a).

Similarly, after categorizing each patient in one of the three types of delay separating their accident from the time of EEG recording (acute [<25 days], intermediate and chronic [>50 days]), the inventors found again a strong main effect of consciousness state ($F(2,132)=10.01$, $p<10^{-4}$) but no main effect of delay ($F(2,132)=2.24$, $p=0.110$). The difference in median wSMI between VS and MCS patients was observable in chronic (U=295, p=0.022, AUC=0.71) and intermediate (U=98, $p<10^{-4}$, AUC=0.84) patients and marginal in acute subjects (U=417, p=0.081, AUC=0.64).

wSMI Impairments are Dominated by Centro-Posterior Regions

Topographies summarizing the amount of information that each EEG channel shares with others (FIG. 19.a) suggest that the information sharing deficit in VS patients was present over most scalp regions ($p_{FDR}<0.05$ in more than 97% of the CSD transforms of EEG channels). When comparing VS and MCS, the median wSMI in frontal areas (Fz) were less impaired in VS patient than in the posterior regions (Pz): U=2035, p=0.038, AUC=0.60.

As it can be difficult to interpret the very large number of pairs of EEG channels (n=32 640; see FIG. 25), the inventors reduced the data to 16 clusters composed of ~16 CSD estimates each. The results, plotted in FIG. 20, confirmed that VS patients exhibited an overall reduction of information sharing mainly with posterior areas: 48% of the 120 cluster pairs showed significantly smaller wSMI in VS than in MCS and than in CS patients ($p_{FDR}<0.05$).

wSMI is Specifically Affected at Long Distances

EEG is notorious for its low spatial resolution, mainly due to volume conduction of electric currents through the head tissues. Although the inventors applied a CSD transform to reduce these artifacts, the above analyses may still be partly confounded by common source artifacts.

To address this issue, the inventors investigated the relationship between wSMI and the Euclidian distance separating each pair of EEG channel. As can be seen on FIGS. 21 and 25, for nearby pairs of EEG recording sites (distances<5 cm), wSMI quickly dropped towards zero, confirming simulations showing that this analysis help minimizing common source artifacts (FIG. 22). Moreover, statistical comparisons of consciousness states as a function of distance revealed no difference between groups of patients at short distances (d<8.3 cm): all p>0.10. By contrast, at medium (8.3 cm<d<15.4 cm) distances, VS showed a strong reduction of wSMI as compared to MCS (U=3825, $p<0.10^{-6}$, AUC=0.75), CS (U=1439, $p<0.10^{-5}$, AUC=0.80) and healthy subjects (U=801, $p<0.10^{-3}$, AUC=76). Similar results were observed at long distances (d>15.4 cm) (FIG. 21.c). Finally, similar effects were observed with $\tau=8$ ms and $\tau=16$ ms (see FIG. 25.a).

In summary, these results strongly suggest that VS patients are selectively impaired in medium and long distance information sharing.

SMI Results

Symbolic mutual information (SMI) between two channels is a closely similar measure to wSMI, except that it equally considers all conjunction of symbols observed across two signals. This measure, is however subject to multiple forms of artifacts. Indeed, head movement, eye blinks, muscle contractions as well as the volume conduction of electric fields all tend to generate similar signals in different EEG sensors. SMI is thus very likely to overestimate the amount of information sharing across distinct cortical sources.

Distance analyses of SMI summarized in FIG. 25.b show that, in contrast to wSMI, SMI rapidly increases as the distance between two EEG sensors diminishes. Moreover, results showed that VS' SMI was significantly smaller than MCS (U=3297, p=0.003, AUC=0.65), CS (U=1235, p=0.006, AUC=0.69), and healthy (U=749, p=0.012) subjects at medium, as well as at long (U=[3300, 1223, 729], p=[0.002, 0.009, 0.02], AUC=[0.64, 0.68, 0.69]) distances. However, at short distances, VS patients' SMI was also significantly lower than MCS (U=3165 p=0.013, AUC=0.62), CS (U=1217 p=0.010, AUC=0.68), and healthy (U=773 p=0.005, AUC=0.73) subjects. Moreover, the difference between VS and MCS subjects was not higher (or lower) at low than at medium (U=4644, p=0.310, AUC=0.45) or than at long (U=2188, p=0.144, AUC=0.57) distances.

The lack of interaction between consciousness state and distances make these SMI results potentially ambiguous, because VS' overall impairment may be due to smaller amount of common source artifacts. By contrast, not only were wSMI more robust than SMI, but it allowed finding such critical interaction.

Replication of wSMI Results Using Different Time Periods of Recordings

It is possible that the results are specific to the auditory stimulations presented during this experiment. The inventors therefore replicated their analyses on different time periods following auditory stimulations. The obtained results were very close to the one reported in the main manuscript. At short distances, no significant difference was observed across states of consciousness (all p>0.406). However, at medium distances, VS subjects presented a smaller wSMI than MCS (U=3698, $p<10^{-5}$, AUC=0.73), CS (U=1404, $p<10^{-4}$, AUC=0.79) and healthy (U=793, p=0.002, AUC=0.76) subjects. Similarly, at long distances, VS subjects presented smaller wSMI than MCS (U=3383, p<0.001, AUC=0.67), CS (U=1334, $p<10^{-4}$, AUC=0.75) and healthy (U=825, p<0.001, AUC=0.80) subjects. Again, the difference observed between VS and MCS subjects was stronger at medium (U=3410, p<0.001, AUC=0.68) and long (U=1685, p<0.001, AUC=0.67) distances than at short distances.

Together, these results show that VS' impairment in wSMI is not specific to a single type of auditory condition. To strengthen these results, future analyses should however investigate the variation of wSMI in other conditions such as during sleep, resting state and other tasks requiring subjects' attention.

Distance Analyses: All Parameters

The inventors replicated the distance analyses reported in the main manuscript using three other $\tau$ values [4, 8, 16 ms]. At $\tau=16$ ms, results were closely similar to those initially observed with $\tau=32$ ms. No differences between VS and MCS' wSMI was observed at short distances, but a strong wSMI impairement amongst VS patients was observed at medium (U=3826, $p<10^{-6}$, AUC=0.75) and to a lesser extent at long (U=3356, p=0.001, AUC=0.66) distances. VS subjects also presented smaller wSMI than CS, and healthy controls (all p<0.01) at these two distances. The difference between VS and MCS subjects appeared significantly larger at long than at short distances: U=1679, $p<10^{-3}$, AUC=0.67. At $\tau=8$ ms, no differences were observed at short distances, but VS patients, again, showed a smaller wSMI than MCS (U=3224, p=0.006, AUC=0.63), CS (U=1361, p<0.001, AUC=0.76) and healthy subjects (U=860, p<0.001, AUC=0.82). VS subjects had slightly lower wSMI than CS (U=1139, p=0.0515, AUC=0.63) and healthy subjects (U=721, p=0.028, AUC=0.69). However, on average MCS subjects showed higher wSMI, this difference wasn't significant (p=0.38). Finally, at $\tau=4$ ms, no robust effect was observed: VS subjects never presented a significantly lower (or higher) wSMI than MCS, CS or healthy subjects: all p>0.10.

All together, these results show that the parameter $\tau$ changed the sensitivity of the test, but, at the exception of $\tau=4$ ms, the general pattern described in the main manuscript was consistently observed: VS patients showed an overall wSMI reduction at medium and/or long distances, but no effect at short distances. These results therefore support the claim that VS patients are specifically impaired at medium/long distance information sharing.

PLV and PLI

The inventors also analyzed the present data with more traditional functional connectivity/correlational analyses such as phase locking value (PLV) and phase lag index (PLI). Results are summarized in FIG. 25.e-h.

As expected, distance analyses showed that PLV presented a similar pattern than SMI: overall PLV rapidly increases as the distance between two EEG channels approaches 0. By contrast, PLI presented a similar pattern to wSMI: its value rapidly decreases as the distance between two EEG channels approaches 0. The inventors therefore focus on PLI results. Distance analyses were performed across four distinct set of distances ([1.2-6.6] cm, [6.6-11.8]

cm, [11.8-17.1] cm, [17.1-22.2] cm), which appeared to better summarize the overall pattern observed across all possible distances.

Comparison across states of consciousness and distances showed two small effects. At very low frequencies (<4 Hz), PLI appeared marginally larger in VS patients' than in MCS: U=[2088, 2121, 2059, 2027], p=[0.062, 0.083 0.047, 0.0347], AUC=[0.59 0.58 0.60 0.60] for each of the four distances. However no interaction between consciousness state (VS, MCS) and distances was found. Note that SMI and wSMI could not be tested for such low frequencies (see Supplementary method, Simulations). It would however be interesting to see whether, wSMI could be better at finding such types of interactions and thus rule out the possibility that this change in low frequency PLI is not only due to an increased delta power in VS patients' EEG. Around theta frequencies, VS subjects presented only marginally lower PLI than MCS subjects at medium distances: U=[3075, 3008], p=[0.034 0.064], AUC=[0.60, 0.59], but these two groups of subjects did not differ at short (U=2812, p=0.291, AUC=0.55) nor at long (U=2898, p=0.160, AUC=0.57) distances. At these two medium distances PLI better discriminated VS from MCS patients than PLI at short distances: U=[3348, 1965], p=[0.0013, 0.018], AUC=[0.65, 0.61].

Taken together, results from PLV and PLI analyses suggest that conventional method may be able to capture the observed phenomena: a smaller amount of distant information sharing at frequencies above 4 Hz. However, these results are relatively weak, especially when considering the amount of EEG recordings acquired. PLV and PLI results and would thus not allow a strong correction for multiple comparisons (across distances and frequencies).

Simulations

Effect of Mixture of Sources on SMI and wSMI

To test the validity of the measure, the inventors ran a series of simulations where the inventors tested the robustness of wSMI in detecting the non-linear coupling of distinct sources from two simulated recording devices capturing a heterogeneous mixture of these two sources. These simulations are just presented in order to show i) how common source artifacts affect SMI and ii) why wSMI is robust to the latter. Because several signal and noise parameters were set arbitrarily, the inventors only present results in a qualitative manner in FIG. 22.

The inventors considered two main scenarios: i) the presence, and ii) the absence of coupling between two sources (X and Y). First, in case of the presence of a coupling between X and Y, the inventors generated a random joint probability matrix C ([k!, k!]) as well as a random single probability vector P(S) ([1, k!]) of each symbol S to belong to X. From P(S), the inventors then pseudo-randomly constructed a symbolic sequence X as a sequence of 1000 symbols. The Y symbolic sequence was then constructed by pseudo-randomly generating 1000 consecutive symbols following the transformation of X by the joint probability.

Finally, continuous signals $\hat{X}$ and $\hat{Y}$ were generated from the symbolic sequences X and Y, by generating two random (with a Gaussian distribution) numbers $\alpha$ and $\beta$ for each time point. Each of the k ordinal elements of each symbol was then transformed into a continuous time point accordingly: $S=S\times\alpha+\beta$.

In the second scenario, X and Y symbolic sequences were generated from a homogeneous conjunction matrix indicative of no coupling in the space of interest. Continuous signals X and Y were then generated as in the first scenario.

In each scenario, two simulated EEG sensors were generated by creating more or less homogenous mixture of the two continuous signals. Each simulated sensor captures $\gamma$ % of the neighboring source—and thus (100-$\gamma$)% of the other source. Such setup mimics, two EEG sensors respectively located towards the electric fields' projections of X and Y sources. FIG. 22 shows the qualitative results of these simulations.

Effect of τ on Frequency-Specific Coupling Estimation

Although SMI and wSMI cannot be fully expressed in terms of frequencies, it is useful to see the broad frequency range of information sharing to which wSMI can be sensitive. As mention in the methods, the symbol sizes (τ) affects this frequency range. Sinusoidal signals were thus generated at each frequency ranging between 0 and 60 Hz and sampled at 250 Hz. Pairs of signals were synchronized at π/2 (90°) across two signals. Results of wSMI between such coupling was estimated for each pair of signals at τ=[4, 8, 16, 32] ms. Results are presented in FIG. 25.i, and show that none of the tested τ values can capture low frequency components (<4 Hz), and that the shorter τ is, and the larger and higher becomes its range of frequencies.

REFERENCES

1. Schnakers, Caroline, Vanhaudenhuyse, A., Giacino, J., Ventura, M., Boly, M., Majerus, S., Moonen, G., et al. (2009). Diagnostic accuracy of the vegetative and minimally conscious state: clinical consensus versus standardized neurobehavioral assessment. *BMC neurology*, 9, 35.
2. Laureys, S., & Schiff, N. D. (2012). Coma and consciousness: paradigms (re)framed by neuroimaging. *NeuroImage*, 61(2), 478-91.
3. Owen, A. M., Coleman, M. R., Boly, M., Davis, M. H., Laureys, S., & Pickard, J. D. (2006). Detecting awareness in the vegetative state. *Science*, 313(5792), 1402.
4. Sebel, P. S., Bowdle, T. A., Ghoneim, M. M., Rampil, I. J., Padilla, R. E., Gan, T. J., & Domino, K. B. (2004). The incidence of awareness during anesthesia: a multicenter United States study. *Anesthesia and analgesia*, 99(3), 833-9.
5. Dehaene, S. & Changeux, J.-P. J. P. Experimental and theoretical approaches to conscious processing. Neuron 70, 200-227 (2011).
6. Jordan, D., Stockmanns, G., Kochs, E. F., Pilge, S. & Schneider, G. Electroencephalographic order pattern analysis for the separation of consciousness and unconsciousness: an analysis of approximate entropy, permutation entropy, recurrence rate, and phase coupling of order recurrence plots. *Anesthesiology* 109, 1014-22 (2008).
7. Monti, M. M. et al. Willful modulation of brain activity in disorders of consciousness. New England journal of medicine 362, 579-589 (2010).
8. Goldfine, A. M., Victor, J. D., Conte, M. M., Bardin, J. C. & Schiff, N. D. Determination of awareness in patients with severe brain injury using EEG power spectral analysis. Clinical neurophysiology 122, 2157-68 (2011).
9. Cruse, D. et al. Bedside detection of awareness in the vegetative state: a cohort study. Lancet 378, 2088-94 (2011).
10. Faugeras, F. et al. Probing consciousness with event-related potentials in the vegetative state. Neurology 77, 264-8 (2011).
11. Viertiö-Oja, H., Maja, V., Särkelä, M., Talja, P., Tenkanen, N., Tolvanen-Laakso, H., Paloheimo, M., et al. (2004). Description of the Entropy algorithm as applied in the Datex-Ohmeda S/5 Entropy Module. *Acta anaesthesiologica Scandinavica,* 48(2), 154-61.
12. Gill, M., Green, S. M., & Krauss, B. (2003). Can the bispectral index monitor quantify altered level of consciousness in emergency department patients? *Academic emergency medicine: official journal of the Society for Academic Emergency Medicine,* 10(2), 175-9.
13. Schnakers, C, Ledoux, D., Majerus, S., Damas, P., Damas, F., Lambermont, B., Lamy, M., et al. (2008). Diagnostic and prognostic use of bispectral index in coma, vegetative state and related disorders. *Brain Injury,* 22(12), 926-31.
14. Avidan, M. S., Jacobsohn, E., Glick, D., Burnside, B. A., Zhang, L., Villafranca, A., Karl, L., et al. (2011). Prevention of intraoperative awareness in a high-risk surgical population. *The New England journal of medicine,* 365 (7), 591-600.
15. Gosseries, O., Schnakers, C., Ledoux, D., Vanhaudenhuyse, A., Bruno, M.-A., Demertzi, A., Noirhomme, Q., et al. (2011). Automated EEG entropy measurements in coma, vegetative state/unresponsive wakefulness syndrome and minimally conscious state. *Functional neurology,* 26(1), 25-30.
16. Giacino, J. T., Kalmar, K., & Whyte, J. (2004). The JFK Coma Recovery Scale-Revised: Measurement characteristics and diagnostic utility. *Archives of Physical Medicine and Rehabilitation,* 85(12), 2020-2029.
17. Staniek, M., & Lehnertz, K. (2008). Symbolic Transfer Entropy. *Physical Review Letters,* 100(15), 1-4.
18. Bekinschtein, T. a., Dehaene, S., Rohaut, B., Tadel, F., Cohen, L., and Naccache, L. (2009). Neural signature of the conscious processing of auditory regularities. Proceedings of the National Academy of Sciences of the United States of America 106, 1672-7.
19. Tononi, G., Sporns, O. & Edelman, G. M. A measure for brain complexity: relating functional segregation and integration in the nervous system. *Proceedings of the National Academy of Sciences of the United States of America* 91, 5033-7 (1994).
20. Faugeras, F., Rohaut, B., Weiss, N., Bekinschtein, T., Galanaud, D., Puybasset, L., Bolgert, F., Sergent, C., Cohen, L., Dehaene, S., et al. (2012). Event related potentials elicited by violations of auditory regularities in patients with impaired consciousness. Neuropsychologia 50, 403-18.
21. Dehaene, S., Changeux, J. P., Naccache, L., Sackur, J., and Sergent, C. (2006). Conscious, preconscious, and subliminal processing: a testable taxonomy. Trends in Cognitive Sciences 10, 204-211.
22. Lamme, V. A. F., and Roelfsema, P. R. (2000). The distinct modes of vision offered by feedforward and recurrent processing. Trends in Neurosciences 23, 571-579.
23. Seth, A. K., Barrett, A. B., and Barnett, L. (2011). Causal density and integrated information as measures of conscious level. Philosophical transactions. Series A, Mathematical, physical, and engineering sciences 369, 3748-67.
24. Kayser, J., and Tenke, C. E. (2006). Principal components analysis of Laplacian waveforms as a generic method for identifying ERP generator patterns: II. Adequacy of low-density estimates. Clinical neurophysiology 117, 369-80.
25. Bandt, C., and Pompe, B. (2002). Permutation entropy: a natural complexity measure for time series. Physical review letters 88, 174102.
26. Stam, C. J., Nolte, G., and Daffertshofer, A. (2007). Phase lag index: assessment of functional connectivity from multi channel EEG and MEG with diminished bias from common sources. Human brain mapping 28, 1178-93.
27. Gaillard, R., Dehaene, S., Adam, C., Clémenceau, S., Hasboun, D., Baulac, M., Cohen, L., and Naccache, L. (2009). Converging intracranial markers of conscious access. PLoS Biology 7, 1-21.
28. Sergent, C., Baillet, S., and Dehaene, S. (2005). Timing of the brain events underlying access to consciousness during the attentional blink. Nature neuroscience 8, 1391-400.
29. Melloni, L., Schwiedrzik, C. M., Müller, N., Rodriguez, E., and Singer, W. (2011). Expectations change the signatures and timing of electrophysiological correlates of perceptual awareness. The Journal of neuroscience 31, 1386-96.
30. Del Cul, A., Baillet, S., and Dehaene, S. (2007). Brain dynamics underlying the nonlinear threshold for access to consciousness. PLoS biology 5, e260.
31. Fisch, L., Privman, E., Ramot, M., Harel, M., Nir, Y., Kipervasser, S., Andelman, F., Neufeld, M. Y., Kramer, U., Fried, I., et al. (2009). Neural "ignition": enhanced activation linked to perceptual awareness in human ventral stream visual cortex. Neuron 64, 562-74.
32. Rohaut, B., Faugeras, F., Bekinschtein, T.-a., Wassouf, a., Chausson, N., Dehaene, S., and Naccache, L. (2009). Prédiction du réveil et détection de la conscience: intérêt des potentiels évoqués cognitifs. Réanimation 18, 659-663.
33. Boly, M., Garrido, M. I., Gosseries, O., Bruno, M.-A., Boveroux, P., Schnakers, C., Massimini, M., Litvak, V., Laureys, S., and Friston, K. (2011). Preserved feedforward but impaired topdown processes in the vegetative state. Science (New York, N.Y.) 332, 858-62.
34. King, J.-R., Bekinschtein, T., and Dehaene, S. (2011). Comment on "Preserved feedforward but impaired topdown processes in the vegetative state". Science (New York, N.Y.) 334, 1203.
35. Lehembre, R., Bruno, M.-A., Vanhaudenhuyse, A., Chatelle, C., Cologan, V., Leclercq, Y., Soddu, A., Macq, B., Laureys, S., and Noirhomme, Q. (2012). Resting-state EEG study of comatose patients: a connectivity and frequency analysis to find differences between vegetative and minimally conscious states. Functional neurology 27, 41-7.
36. Lachaux, J. P., Rodriguez, E., Martinerie, J. & Varela, F. J. Measuring phase synchrony in brain signals. *Human brain mapping* 8, 194-208 (1999).
37. Wijnen, V. J. M., Van Boxtel, G. J. M., Eilander, H. J. & De Gelder, B. Mismatch negativity predicts recovery from the vegetative state. Clinical neurophysiology 118, 597-605 (2007).
38. Fischer, C., Luaute, J., Adeleine, P. & Morlet, D. Predictive value of sensory and cognitive evoked potentials for awakening from coma. Neurology 63, 669-673 (2004).
39. Schnakers, C. et al. Detecting consciousness in a total locked-in syndrome: an active event-related paradigm. Neurocase 15, 271-7 (2009).
40. Schnakers, C., Majerus, S., Giacino, J., Vanhaudenhuyse, A., Bruno, M.-A., Boly, M., Moonen, G., Damas, P., Lambermont, B., Lamy, M., et al. (2008). A French validation study of the Coma Recovery Scale-Revised (CRS-R). Brain injury 22, 786-92.

42. Nashida, T. et al. Automatic auditory information processing in sleep. *Sleep* 23, 821-828 (2000).
43. Naccache, L., Puybasset, L., Gaillard, R., Serve, E. & Willer, J.-C. Auditory mismatch negativity is a good predictor of awakening in comatose patients: a fast and reliable procedure. *Clinical neurophysiology* 116, 988-9 (2005).
44. Supp, G. G., Siegel, M., Hipp, J. F. & Engel, A. K. Cortical hypersynchrony predicts breakdown of sensory processing during loss of consciousness. *Current biology: CB* 21, 1988-93 (2011).
45. Finelli, L. A., Borbely, A. A. & Achermann, P. Functional topography of the human nonREM sleep electroencephalogram. *European Journal of Neuroscience* 13, 2282-2290 (2001).
46. Fellinger, R. et al. Cognitive processes in disorders of consciousness as revealed by EEG time-frequency analyses. *Clinical neurophysiology* 122, 2177-84 (2011).
47. Vakkuri, A. et al. Time-frequency balanced spectral entropy as a measure of anesthetic drug effect in central nervous system during sevoflurane, propofol, and thiopental anesthesia. *Acta Anaesthesiologica Scandinavica* 48, 145-153 (2004).
50. Vogt, F., Klimesch, W. & Doppelmayr, M. High-frequency components in the alpha band and memory performance. *Journal of clinical neurophysiology* 15, 167-72 (1998).
51. Rampil, I. J. A primer for EEG signal processing in anesthesia. *Anesthesiology* 89, 980-1002 (1998).
52. MacKay, D. J. C. *Information Theory, Inference and Learning Algorithms.* 640 (Cambridge University Press: 2003).
53. Inouye, T. et al. Quantification of EEG irregularity by use of the entropy of the power spectrum. *Electroencephalography and Clinical Neurophysiology* 79, 204-210 (1991).
54. Knerr, S., Personnaz, L. & Dreyfuss, G. Single-layer learning revisited: a stepwise procedure for building and training a neural network. *Neurocomputing: Algorithms, Architectures and Applications* (1990).
55. Childs, N. L., Mercer, W. N., and Childs, H. W. (1993). Accuracy of diagnosis of persistent vegetative state. Neurology 43, 1465-7.
56. Platt, J. C. Probabilistic Outputs for Support Vector Machines and Comparisons to Regularized Likelihood Methods. *Advances in large margin classifiers* 10, 61-174 (1999).
57. Rees, G., Kreiman, G., and Koch, C. (2002). Neural correlates of consciousness in humans. Nature reviews. Neuroscience 3, 261-70.
58. Baars, B. J. (1989). A Cognitive Theory of Consciousness M. U. P. Cambridge, ed.
59. Lee, U., Mashour, G. A., Kim, S., Noh, G.-J., and Choi, B.-M. (2009). Propofol induction reduces the capacity for neural information integration: implications for the mechanism of consciousness and general anesthesia. Consciousness and cognition 18, 56-64.
60. Tononi, G., and Sporns, O. (2003). Measuring information integration. BMC Neuroscience 4, 31.
61. Tononi, G. (2004). An information integration theory of consciousness. BMC Neuroscience 5, 42.
62. Edelman, G. M. (1989). The remembered present: a biological theory of consciousness (Basic Books).
63. Reza, H., and Nyberg, L. (2005). Common frontoparietal activity in attention, memory, and consciousness: shared demands on integration? Consciousness and Cognition 14, 390-425.
64. Giacino, J. T., Ashwal, S., Childs, N., Cranford, R., Jennett, B., Katz, D. I., Kelly, J. P., Rosenberg, J. H., Whyte, J., and Zafonte, R. D. (2002). The minimally conscious state: Definition and diagnostic criteria. Neurology 58, 349.
65. Bekinstein, T., Dehaene, S. Cohen, L., Naccahe, L. Neural signature of the conscious processing of auditory regularities. *Proceedings of the National Academy of Sciences USA,* 2009, 106, 1672-1677.
66. Tononi, G., and Edelman, G. M. (1998). Consciousness and complexity. Science (New York, N.Y.) 282, 1846.
67. Tononi, G., and Koch, C. (2008). The neural correlates of consciousness: an update. Annals of the New York Academy of Sciences 1124, 239-61.
68. Lamme, V. a. F. (2010). How neuroscience will change our view on consciousness. Cognitive Neuroscience 1, 204-220.
69. Parvizi, J., and Damasio, A. R. (2003). Neuroanatomical correlates of brainstem coma. Brain 126, 1524-36.
70. Ogashiwa, M., and Takeuchi, K. (1976). Clinicopathological studies of the vegetative state: distinction between the vegetative state and brain death. Brain and nerve 28, 901-12.
71. Kampfl, A., Franz, G., Aichner, F., Pfausler, B., Haring, H. P., Felber, S., Luz, G., Schocke, M., and Schmutzhard, E. (1998). The persistent vegetative state after closed head injury: clinical and magnetic resonance imaging findings in 42 patients. Journal of neurosurgery 88, 809-16.
72. Adams, J. H., Graham, D. I., and Jennett, B. (2000). The neuropathology of the vegetative state after an acute brain insult. 1327-1338.
73. Adams, H., Mitchell, D. E., Graham, D. I., and Doyle, D. (1977). Diffuse brain damage of immediate impact type. Its relationship to "primary brain-stem damage" in head injury. Brain 100, 489-502.
74. Fernández-Espejo, D., Bekinschtein, T., Monti, M. M., Pickard, J. D., Junque, C., Coleman, M. R., and Owen, A. M. (2011). Diffusion weighted imaging distinguishes the vegetative state from the minimally conscious state. NeuroImage 54, 103-12.
75. Ammermann, H., Kassubek, J., Lotze, M., Gut, E., Kaps, M., Schmidt, J., Rodden, F. a, and Grodd, W. (2007). MRI brain lesion patterns in patients in anoxia-induced vegetative state. Journal of the neurological sciences 260, 65-70.
76. Newcombe, V. F. J., Williams, G. B., Scoffings, D., Cross, J., Carpenter, T. A., Pickard, J. D., and Menon, D. K. (2010). Aetiological differences in neuroanatomy of the vegetative state: insights from diffusion tensor imaging and functional implications. Journal of neurology, neurosurgery, and psychiatry 81, 552-61.
77. *[missing]*
78. Graham, D. I., Adams, J. H., Murray, L. S., and Jennett, B. Neuropathology of the vegetative state after head injury. Neuropsychological rehabilitation 15, 198-213.
79. Galanaud, D., Perlbarg, V., Gupta, R., Stevens, R. D., Sanchez, P., Tollard, E., De Champfleur, N. M., Dinkel, J., Faivre, S., Soto-Ares, G., et al. (2012). Assessment of White Matter Injury and Outcome in Severe Brain Trauma: A Prospective Multicenter Cohort. Anesthesiology 117, 1300-1310.
80. Laureys, S., Faymonville, M. E., Luxen, A., Lamy, M., Franck, G., and Maquet, P. (2000). Restoration of thalamocortical connectivity after recovery from persistent vegetative state. Lancet 355, 1790-1.
81. Schiff, N. D., Ribary, U., Moreno, D. R., Beattie, B., Kronberg, E., Blasberg, R., Giacino, J., McCagg, C., Fins, J. J., Llinás, R., et al. (2002). Residual cerebral activity 81. and behavioural fragments can remain in the persistently vegetative brain. Brain 125, 1210-34.
82. Zhou, J., Liu, X., Song, W., Yang, Y., Zhao, Z., Ling, F., Hudetz, A. G., and Li, S.-J. (2011). Specific and nonspecific thalamocortical functional connectivity in normal and vegetative states. Consciousness and cognition 20, 257-68.
83. Laureys, S., Goldman, S., Phillips, C., Van Bogaert, P., Aerts, J., Luxen, A., Franck, G., and Maquet, P. (1999). Impaired effective cortical connectivity in vegetative state: preliminary investigation using PET. NeuroImage 9, 377-82.
84. Boly, M., Faymonville, M.-E., Peigneux, P., Lambermont, B., Damas, P., Del Fiore, G., Degueldre, C., Franck, G., Luxen, A., Lamy, M., et al. (2004). Auditory processing in severely brain injured patients: differences between the minimally conscious state and the persistent vegetative state. Archives of neurology 61, 233-8.
85. Bruno, M.-A., Vanhaudenhuyse, A., Schnakers, C., Boly, M., Gosseries, O., Demertzi, A., Majerus, S., Moonen, G., Hustinx, R., and Laureys, S. (2010). Visual fixation in the vegetative state: an observational case series PET study. BMC neurology 10, 35.
86. Vanhaudenhuyse, A., Noirhomme, Q., Tshibanda, L. J.-F., Bruno, M.-A., Boveroux, P., Schnakers, C., Soddu, A., Perlbarg, V., Ledoux, D., Brichant, J.-F., et al. (2010). Default network connectivity reflects the level of consciousness in non-communicative brain-damaged patients. Brain 133, 161-71.
87. Silva, S., Alacoque, X., Fourcade, O., Samii, K., Marque, P., Woods, R., Mazziotta, J., Chollet, F., and Loubinoux, I. (2010). Wakefulness and loss of awareness: brain and brainstem interaction in the vegetative state. Neurology 74, 313-20.
88. Cauda, F., Micon, B. M., Sacco, K., Duca, S., D"Agata, F., Geminiani, G., and Canavero, S. (2009). Disrupted intrinsic functional connectivity in the vegetative state. Journal of neurology, neurosurgery, and psychiatry 80, 429-31.
89. Crone, J. S., Ladurner, G., Höller, Y., Golaszewski, S., Trinka, E., and Kronbichler, M. (2011). Deactivation of the default mode network as a marker of impaired consciousness: an fMRI study. PloS one 6, e26373.
90. Bruno, M. A., Fernández-Espejo, D., Lehembre, R., Tshibanda, L., Vanhaudenhuyse, A., Gosseries, O., Lommers, E., Napolitani, M., Noirhomme, Q., Boly, M., et al. (2011). Multimodal neuroimaging in patients with disorders of consciousness showing "functional hemispherectomy". Progress in brain research 193, 323-33.
91. Soddu, A., Vanhaudenhuyse, A., Bahri, M. A., Bruno, M.-A., Boly, M., Demertzi, A., Tshibanda, J.-F., Phillips, C., Stanziano, M., Ovadia-Caro, S., et al. (2012). Identifying the default-mode component in spatial IC analyses of patients with disorders of consciousness. Human brain mapping 33, 778-96.
92. Boly, M., Tshibanda, L., Vanhaudenhuyse, A., Noirhomme, Q., Schnakers, C., Ledoux, D., Boveroux, P., Garweg, C., Lambermont, B., Phillips, C., et al. (2009). Functional connectivity in the default network during resting state is preserved in a vegetative but not in a brain dead patient. Human brain mapping 30, 2393-400.
93. Fingelkurts, A. a, Fingelkurts, A. a, Bagnato, S., Boccagni, C., and Galardi, G. (2012). EEG oscillatory states as neuro-phenomenology of consciousness as revealed from patients in vegetative and minimally conscious states. Consciousness and cognition 21, 149-69.
94. Fingelkurts, A. A., Fingelkurts, A. A., Bagnato, S., Boccagni, C., and Galardi, G. (2012). DMN Operational Synchrony Relates to Self-Consciousness: Evidence from Patients in Vegetative and Minimally Conscious States. The open neuroimaging journal 6, 55-68.
95. Fingelkurts, A. a., Fingelkurts, A. a., Bagnato, S., Boccagni, C., and Galardi, G. (2011). Toward operational architectonics of consciousness: basic evidence from patients with severe cerebral injuries. Cognitive Processing 13, 111-131.
96. Lau, H. (2008). A higher order Bayesian decision theory of consciousness. Progress in Brain Research 168, 35-48.
97. Parvizi, J., Van Hoesen, G. W., Buckwalter, J., and Damasio, A. (2006). Neural connections of the posteromedial cortex in the macaque. Proceedings of the National Academy of Sciences of the United States of America 103, 1563-8.
98. Meyer, K., and Damasio, A. (2009). Convergence and divergence in a neural architecture for recognition and memory. Trends in neuro sciences 32, 376-82.
99. Alkire, M. T., Hudetz, A. G., and Tononi, G. (2008). Consciousness and Anesthesia. 322, 876-880.
100. Laureys, S., Perrin, F., Schnakers, C., Boly, M., and Majerus, S. (2005). Residual cognitive function in comatose, vegetative and minimally conscious states. Current opinion in neurology 18, 726-33.
101. Pedregosa, F. et al. Scikit-learn: Machine Learning in Python. *The Journal of Machine Learning Research* 12, 2825-2825-2830-2830 (2011).
102. Buckner, R. L., Andrews-Hanna, J. R., and Schacter, D. L. (2008). The brain"s default network: anatomy, function, and relevance to disease. Annals of the New York Academy of Sciences 1124, 1-38.
103. Northoff, G. (2012). What the brain"s intrinsic activity can tell us about consciousness? A tridimensional view. Neuroscience and biobehavioral reviews.
104. Wagner, A. D., Shannon, B. J., Kahn, I., and Buckner, R. L. (2005). Parietal lobe contributions to episodic memory retrieval. Trends in cognitive sciences 9, 44
105. Haynes, J.-D. Multivariate decoding and brain reading: introduction to the special issue. NeuroImage 56, 385-6 (2011).
106. Benedetto, D., Caglioti, E., & Loreto, V. (2002). Language Trees and Zipping. *Physical Review Letters,* 88(4), 048702.
107. Chaitin, G. (1995). The berry paradox. *Complex Systems and Binary Networks.*
108. Walter, W. G., Cooper, R., Aldrige, V. J., Mccallum, W. C. & Winter, A. L. Contingent negative variation: An electric sign of sensori-motor association and expectancy in the human brain. *Nature* 203, 380-384 (1964).
109. Salomon, D. (2007). *Data Compression: The Complete Reference* (Vol. 10). Springer-Verlag.
110. Fischer, C., Luaute, J. & Morlet, D. Event-related potentials (MMN and novelty P3) in permanent vegetative or minimally conscious states. *Clinical neurophysiology* 121, 1032-42 (2010).
111. Kotchoubey, B. et al. Information processing in severe disorders of consciousness: vegetative state and minimally conscious state. *Clinical Neurophysiology* 116, 2441-53 (2005).
112. Stam, C. J. Nonlinear dynamical analysis of EEG and MEG: review of an emerging field. *Clinical neurophysiology* 116, 2266-301 (2005).

113. Cao, Y., Tung, W., Gao, J., Protopopescu, V. & Hively, L. Detecting dynamical changes in time series using the permutation entropy. *Physical Review E* 70, 046217 (2004).
114. Li, X., Cui, S. & Voss, L. J. Using permutation entropy to measure the electroencephalographic effects of sevoflurane. *Anesthesiology*
115. Kolmogorov, A. Three approaches to the quantitative definition of information. *Problems of Information Transmission* 1, 1-7 (1965).
116. Chaitin, G. Information-theoretic computation complexity. *IEEE Transactions on Information Theory* 20, 10-15 (1974).
117. Lempel, A. & Ziv, J. On the Complexity of Finite Sequences. *IEEE Transactions on Information Theory* 22, 75-81 (1976).
118. Shaw, F. Z., Chen, R. F., Tsao, H. W. & Yen, C. T. Algorithmic complexity as an index of cortical function in awake and pentobarbital-anesthetized rats. *Journal of neuroscience methods* 93, 101-10 (1999).
119. Fries, P. A mechanism for cognitive dynamics: neuronal communication through neuronal coherence. *Trends in cognitive sciences* 9, 474-80 (2005).
120. Garrett, D. D., Kovacevic, N., McIntosh, A. R. & Grady, C. L. Blood oxygen level-dependent signal variability is more than just noise. *The Journal of neuroscience* 30, 4914-21 (2010).
121. Schurger, A., Pereira, F., Treisman, A. & Cohen, J. D. Reproducibility distinguishes conscious from nonconscious neural representations. Science 327, 97-9 (2010).
122. Tononi, G. Consciousness as Integrated Information: a Provisional Manifesto. Biol. Bull. 215, 216-242 (2008).
123. Posner, J. B., Saper, C. B., Schiff, N. & Plum, F. Plum and Posner's diagnosis of stupor and coma. 71, (2007).
124. Giacino, J. T. & Kalmar, K. Diagnostic and prognostic guidelines for the vegetative and minimally conscious states. Neuropsychological rehabilitation 15, 166-74 (2005).
125. Rosanova, M. et al. Recovery of cortical effective connectivity and recovery of consciousness in vegetative patients. Brain : a journal of neurology 135, 1308-20 (2012).
126. Massimini, M. et al. Breakdown of cortical effective connectivity during sleep. Science 309, 2228-32 (2005).
127. Ferrarelli, F. et al. Breakdown in cortical effective connectivity during midazolam-induced loss of consciousness. Proceedings of the National Academy of Sciences of the United States of America 107, 2681-6 (2010).
128. Lambert, I., Arthuis, M., McGonigal, A., Wendling, F. & Bartolomei, F. Alteration of global workspace during loss of consciousness: A study of parietal seizures. Epilepsia 53, 2104-10 (2012).

The invention claimed is:

1. A method to measure or monitor consciousness in a subject and to automatically administer a stimulus or medicament comprising the steps:
   a) Acquisition of brain activity signals;
   b) Pre-processing of the brain activity signals of step a);
   c) Symbolic transformation of the signals from step b) into a series of discrete symbols;
   d) Analysis of the series of symbols from step c) using at least weighted symbolic mutual information (wSMI), using the formula:

$$wSMI = \sum_{x \in X} \sum_{y \in Y} w(x, y) p(x, y) \log \frac{p(x, y)}{p(x) p(y)}$$

where x and y are all symbols present in signals from electrodes X and Y respectively; p(x,y) is a joint probability of co-occurrence of symbol x in electrode X and symbol y in electrode Y; and p(x) and p(y) are probabilities of those symbols in each respective signal and w(x,y) is a weight matrix;

e) Calculation of a consciousness index based upon the outcome of the analysis of step d), said consciousness index being equal to the weighted symbolic mutual information (wSMI) obtained from the electrodes X and Y;
   f) Automatic administration of a stimulus or medicament to the subject based on the value of the consciousness index, said stimulus or medicament including sensory stimulus, pharmacological and/or electromagnetic stimulation.

2. The method according to claim 1, wherein said brain activity is recorded using a technique selected from the group comprising: electroencephalography (EEG), Magneto-encephalography (MEG), electro-corticography (ECOG), intracranial local field potentials (LFPs), functional magnetic resonance imaging (fMRI) and functional near-infrared imaging (fNIRS).

3. The method according to claim 2, wherein said brain activity is measured using EEG at least two electrodes and a reference.

4. The method according to claim 1, wherein the recorded brain activity undergoes pre-processing.

5. The method according to claim 1, wherein at least one further analysis of brain activity is performed selected from the group comprising:
   Mid-latency auditory potential corresponding to the first sound (P1); Contingent Negative Variation (CNV); P300a; P300b; Mismatch negativity (ΔMMN); Contrasted P3b (ΔP300b) and Contrasted P300a (ΔP300a); Multivariate pattern analysis of the mismatch negativity and the P300; Spectral analysis; Power spectrum centroids (MSF, SEF); Spectral entropy (SE); Permutation entropy; Kolgomorov symbolic complexity (KSC); Kolmogorov Chaitin complexity; Phase Locking Value (PLV); Phase Lag Index (PLI); Global algorithmic complexity (GK).

6. The method according to claim 1, wherein a consciousness index or combined consciousness index is produced based upon the analysis or the combination of analysis of brain activity.

7. The method according to claim 1, wherein the stimulus or medicament is administered to the subject based on the value of the consciousness index when the consciousness reaches a critical value or target window as shown by electrophysiological markers.

8. The method according to claim 1, wherein the administration of the stimulus or medicament to the subject based on the value of the consciousness index is electromagnetic stimulation.

* * * * *